(12) United States Patent
Savelyeva et al.

(10) Patent No.: US 10,052,370 B2
(45) Date of Patent: Aug. 21, 2018

(54) HER2/NEU CANCER VACCINE

(71) Applicants: Icon Genetics GmbH, Halle (DE); University of Southampton, Southampton (GB)

(72) Inventors: Natalia Savelyeva, Southampton (GB); Franziska Jarczowski, Seegebiet (DE); Romy Kandzia, Halle (DE); Anja Nickstadt, Halle (DE); Frank Thieme, Halle (DE); Victor Klimyuk, Leipzig (DE); Yuri Gleba, Berlin (DE); Duc Bui-Minh, Vienna (AT); Freda K. Stevenson, Abingdon (GB); Warayut Chotprakaikiat, Southampton (GB)

(73) Assignees: ICON GENETICS GMBH, Halle (DE); UNIVERSITY OF SOUTHAMPTON, South Hampton (GB)

( * ) Notice: Subject to any disclaimer, the term of this patent is extended or adjusted under 35 U.S.C. 154(b) by 31 days.

(21) Appl. No.: 14/774,304

(22) PCT Filed: Mar. 11, 2014

(86) PCT No.: PCT/EP2014/000650
§ 371 (c)(1),
(2) Date: Sep. 10, 2015

(87) PCT Pub. No.: WO2014/139672
PCT Pub. Date: Sep. 18, 2014

(65) Prior Publication Data
US 2016/0015796 A1 Jan. 21, 2016

(30) Foreign Application Priority Data
Mar. 11, 2013 (EP) .................................. 13001211

(51) Int. Cl.
*C07K 14/71* (2006.01)
*A61K 39/00* (2006.01)
(Continued)

(52) U.S. Cl.
CPC ........ *A61K 39/0011* (2013.01); *A61K 47/646* (2017.08); *C12N 9/12* (2013.01);
(Continued)

(58) Field of Classification Search
None
See application file for complete search history.

(56) References Cited

U.S. PATENT DOCUMENTS 6,015,567 A * 1/2000 Hudziak ................ C07K 14/71
424/185.1
6,333,169 B1 * 12/2001 Hudziak ................ C07K 14/71
(Continued)

FOREIGN PATENT DOCUMENTS

CN 1 861 630 11/2006
CN 102838679 12/2012
(Continued)

OTHER PUBLICATIONS

R&D Systems, ErbB2/HER2 Antibody, Catalog # MAB6744, [retrieved online Jun. 1, 2017] URL:<https://www.rndsystems.com/products/mouse-erbb2-her2-antibody-666521_mab6744#product-details>. Rev. Dec. 27, 2016.*
(Continued)

*Primary Examiner* — Claire M Kaufman
(74) *Attorney, Agent, or Firm* — David M. Saravitz; Williams Mullen

(57) ABSTRACT

Protein conjugate comprising a protein antigen for generating an immune response against the HER2/neu protein and an immunogenic carrier covalently bonded to said protein antigen, wherein said protein antigen
(Continued)

(i) has a sequence segment of 300 or more contiguous amino acids of the amino acid sequence of SEQ ID NO: 1; or
(ii) has a variant sequence segment of 300 or more amino acid residues, wherein the amino acid sequence of said variant sequence segment has at least 85% sequence identity to a sequence portion from SEQ ID: 1; or
(iii) has a variant sequence segment of 300 or more amino acid residues and has from 1 to 10 substitutions, deletions or additions in said variant sequence segment compared to a sequence segment of 300 or more amino acid residues of the amino acid sequence of SEQ ID NO: 1 or 2.

12 Claims, 26 Drawing Sheets

(51) Int. Cl.
*C12N 9/12* (2006.01)
*A61K 47/64* (2017.01)
(52) U.S. Cl.
CPC ............ *A61K 2039/55588* (2013.01); *A61K 2039/6037* (2013.01); *C12Y 207/10001* (2013.01)

(56) References Cited

U.S. PATENT DOCUMENTS

| | | | |
|---|---|---|---|
| 7,198,920 B1* | 4/2007 | Cheever | C07K 14/71 |
| 2004/0052811 A1 | 3/2004 | Zielinski et al. | |

FOREIGN PATENT DOCUMENTS

| | | |
|---|---|---|
| WO | 0174855 | 10/2001 |
| WO | 0232450 | 4/2002 |
| WO | 2006036550 | 4/2006 |
| WO | 2008045346 | 4/2008 |
| WO | 2011020604 | 2/2011 |

OTHER PUBLICATIONS

Leone et al., Characterisation of an epitope recognised by a monoclonal antibody against horse alcohol dehydrogenase using peptides synthesised on solid support, FEBS, 335(3):327-330, Dec. 1993.*
Rockberg et al., Discovery of epitopes for targeting the human epidermal growth factor receptor 2 (HER2) with antibodies, Mol. Oncol. 3:238-347 (Year: 2009).*
Simona Rolla et al., Protective Immunity Against neu-Positive Carcinomas Elicited by Electroporation of Plasmids Encoding Decreasing Fragments of Rat Neu Extracellular Domain, Human Gene Therapy, vol. 19, pp. 229-239, Mar. 2008.
Maha Zobra Ladjemi et al., Anti-HER2 vaccines: new prospects for breast cancer therapy, Cancer Immunology and Immunotherapy, vol. 59, pp. 1295-1312, 2010.
Ruth Schwaninger et al., Virosomes as new carrier system for cancer vaccines, Cancer Immunology and Immunotherapy, vol. 53, pp. 1005-1017, 2004.
International Search Report and Written Opinion for PCT/EP2014/000650, EPO, dated May 6, 2014.
European Search Report for 13001211.5, EPO, dated Jul. 17, 2013.
Esserman, L. J. et al., Vaccination with the Extracellular Domain of P185-Neu Prevents Mammary Tumor Development in Neu Transgenic Mice, Cancer Immunology and Immunotherapy, vol. 47, Issue 6. pp. 337-342, Feb. 1, 1999.
Singh, Reshma, et al., "In the FVB/N HER-2/neu Transgenic Mouse both Peripheral and Central Tolerance Limit the Immune Response Targeting HER-2/neu Induced by Listeria monocytogenes-based Vaccines", Cancer Immunol Immunother, vol. 56, pp. 927-938, published online: Nov. 28, 2006.

* cited by examiner

A  SCTLVCPLHNQEVTAEDGTQRCEKCSKPCARVCYGLGMEHLREVRAVTSANIQEF
AGCKKIFGSLAFLPESFDGDPASNTAPLQPEQLQVFETLEEITGYLYISAWPDSL
PDLSVFQNLQVIRGRILHNGAYSLTLQGLGISWLGLRSLRELGSGLALIHHNTHL
CFVHTVPWDQLFRNPHQALLHTANRPEDECVGEGLACHQLCARGHCWGPGPTQCV
NCSQFLRGQECVEECRVLQGLPREYVNARHCLPCHPECQPQNGSVTCFGPEADQC
VACAHYKDPPFCVARCPSGVKPDLSYMPIWKFPDEEGACQPCPINCTHSCVDLDD
KGCPAEQRASPLTS

B  SCTLVCPPNNQEVTAEDGTQRCEKCSKPCARVCYGLGMEHLRGARAITSDNVQEF
DGCKKIFGSLAFLPESFDGDPSSGIAPLRPEQLQVFETLEEITGYLYISAWPDSL
RDLSVFQNLRIIRGRILHDGAYSLTLQGLGIHSLGLRSLRELGSGLALIHRNAHL
CFVHTVPWDQLFRNPHQALLHSGNRPEEDCGLEGLVCNSLCAHGHCWGPGPTQCV
NCSHFLRGQECVEECRVWKGLPREYVSDKRCLPCHPECQPQNSSETCFGSEADQC
AACAHYKDSSSCVARCPSGVKPDLSYMPIWKYPDEEGICQPCPINCTHSCVDLDE
RGCPAEQRASPVTF

Fig. 1

C  TLVCPLHNQEVTAEDGTQRCEKCSKPCARVCYGLGMEHLREVRAVTSANIQEFAG
CKKIFGSLAFLPESFDGDPASNTAPLQPEQLQVFETLEEITGYLYISAWPDSLPD
LSVFQNLQVIRGRILHNGAYSLTLQGLGISWLGLRSLRELGSGLALIHHNTHLCF
VHTVPWDQLFRNPHQALLHTANRPEDECVGEGLACHQLCARGHCWGPGPTQCVNC
SQFLRGQECVEECRVLQGLPREYVNARHCLPCHPECQPQNGSVTCFGPEADQCVA
CAHYKDPPFCVARCPSGVKPDLSYMPIWKFPDEEGACQPCPINCTHSCVDLDDKG
CPAEQRAS

D  RVCYGLGMEHLREVRAVTSANIQEFAGCKKIFGSLAFLPESFDGDPASNTAPLQP
EQLQVFETLEEITGYLYISAWPDSLPDLSVFQNLQVIRGRILHNGAYSLTLQGLG
ISWLGLRSLRELGSGLALIHHNTHLCFVHTVPWDQLFRNPHQALLHTANRPEDEC
VGEGLACHQLCARGHCWGPGPTQCVNCSQFLRGQECVEECRVLQGLPREYVNARH
CLPCHPECQPQNGSVTCFGPEADQCVACAHYKDPPFCVARCPSGVKPDLSYMPIW
KFPDEEGACQPCPINCTHSCVDLDDKGCPAEQRAS

Fig. 1 (cont.)

```
Rat  ED44   314  SCTLVCPPNNQEVTAEDGTQRCEKCSKPCARVCYGLGMEHLRGARAITTSDNVQEFDGCKK     60
                 SCTLVCP +NQEVTAEDGTQRCEKCSKPCARVCYGLGMEHLR  RA+TS N+QEF GCKK
Human ED44  310  SCTLVCPLHNQEVTAEDGTQRCEKCSKPCARVCYGLGMEHLREVRAVTSANIQEFAGCKK    369

Rat  ED44   374  IFGSLAFLPESFDGDPSSGIAPLRPEQLQVFETLEEITGYLYISAWPDSLRDLSVFQNLR    120
                 IFGSLAFLPESFDGDP+S  APL+PEQLQVFETLEEITGYLYISAWPDSL DLSVFQNL+
Human ED44  370  IFGSLAFLPESFDGDPASNTAPLQPEQLQVFETLEEITGYLYISAWPDSLPDLSVFQNLQ    429

Rat  ED44   434  IIRGRILHDGAYSLTLQGLGTHSIGLRSLRELGSGLALIHRNAHLCFVHTVPWDQLFRNP    180
                 +IRGRILH+GAYSLTLQGLGI    LGLRSLRELGSGLALIH  N HLCFVHTVPWDQLFRNP
Human ED44  430  VIRGRILHNGAYSLTLQGLGISWLGLRSLRELGSGLALIHHNTHLCFVHTVPWDQLFRNP    489

Rat  ED44   494  HQALLHSGNRPEEDCGLEGLVCNSLCAHGHCWGPGPTQCVNCSHFLRGQECVEECRVWKG    240
                 HQA+LH+ NRPE++C    EGL C+ LCA GHCWGPGPTQCVNCS FLRGQECVEECRV +G
Human ED44  490  HQALLHTANRPEDECVGEGLACHQLCARGHCWGPGPTQCVNCSQFLRGQECVEECRVLQG    549

Rat  ED44   554  LPREYVSDKRCLPCHPECQPQNSSETCFGSEADQCAACAHYKDSSSCVARCPSGVKPDLS    300
                 LPREYV+ + CLPCHPECQPQN S TCFG EADQC  ACAHYKD   CVARCPSGVKPDLS
Human ED44  550  LPREYVNARHCLPCHPECQPQNGSVTCFGPEADQCVACAHYKDPPFCVARCPSGVKPDLS    609

Rat  ED44   614  YMPIWKYPDEEGICQPCPINCTHSCVDLDERGCPAEQRASPVTF    657
                 YMPIWK+PDEEG  CQPCPINCTHSCVDLD++GCPAEQRASP+T
Human ED44  610  YMPIWKFPDEEGACQPCPINCTHSCVDLDDKGCPAEQRASPLTS    653
```

```
      M   G   K   Q   M   A   A   L   C   G   F   L   L   V   A   L   L   W   L   T   P   D   V   A   S   G   S   C   T   L   V   C   P   .
  1   AATGGGGAA GCAAATGGC CGCCCTGTGT TGGCTTTCT CCTCGTGGC GTTGCTCTG GCTCACGCC CGAGCGTCGC GTCAGGTTC TTGTACTCT GGTATGTCC

. L   H   N   Q   E   V   T   A   E   D   G   T   Q   R   C   E   K   C   S   K   P   C   A   R   V   C   Y   G   L   G   M   E   H   .
 100  ACTACACAA TCAGGAAGT AACCGCTGA GGATGGAAC TCAGAGGTG TGAGAAATG AAGCAAACC CAGTGCTAG AGTTTGCTA TGGTTTGGG AATGGAGCA

. L   R   E   V   R   A   V   T   S   A   N   I   Q   E   F   A   G   C   K   K   I   F   G   S   L   A   F   L   P   E   S   F   D   .
 199  TCTTCGTGA AGTTAGAGC CGGTACGTC AGTTGCCAATAT CCAAGAGTT TGCAGGCTG TAAGAAGAT ATTCGGATC TCTCCCTGA ATCATTCGA

. G   D   P   A   S   N   T   A   P   L   Q   P   E   Q   L   Q   V   F   E   T   L   E   E   I   T   G   Y   L   Y   I   S   A   W   .
 298  TGGTGATCC AGCGTCAAA CACAGCACC ATTACAACC TGGAGCACT CCAAGTGTT TGAGACACT AGAGGAGAT TACGGGGTA TCTCTACAT TCCTGCGTG

. P   D   S   L   P   D   L   S   V   F   Q   N   L   Q   V   I   R   G   R   I   L   H   N   G   A   Y   S   L   T   L   Q   G   L   .
 397  GCCTGACTC CTTGCCAGA TCTTCAGT GTTCAGAA CTTGCAAGT GATTCGTGG TAGGATACT TCACAACGG TAGCTATAG CCTCACATT ACAAGGGTT

. G   I   S   W   L   C   L   R   S   L   R   E   I   G   S   G   L   A   L   I   H   H   N   T   H   L   C   F   V   H   T   V   P   .
 496  GGGCATTTC ATGGCTAGG GTTACGAGG TCTTAGAGA ACTTGGTTC GGATTGGC ACTTATCC ACTTATCCA ACTTATCA CCATTGTG CTTTGTGCA CACAGTACC

. N   D   Q   L   F   R   N   P   H   Q   A   L   L   H   T   A   N   R   P   E   D   E   C   V   G   E   G   L   A   C   H   Q   L   .
 595  ATGGGATCA GTTGTTCAG AAATCCTCA GCTGCATAC AGCTAATCG TCCAGAAGA TGAGTGTGT CGGAGAAGG TCTAGCATG TCACCAGTT

. C   A   R   G   H   C   W   G   P   G   P   T   Q   C   V   N   C   S   Q   F   L   R   G   Q   E   C   V   E   E   C   R   V   L   .
 694  ATGCGCTAG AGGCCATTG TTGGGGACC TGGACCAAC TCAGTGCGT TAATTGCAG TCAGTTCCT CAGGGGTCA GGAATGTGT CGAAGAATG CAGGGTTTT

. Q   G   L   P   R   E   Y   V   N   A   R   H   C   L   P   C   H   P   E   C   Q   P   Q   N   G   S   V   T   C   F   G   P   E   .
 793  ACAAGGGCT TCCTAGAGA ATACGTGAA TGCGCGACA TTGCCTGCC TTGTCATCC AGAATGTCA ACCCCAAAA TGGTTCCGT TACTTGTTT TGGCCCAGA

. A   D   Q   C   V   A   C   A   H   Y   K   D   P   P   F   C   V   A   R   C   P   S   G   V   K   P   D   L   S   Y   M   P   I   .
 892  GGCTGATCA GTGCGTTGC ATGCGCACA CTACAAGGA TCCACCTTT CTGTGTGC AAGCGGAGT CAGATGTCC AAGCCAGA CCTTTCCTA TATGCCCAT

. W   K   F   P   D   E   E   G   A   C   Q   P   C   P   I   N   C   T   H   S   C   V   D   L   D   D   K   G   C   P   A   E   Q   .
 991  TTGGAAATT TCCCGATGA AGAGGGAGC TTGCCAACC TGTCCAACT AAACTGCAC TCATAGTTG CGTCGATT GGACGACAA AGGTTGTCC AGCTGAACA

. R   A   S   P   L   T   S   G   S   A   A   A   H   H   H   H   H   H   *
1090  AAGAGCTTC TCCGCTTAC ATCAGTGA ATCAGCGGC CGCCCATCA TCATCATCA TCATTGAGC TT
```

HER2/NEU CANCER VACCINE

CROSS-REFERENCE TO RELATED APPLICATIONS

This application is the U.S. National Stage of International Application PCT/EP2014/000650, filed Mar. 11, 2014, which designates the U.S and was published by the International Bureau in English on Sep. 18, 2014, and which claims the benefit of European Patent Application No. 13 001 211.5, filed Mar. 11, 2013; all of which are hereby incorporated herein in their entirety by reference.

FIELD OF THE INVENTION

The present invention relates to protein conjugate comprising a protein antigen from the extracellular domain of Her2/Neu or a protein antigen having a high sequence identity or similarity to a certain portion of the extracellular domain of Her2/Neu. The invention also relates to the protein antigen. The protein conjugate comprises the protein antigen, and, covalently bonded to the protein antigen, an immunogenic carrier. The protein conjugate or the protein antigen can be used as a cancer vaccine for Her2/Neu positive cancers. The invention further provides a cancer vaccine against Her2/Neu positive cancers. The cancer vaccine contains the protein conjugate or the protein antigen and suitable adjuvants and/or pharmaceutically acceptable excipients. The invention also provides a method of preventing and/or treating Her2/neu positive cancers using the cancer vaccine. Further provided is a process of producing the protein conjugate. Further, the invention relates to a nucleic acid encoding the protein antigen, and a kit for producing the protein conjugate.

BACKGROUND OF THE INVENTION

Human Epidermal Growth Factor Receptor Her2, also known as Neu, ErbB-2, or p185, is a member of the epidermal growth factor receptor (EGFR/ErbB) family and encoded by the ERBB2 gene. Herein, the terms "HER2" or "Her2" and "Her2/neu" are used interchangeably. As other members of ErbB family, Her2 is a membrane-bound receptor tyrosine kinases composed of extracellular ligand binding domain, a transmembrane domain, and an intracellular domain that can interact with downstream signaling molecules. Unlike the other family members, HER2 is considered to be an orphan receptor as it has no known ligand. HER2 can heterodimerise with other ErbB family receptors and is considered to be their preferred dimerisation partner. Dimerisation results in the autophosphorylation of tyrosine residues within the cytoplasmic domain of the receptors and initiates a variety of signaling pathways leading to proliferation and inhibition of apoptosis.

Amplification of the ERBB2 gene occurs in 20-30% of human breast and ovarian cancers and is linked to a more aggressive disease course and worse prognosis (Bange, J., Zwick E. & Ullrich A., 2001, *Nature Medicine*, 7: 548-552; Slamon, D. J., Clark, G. M., Wong, S. G. et al., 1987' *Science*, 235:177-182; Slamon, D. J., Godolphin, W., Jones, L. A. et al., 1989, *Science*, 244:707-712; Berchuck, A., Kamel, A., Whitaker. R., et al., 1990, *Cancer Research* 50:4087-4091). In ERBB2$^+$ tumor cells, the receptor can function on its own and/or it needs to heterodimerize with another ErbB member to transduce a deregulated proliferative signal responsible for the neoplastic behavior of the cells.

In recent years HER2 has evolved as an important target for therapy of breast cancer in particular by monoclonal antibody therapy, e.g. Herceptin (trastuzumab) a humanized monoclonal antibody against this surface target has been approved by FDA in 1998. *Herceptin has a significant impact on survival rates of HER2* positive breast cancer patients (Tan, A. R. & Swain, S. M., 2002, *Seminars in Oncology*, 30: 54-64). Although active against HER2 homodimers, trastuzumab is not effective against ligand-induced HER2 heterodimers (Agus, D. B., Akita, R. W, Fox, W. D., et al., 2002, *Cancer Cell*, 2:127-137; Cho, H. S., Mason, K., Ramyar, K. X., et al., 2003, *Nature*, 421:756-60). In addition, cancers usually develop resistance to trastuzumab (Cho, H. S., Mason, K., Ramyar, K. X., et al., 2003, *Nature*, 421:756-760). While trastuzumab is efficient for the treatment of late stage metastatic cancers, it is not clear if it is effective in earlier stage cancers (Editorial, 2005, *Lancet*, 366:1673).

In Jun. 2012, the FDA approved yet another monoclonal antibody pertuzumab (U.S. Pat. Nos. 7,449,184; 7,981,418) for treatment of HER2/neu positive metastatic breast cancer in combination with Herceptin® (trastuzumab) and docetaxel chemotherapy for patients who have not received prior anti-HER2 therapy or chemotherapy for metastatic disease (Genentech press release on 8 Jun., 2012, available on the World Wide Web at: gene.com/gene/news/press-releases/display.do?method=detail&id=14007). This approach allowed extending patient's cancer progression-free period for median 6.1 months.

As an alternative or complementation to HER2/neu-positive cancers treatment with therapeutic antibodies, different cancer vaccines are currently under testing. This approach provides the most dramatic shift in cancer treatment, as patient's own immune system could be trained to recognise and delete HER2-positive cancer cells. Different vaccine designs (simple peptides, DNA encoding HER2 regions, HER2 protein fragments and whole-cell vaccines) have been tested in human clinical trials that have shown that significant levels of durable humoral or T-cell HER2 immunity can be generated with active immunization (Ladjemi, M. Z., Jacot, W., Charde's, T. et al., 2010, *Cancer Immunol. Immunother.*, 59:1295-1312). The most advanced clinical studies are with peptide-based vaccines, especially the one based on E75 peptide (Disis, M. L., & K Schiffman, K., 2001, *Semin Oncol.*, 28:12-20; Murray, J. L., Gillogly, M. E., Przepiorka, D. et al., 2002, *Clin Cancer Res.*, 8:3407-3418; Peoples, G. E., Gurney, J. M., Hueman, M. T., et al., 2005, *J Clin Oncol* 23:7536-7545; Ross, J. S., Slodkowska, E. A., Symmans, W. F., et al., 2009, *The Oncologist*, 14:320-368; U.S. Pat. No. 8,222,214; for review see Ladjemi, M Z., Jacot, W., Chardes, T. et al., 2010, *Cancer Immunol. Immunother.*, 59:1295-1312). This vaccination can break tolerance against endogenous HER2 receptor. The key component of the vaccine is peptide E75, a peptide of 9-amino acid residues (U.S. Pat. No. 8,222,214; Mittendorf, E. A., Clifton, G. T., Holmes, J. P. et al., 2012, *Cancer*, 118:2594-602). Cancer vaccines do not usually cause toxicities typically associated with the use of therapeutic antibodies or chemotherapeutics (e.g. Peoples, G. E., Gurney, J. M., Hueman, M. T., et at., 2005, *J. Clin. Oncol.*, 23:7536-7545; Ross, J. S., Slodkowska, E. A., Symmans, W. F., et al., 2009, *The Oncologist*, 14:320-368; Dabney, R. S., Hale, D. F., Vreeland, T. J., et al., 2012, *J. Clin. Oncol*, 30 (ASCO suppl; abstr 2529); Hamilton, E., Blackwell, K., Hobeika, A. C., et al., 2012, *J. Transl. Med.*, 10:28).

Also, no significant toxic autoimmunity directed against normal tissues has been encountered with vaccines (Bernhard, H., Salazar, L., Schiffman, K. et al., 2002, *Endocr Re/at Cancer* 9:33-44; Ladjemi, M. Z., Jacot, W., Charde's, T. et al., 2010, *Cancer Immunol. Immunother.*, 59:1295-1312). Most of these vaccines focus on T-cell immunity and consist of peptides or mixes of a small number of epitopes, necessitating patient cohorts to be HLA-matched at enrollment, and consequently exhibit a narrow immune response (Ladjemi, M. Z., Jacot, W., Charde's, T. et al., 2010, *Cancer Immunol. Immunother.*, 59:1295-1312).

In addition to a narrow spectrum of target sites for peptide vaccines, use of peptide-based vaccines might suffer from difficulties in identification of the most promising peptides. Peptide vaccines cause immune response limited to one or few peptides in the composition. A promising alternative are DNA vaccines that are easy to manufacture but, while they are superior to peptides in inducing CD8+T-cell responses (Chaise, C., Buchan, S. L., Rice, J. et al., 2008, *Blood*, 112:2956-2964; Rolla, S., Marchini, C., Malinarich, S. et al., 2008, *Human Gene Therapy*, 19:229-239; U.S. Pat. No. 8,207,141), they are typically less effective than protein vaccines in inducing antibody responses.

Clinical trials with HER2 protein-based vaccines were also carried out. In one case, the HER2 ICD (intra-cellular domain, aa 676-1255) was used as an adjuvant vaccine (Disis, M.L., Schiffman, K., Guthrie, K. et al., 2004, *J. Clin. Oncol.*, 22:1916-1925). It was shown that the vaccine was well tolerated and the patients treated with the highest dose more rapidly developed immunity. No therapeutic effect was reported. Phase I clinical trials with dHER2 consisting of the complete extracellular domain (ECD) and a portion of the intracellular domain (ICD) in combination with a complex mix of adjuvants and the tyrosine kinase inhibitor Lapatinib showed no (cardio) toxic effect, but also showed weak T-cell responses and 55 days median time to progression (Hamilton, E., Blackwell, K., Hobeika, A. C. et al., 2012, *J. Trans. Med.*, 10:28, available on the World Wide Web at: translational-medicine .com/content/10/1/28. Use of a portion of a HER2 ECD domain (aa 1-146) complexed with cholesteryl pullulan nanogels (CHP-HER2) was well tolerated by patients and induced T-cell responses to the truncated HER2 protein (Kitano, S., Kageyama, S., Nagata, Y. et al., 2006, *Clin. Cancer. Res.*, 12:7397-7405). However, second trials with the same antigen showed that induced Abs (antibodies) did not recognize the HER2 antigen expressed in its native form at the surface of cancer cells (Kageyama, S., Kitano, S., Hirayama, M. et al., 2008, *Cancer Sci.*, 99:601-6070). Combination of CHP-HER2 with yet another tumor-specific antigen, NY-ESO-1, did not lead to the improved immune responses. On contrary, there were weaker antibody responses to HER2 in the combination vaccine compared to CHP-HER2 alone (Aoki, M., Ueda, S., Nishikawa, H. et al., 2009, *Vaccine*, 27:6854-6861).

In summary, existing vaccines under development suffer from several limitations (Ladjemi, M. Z., Jacot, W., Charde's, T. et al., 2010, *Cancer Immunol. Immunother.*, 59:1295-1312): whole tumor cell vaccines must be made individually, the (an) immune response difficult to monitor and there is a risk of auto-immunity induction in the presence of adjuvant; DNA vaccines carry a risk of potentially promoting the malignancy due to DNA integration into the cell genome; peptide vaccines generate immune response limited to one or few epitopes, can be degraded in the absence of adjuvant, have restricted HLA population; HER2 protein-based vaccines up to now have not shown significant therapeutic effect.

Esserman et al., *Cancer Immunol. Immunother* (1999) 47: 337-342 relates to vaccination of neu transgenic mice with the extracellular domain (ECD) of HER2. The authors report that immunization with the Neu ECD delayed the onset of tumor growth. However, the authors also report that once tumors began to grow, they appeared to do so at the same rate as those in the control immunized mice, i.e. without the Neu ECD antigen.

Schwaninger et al., *Cancer Immunol. Immunother* (2004) 53: 1005-1017 describe virosomes as a carrier system for Her2/neu cancer vaccines. Mice vaccinated with the extracellular domain (ECD) of the Her2/neu protein bound to virosomes generated a humoral and cytotoxic immune response. However, once tumors were formed in their mouse model, vaccination had no influence on tumor progression, i.e. had no therapeutic effect.

Therefore, it is an object of this invention to provide a protein conjugate suitable as a cancer vaccine for HER2/neu positive cancer. It is another object to provide a protein antigen and a protein conjugate that has a therapeutic effect on HER2 positive cancer. It is another object to provide a protein conjugate or cancer vaccine capable to eliciting a long-term T-cell dependent immune response. It is another object to provide a method of treating HER2/neu positive cancer using a vaccine that is capable of inducing strong protective humoral and cellular immune responses. It is another object of this invention to provide a formulation of said vaccine.

SUMMARY OF THE INVENTION

These objects are achieved by:
(1) Protein conjugate comprising a protein antigen and an immunogenic carrier covalently bonded to said protein antigen, wherein said protein antigen
   (i) has a sequence segment of 300 or more contiguous amino acids of the amino acid sequence of SEQ ID NO: 1; or
   (ii) has a variant sequence segment of 300 or more amino acid residues, wherein the amino acid sequence of said variant sequence segment has at least 85% sequence identity to a sequence portion from SEQ ID: 1; or
   (iii) has a variant sequence segment of 300 or more amino acid residues and has from 1 to 20 substitutions, deletions or additions in said variant sequence segment compared to a sequence segment of 300 or more amino acid residues of the amino acid sequence of SEQ ID NO: 1 or 2.
(2) The protein conjugate according to item 1, wherein
   said protein antigen has a sequence segment of 300 or more contiguous amino acid residues of the amino acid sequence of SEQ ID NO: 2, or
   said protein antigen has a variant sequence segment of 300 or more amino acid residues, wherein the amino acid sequence of said variant sequence segment has at least 85% sequence identity to a sequence portion from SEQ ID: 2.
(3) The protein conjugate according to item 1 or 2, wherein said protein antigen has, in said sequence segment or said variant sequence segment, at most 500, preferably at most 400, contiguous amino acid residues from SEQ ID NO: 1 or 2.
(4) The protein conjugate according to item 2, wherein said sequence segment consists of the amino acid sequence of SEQ ID NO: 2, 4 or 5, preferably said protein antigen consists of the amino acid sequence of SEQ ID NO: 2, 4 or 5 and optionally a purification tag.
(5) The protein conjugate according to any one of items 1 to 4, wherein said protein antigen comprises, as a further segment, a purification tag at its N- or C-terminal end, such as a 6×-His tag or a constant region of an antibody light chain, and optionally a linker linking the purification tag and the sequence segment of the protein antigen, preferably said protein antigen consists of said sequence segment or variant sequence segment, said purification tag and optionally said linker (6) The protein conjugate according to any one of items 1 to 5, wherein said immunogenic carrier is or comprises an immunogenic protein or an immunogenic protein aggregate.

(7) The protein conjugate according to item 6, wherein said immunogenic protein is or comprises tetanus toxin fragment C or the DOM1 fragment thereof.

(8) The protein conjugate according to item 6, wherein said protein aggregate is or comprises a viral particle, such as a plant viral particle.

(9) The protein conjugate according to any one of items 1 to 8, wherein said variant further has from 1 to 10 deletions or additions in said variant sequence segment compared to said amino acid sequence of SEQ ID NO: 1 or 2.

(10) The protein conjugate according to any one of items 1 to 8, wherein said variant has from 1 to 10 substitutions, deletions or additions in said sequence segment compared to said amino acid sequence of SEQ ID NO: 1 or 2.

(11) Anti-cancer vaccine comprising the protein conjugate of any one of items 1 to 10 or the protein antigen defined therein.

(12) The anti-cancer vaccine according to item 11, further comprising water in which said protein conjugate is dispersed and, optionally, further pharmaceutically acceptable excipients.

(13) The anti-cancer vaccine according to item 11 or 12, further comprising an immunological adjuvant.

(14) The protein conjugate as defined in any one of items 1 to 10 for use in a method of treating a HER-2/Neu-positive cancer.

(15) A method of treating a HER-2/Neu-positive cancer in a patient suffering from such cancer, comprising administering the protein antigen of the invention or, preferably, the protein conjugate of the invention or the to a patient suffering from said cancer one to several times.

(16) A process of producing the protein conjugate of the invention, comprising expressing said protein antigen or said variant in eukaryotic cells of a plant, purifying said protein antigen or said variant, and cross-linking the purified protein antigen or said variant with said carrier.

(17) Protein antigen having a sequence segment of 300 or more contiguous amino acids of the amino acid sequence of SEQ ID NO: 1, or a protein antigen having a variant sequence segment of 300 or more amino acid residues, wherein the amino acid sequence of said variant sequence segment has at least 85% sequence identity to a sequence portion from SEQ ID: 1.

(18) Protein antigen consisting of a first amino acid sequence segment having amino acid sequence similarity to that of the Her2/neu protein, and optionally one or more further amino acid sequence segments; wherein said first sequence segment
(i) has an amino acid sequence of 300 or more contiguous amino acids of the amino acid sequence of SEQ ID NO: 2; or
(ii) has a variant amino acids sequence of 300 or more amino acid residues, wherein the amino acid sequence of said variant sequence segment has at least 85% sequence identity to a sequence portion from SEQ ID: 2; or
(iii) has a variant amino acid sequence of 300 or more amino acid residues and has from 1 to 20 substitutions, deletions or additions in said variant sequence compared to a sequence segment of 300 or more amino acid residues of the amino acid sequence of SEQ ID NO: 2;
and any further amino acid sequence segment of 20 or more, preferably 10 or more, contiguous amino acids does not contain a sequence portion from amino acids 1 to 253, preferably 1 to 283, more preferably 1 to 300, nor from a sequence portion starting from amino acid 670, preferably from amino acid 654, of SEQ ID NO: 18; or any further amino acid sequence segment of more than 20 contiguous amino acids does not have more than 50% sequence identity to a sequence portion from amino acids 1 to 253, preferably 1 to 283, more preferably 1 to 300, nor to a sequence portion starting from amino acid 670, preferably from amino acid 654 of SEQ ID NO: 18; and a protein conjugate comprising such protein antigen.

(19) A nucleic acid sequence encoding the protein antigen of item 17 or 18.

(20) Kit comprising the protein antigen as defined in any one of items 1 to 10 and an immunogenic protein or protein aggregate for cross-linking with said protein antigen.

The cancer vaccines of the invention have the ability to induce a broad polyclonal antibodies response to human HER2 ECD, plus to recruit foreign T-cell help to enhance the humoral response via conjugation to a carrier such as tetanus Fragment C or plant RNA virus particles. The present invention not only provides preventive effects for cancer development, but also therapeutic effects by vaccination when tumors have already developed. No such therapeutic effects were achieved in the prior art.

BRIEF DESCRIPTION OF THE FIGURES

FIG. 1: Amino acid sequence of Her2-ED44.
A) Amino acid sequence of the human Her2-ED44 (SEQ ID NO: 2) which encompasses residues 310-653 of the human HER2/neu protein (GenBank accession no.: AAA75493). Residues removed in shorter Her2-ED44 versions are bold (for version in C) or underlined (for version in D).
B) Amino acid sequence of the rat Her2-ED44 (SEQ ID NO: 3) which encompasses residues 314-657 of the rat HER2/neu protein (GenBank accession no.: NP_058699).
C) Shortened version of Her2-ED44 (SEQ ID NO: 4) which encompasses residues 312-649 of the human HER2/neu protein.
D) Shortened version of Her2-ED44 (SEQ ID NO: 5) which encompasses residues 340-649 of the human HER2/neu protein.

FIG. 2: Alignment of the rat (SEQ ID NO: 3) and human (SEQ ID NO: 2) Her2-ED44 amino acid sequences.
The rat Her2-ED44 (Rat ED44) is shown in italics and the human Her2-ED44 (Human ED44) in bold. The sequences were aligned using BLASTP. Identical amino acid residues are shown between both sequences and similar residues according to the BLOSUM62 matrix are indicated with a "+". The two sequences exhibits 86% identity and 91% similarity.

FIG. 3: Schematic representation of the building blocks of Her2-ED44 and Tetanus toxin fragment C and the structure of the vaccine.
Vaccine designs comprising (A) His-tagged Her2-ED44, (B) Her2-ED44 and Tetanus toxin fragment C (immunogenic carrier) fusion proteins which also contain a linker region and the human kappa constant region, or (C) Her2-

ED44 fusion protein which contains a linker and the human kappa constant region conjugated to Tobacco Mosaic Virus particles (immunogenic carrier). Vaccines or protein antigens with two components, i.e. Her2-ED44 and Tetanus toxin fragment C or Tobacco Mosic Virus particles are cross-linked using glutardialdehyde. The coat protein of the Tobacco Mosaic Virus was modified by introducing a lysine residue into its N-terminal region to allow more efficient cross-linking.

Figure 4:
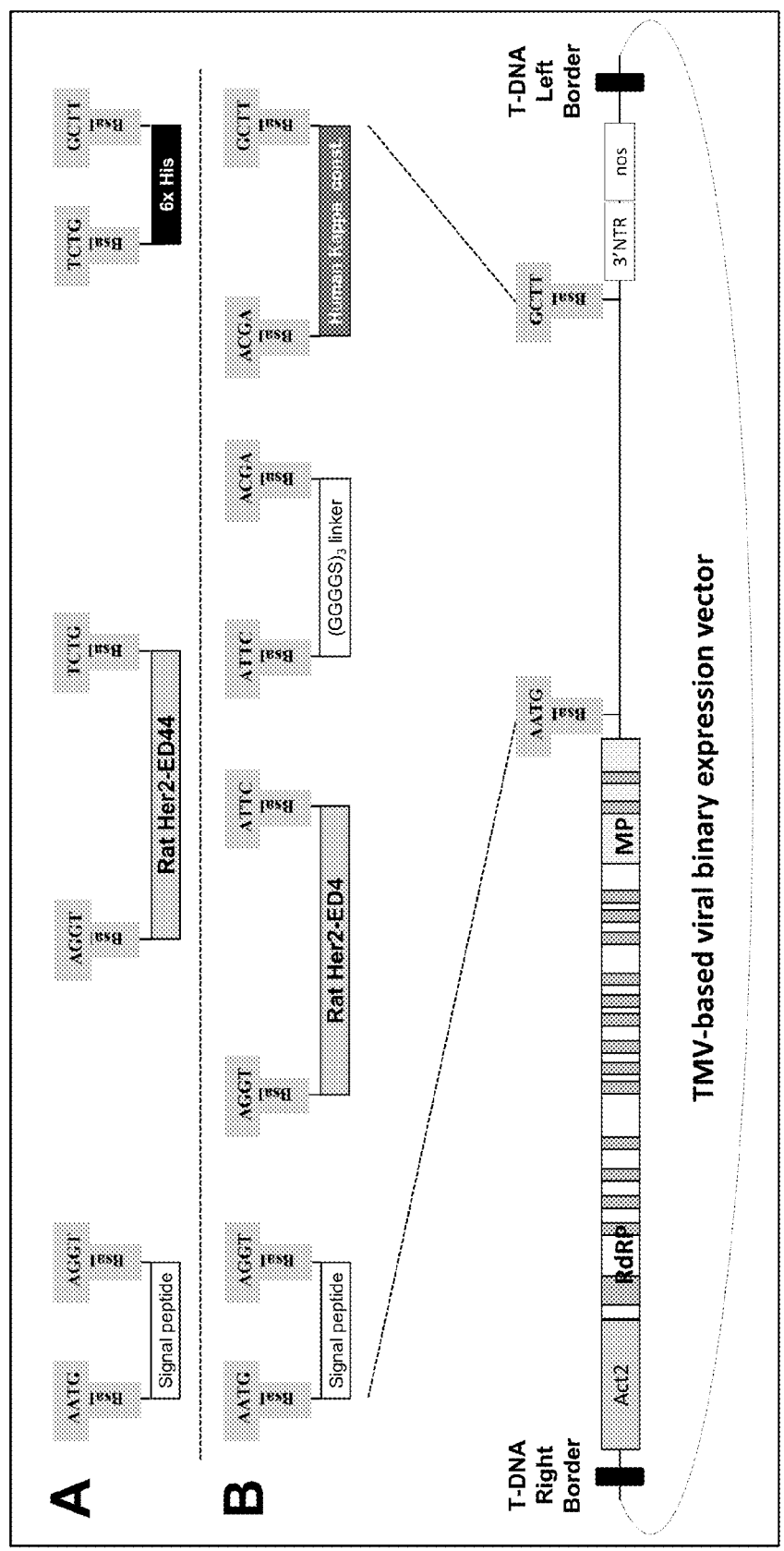

FIG. 4: Cloning schemes for rat Her2-ED44 constructs.

Cloning schemes for rat Her2-ED44 constructs with (A) His-tag and (B) fusion to the human kappa constant region. Sequence modules for signal peptide, rat Her2-ED44 and the 6×His-tag or the (GGGGS)₃ linker and the human kappa constant region are cloned in a TMV-based viral binary expression vector using the Type IIS enzyme BsaI. Overhangs flanking the modules after BsaI restriction digest are shown.

FIG. 5: Sequence of the rat Her2-ED44-His construct (SEQ ID NO: 6) and amino acid sequence (SEQ ID NO: 7). Sequence of the rice α-amylase signal peptide (bold, italic), the rat Her2-ED44 and the 6×His-tag (bold, italic) are shown. Overhang sequences used for BsaI cloning are shown in bold and underlined. After cloning in the TMV-based viral binary expression vector BsaI recognition sites are no longer present.

Figure 6:
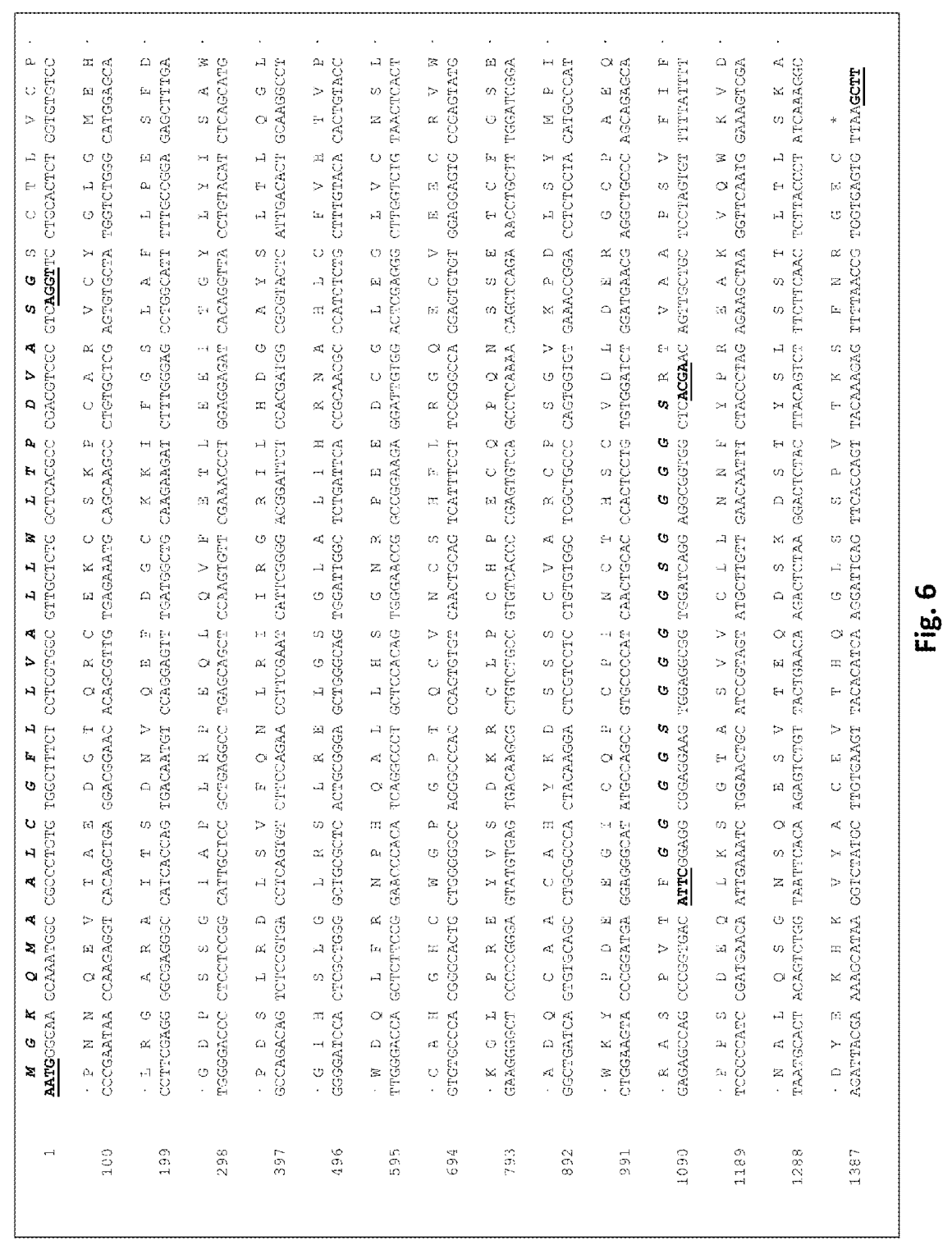

FIG. 6: Sequence of the rat Her2-ED44-kappa construct (SEQ ID NO: 8) and amino acid sequence (SEQ ID NO: 9). Sequence of the rice α-amylase signal peptide (bold, italic), the rat Her2-ED44, the (GGGGS)₃ linker (bold, italic) and the human kappa constant region. Overhang sequences used for BsaI cloning are shown in bold and underlined. After cloning in the TMV-based viral binary expression vector BsaI recognition sites are no longer present.

Figure 7:
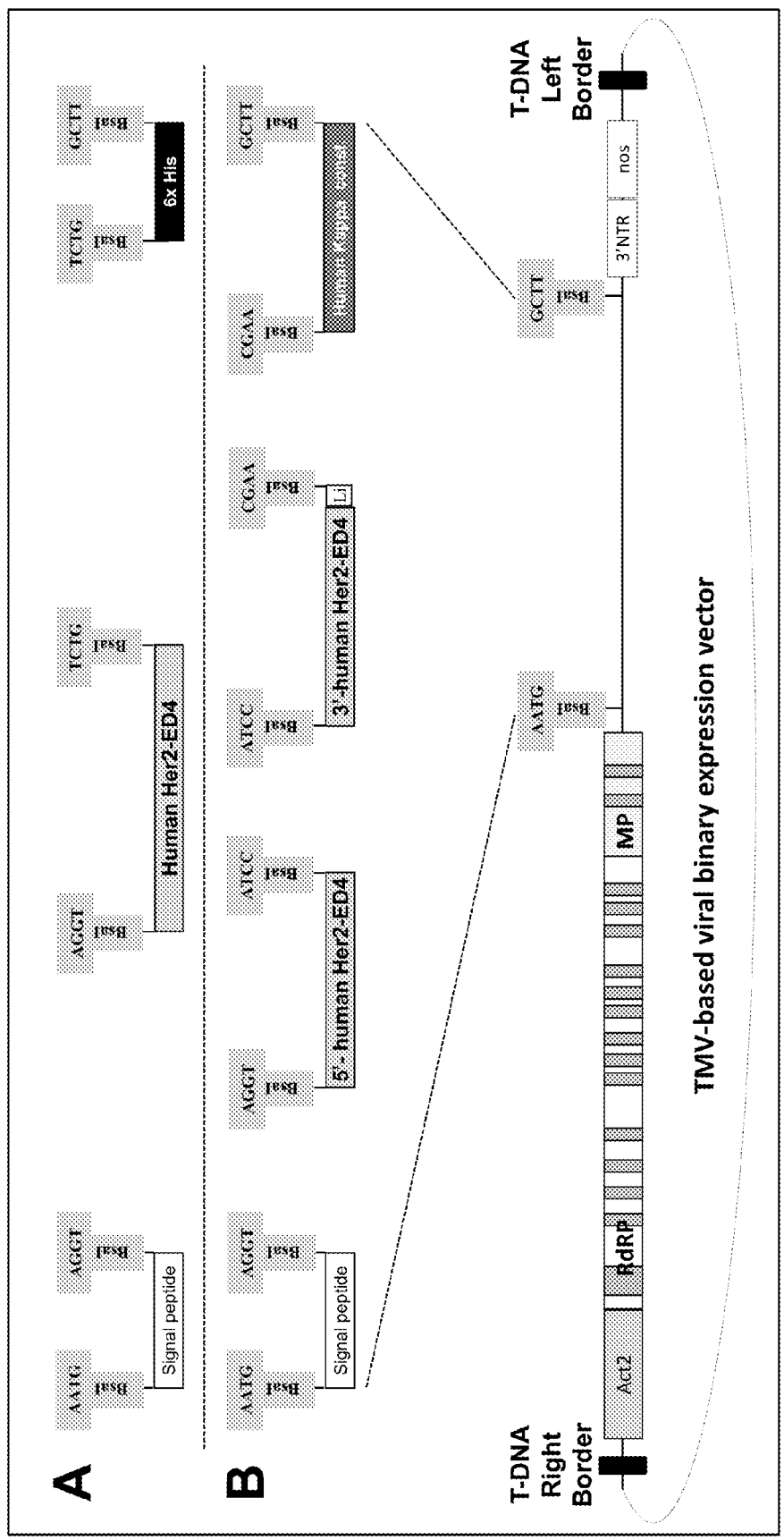

FIG. 7: Cloning schemes for human Her2-ED44 constructs. Cloning schemes for human Her2-ED44 constructs with (A) His-tag and (B) fusion to the human kappa constant region. Sequence modules for signal peptide, rat Her2-ED44 and the 6×His-tag or the (GGGGS)₃ linker and the human kappa constant region are cloned in a TMV-based viral binary expression vector using the Type IIS enzyme BsaI. Overhangs flanking the modules after BsaI restriction digestion are shown.

FIG. 8: Sequence of the human Her2-ED44-His construct (SEQ ID NO: 10) and amino acid sequence (SEQ ID NO: 11). Sequence of the rice α-amylase signal peptide (bold, italic), the human Her2-ED44 and the 6×His-tag (bold, italic). Overhang sequences used for BsaI cloning are shown in bold and underlined. After cloning in the TMV-based viral binary expression vector BsaI recognition sites are no longer present.

Figure 9:
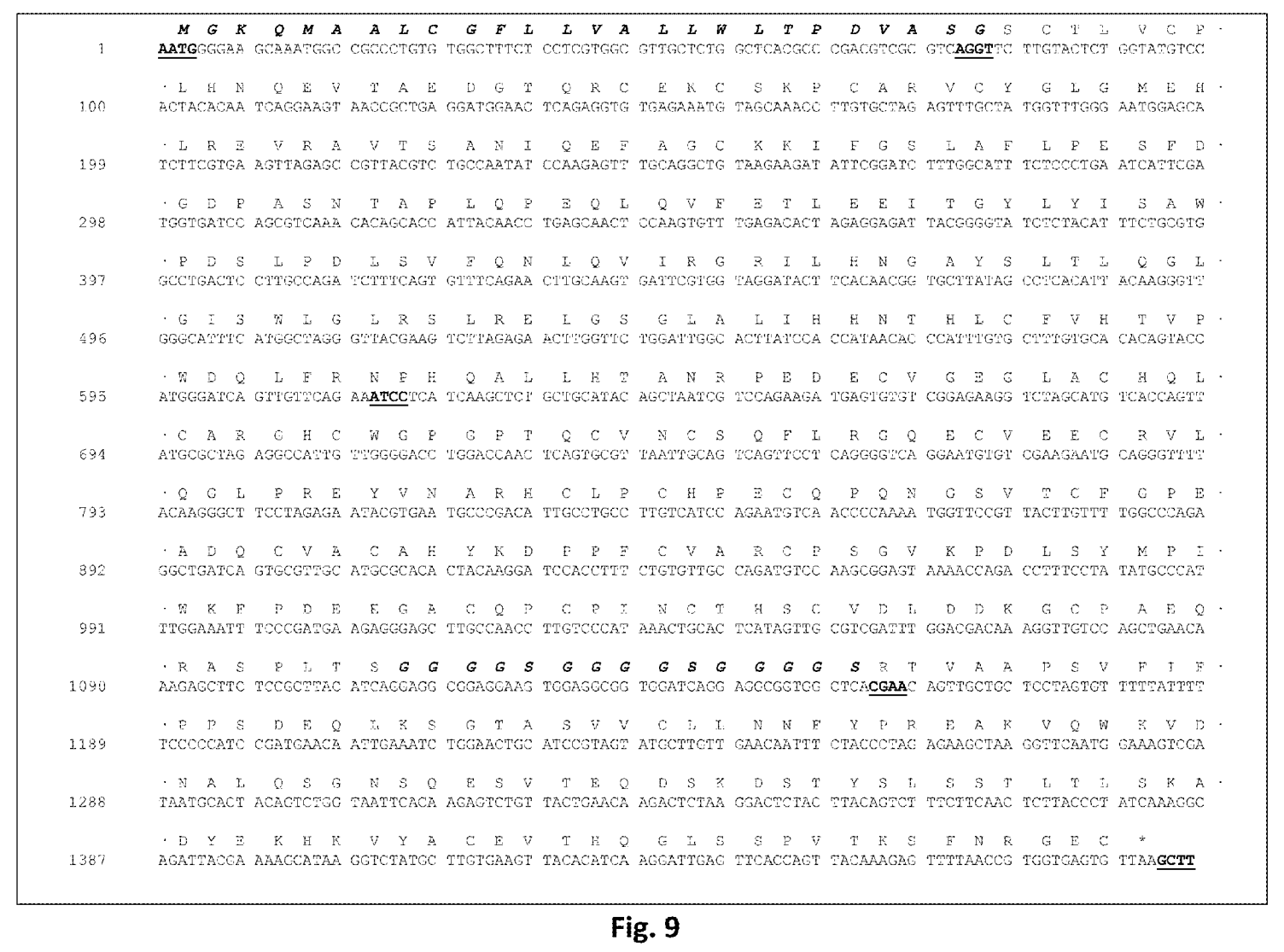

FIG. 9: Sequence of the human Her2-ED44-kappa construct (SEQ ID NO: 12) and amino acid sequence (SEQ ID NO: 13). Sequence of the rice α-amylase signal peptide (bold, italic), the human Her2-ED44, the (GGGGS)₃ linker (bold, italic) and the human kappa constant region. Overhang sequences used for BsaI cloning are shown in bold and underlined. After cloning in the TMV-based viral binary expression vector BsaI recognition sites are no longer present.

Figure 10:
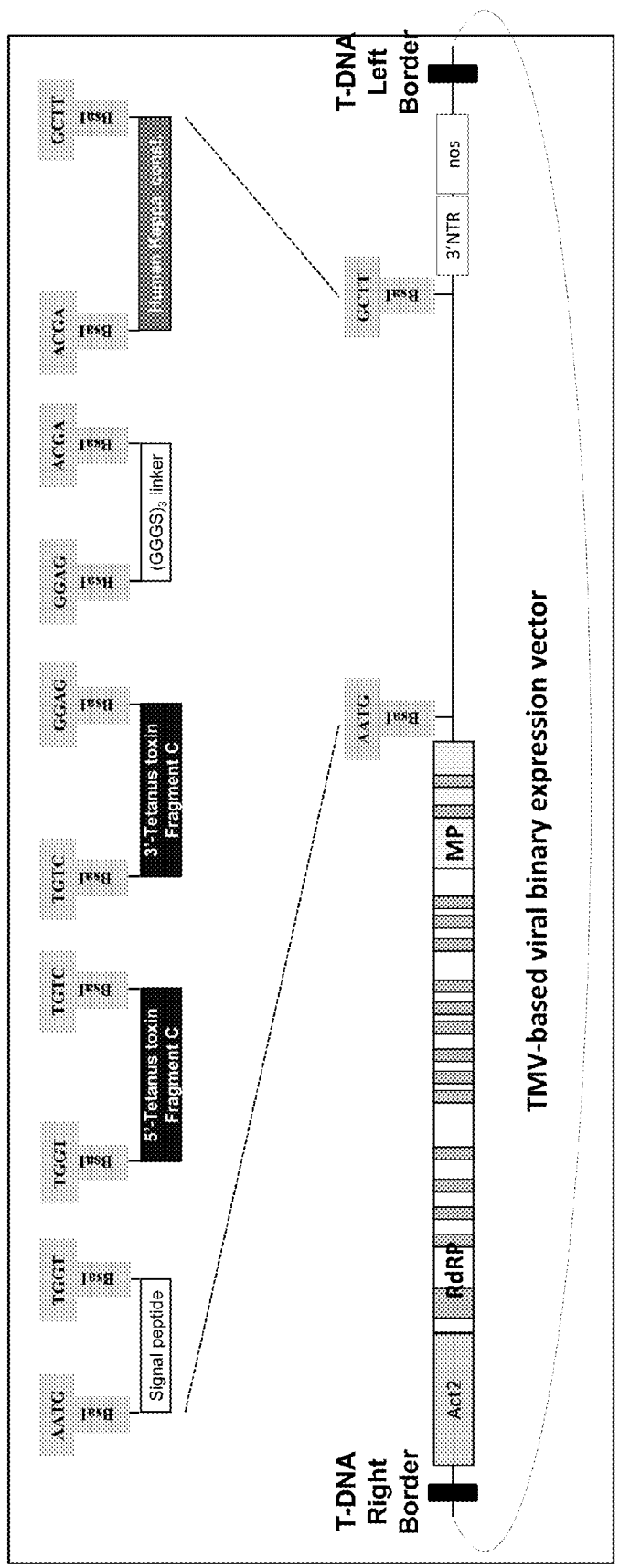

FIG. 10: Cloning scheme for Tetanus toxin fragment C construct. Cloning scheme for Tetanus toxin fragment C fusion to the human kappa constant region is shown. Sequence modules for signal peptide, Tetanus toxin fragment C, the (GGGGS)₃ linker and the human kappa constant region are cloned in a TMV-based viral binary expression vector using the Type IIS enzyme BsaI. Overhangs flanking the modules after BsaI restriction digestion are shown.

Figure 11:
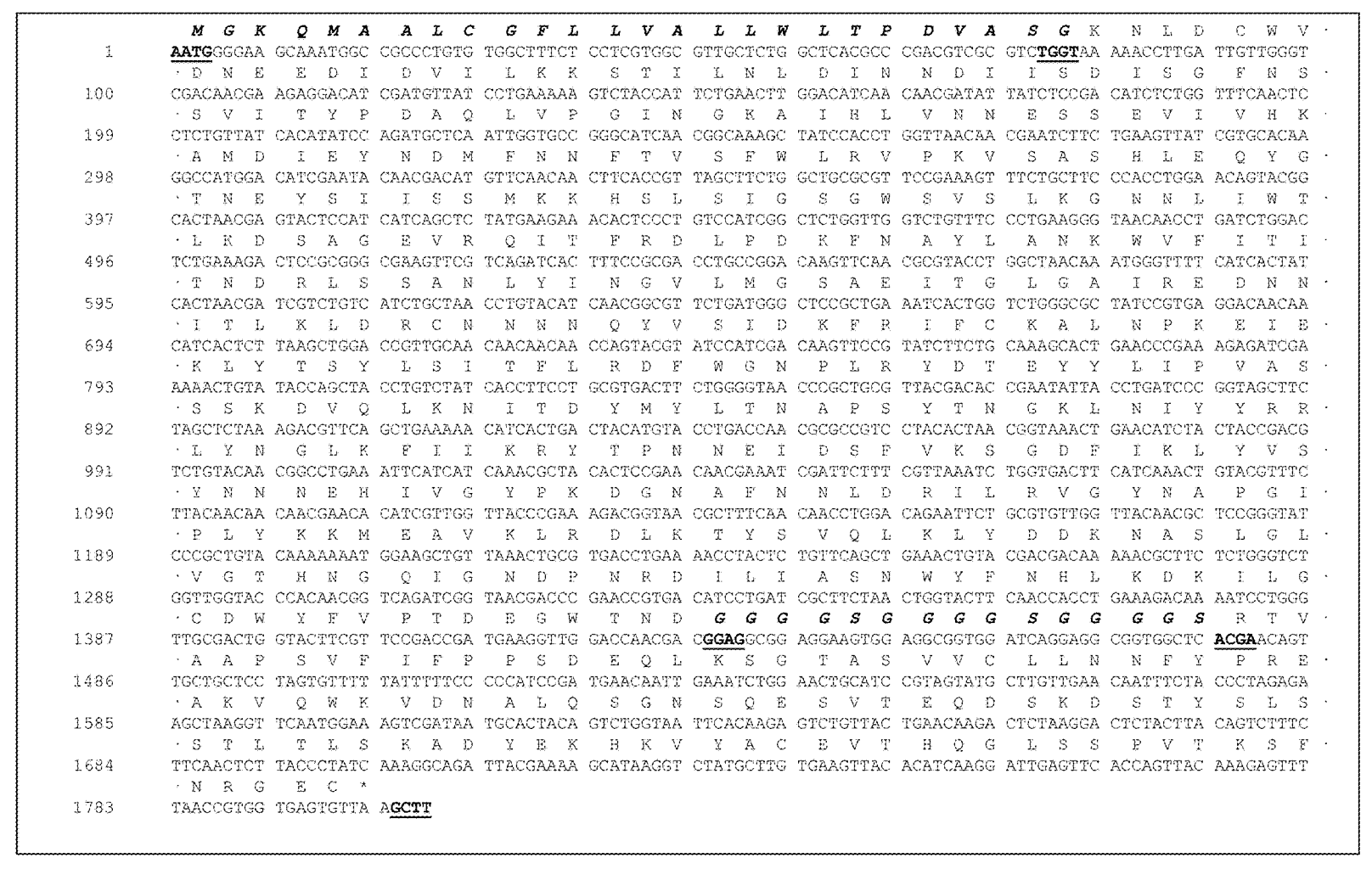

FIG. 11: Sequence of the Tetanus toxin fragment C-kappa construct (SEQ ID NO: 14) and amino acid sequence (SEQ ID NO: 15). Sequence of the rice α-amylase signal peptide (bold, italic), the Tetanus toxin fragment C, the (GGGGS)₃ linker (bold, italic) and the human kappa constant region. Overhang sequences used for BsaI cloning are shown in bold and underlined. After cloning in the TMV-based viral binary expression vector BsaI recognition sites are no longer present.

Figure 12:
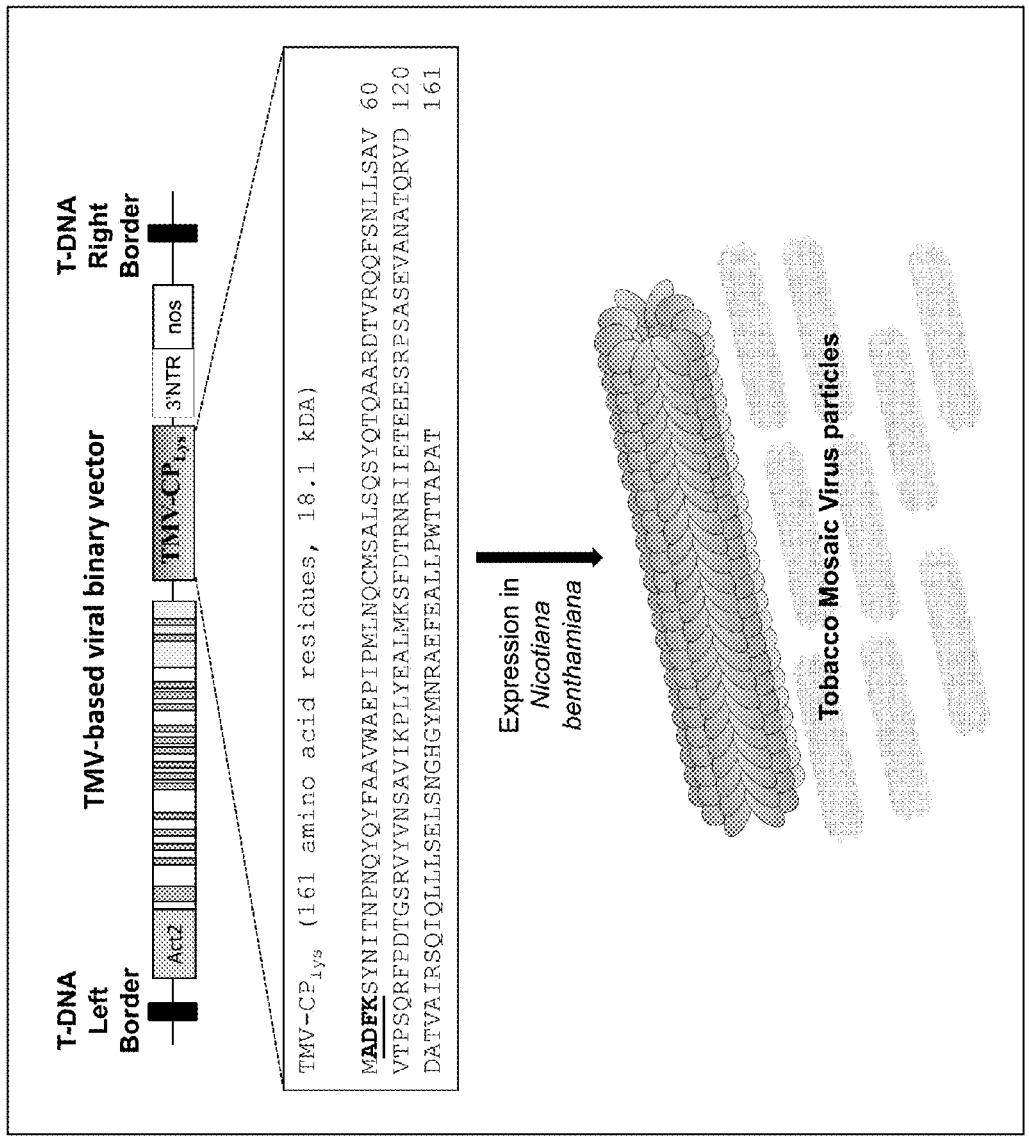

FIG. 12: TMV-CPLys containing Tobacco Mosaic Virus particles. Schematic representation of the TMV-based vector for production of TMV-CPLys containing tobacco mosaic virus particles. The sequence of CPLys is shown (SEQ ID NO: 16) (accession number for wild-type CP: Q88922) and the extension at the N-terminus containing the lysine residue (ADFK) is indicated in bold and underlined. Expression of this viral construct in *Nicotiana benthamiana* leads to the formation of CPLys containing Tobacco Mosaic Virus particles.

Figure 13:
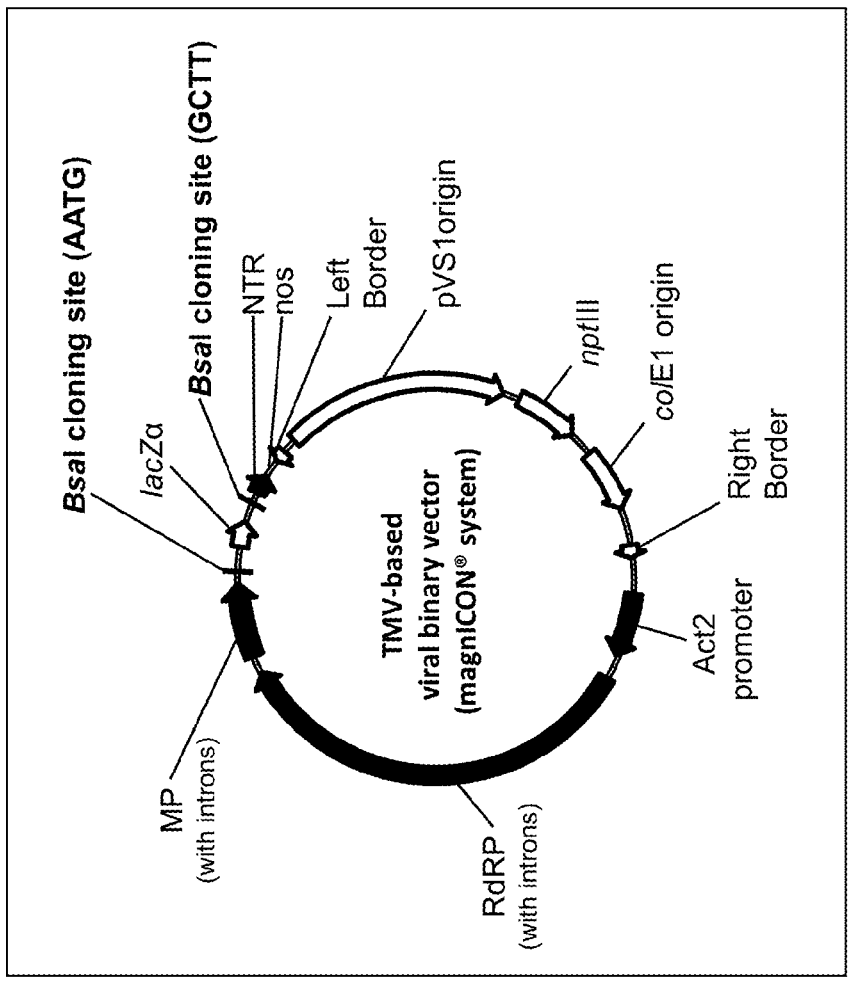

FIG. 13: Schematic map of a TMV-based viral binary vector (magnICON® system). The backbone elements of the binary vector are a pVS1 origin for plasmid replication in *Agrobacterium*, a colE1 origin for plasmid replication in *E. coli* and a nptIII kanamycin antibiotic resistance gene for selection. For delivery of TMV-based viral vectors to plant cells, *Agrobacterium tumefaciens* is used. Therefore, the complete viral construct was cloned between the T-DNA left and right borders of the binary vector. The viral construct consists of the viral cDNA which encodes a RNA-dependent RNA polymerase (RdRP) and the Movement Protein (MP). For efficient expression plant introns were added within the RdRP and MP sequences. The gene for the coat protein was removed and is replaced by the gene of interest in the final expression vector. The viral construct also contains the 5' and 3' non-translated (NTR) viral sequences which are essential for replication. For efficient expression of the viral RNA in plant cells, the viral cDNA has been cloned between a plant promoter and a plant terminator (Act2 and nos). To facilitate blue/white selection a lacZα cassette was inserted between two BsaI restriction sites which allow seamless in frame cloning of the gene of interest. All naturally occurring BsaI recognition sites were removed.

Figure 14:
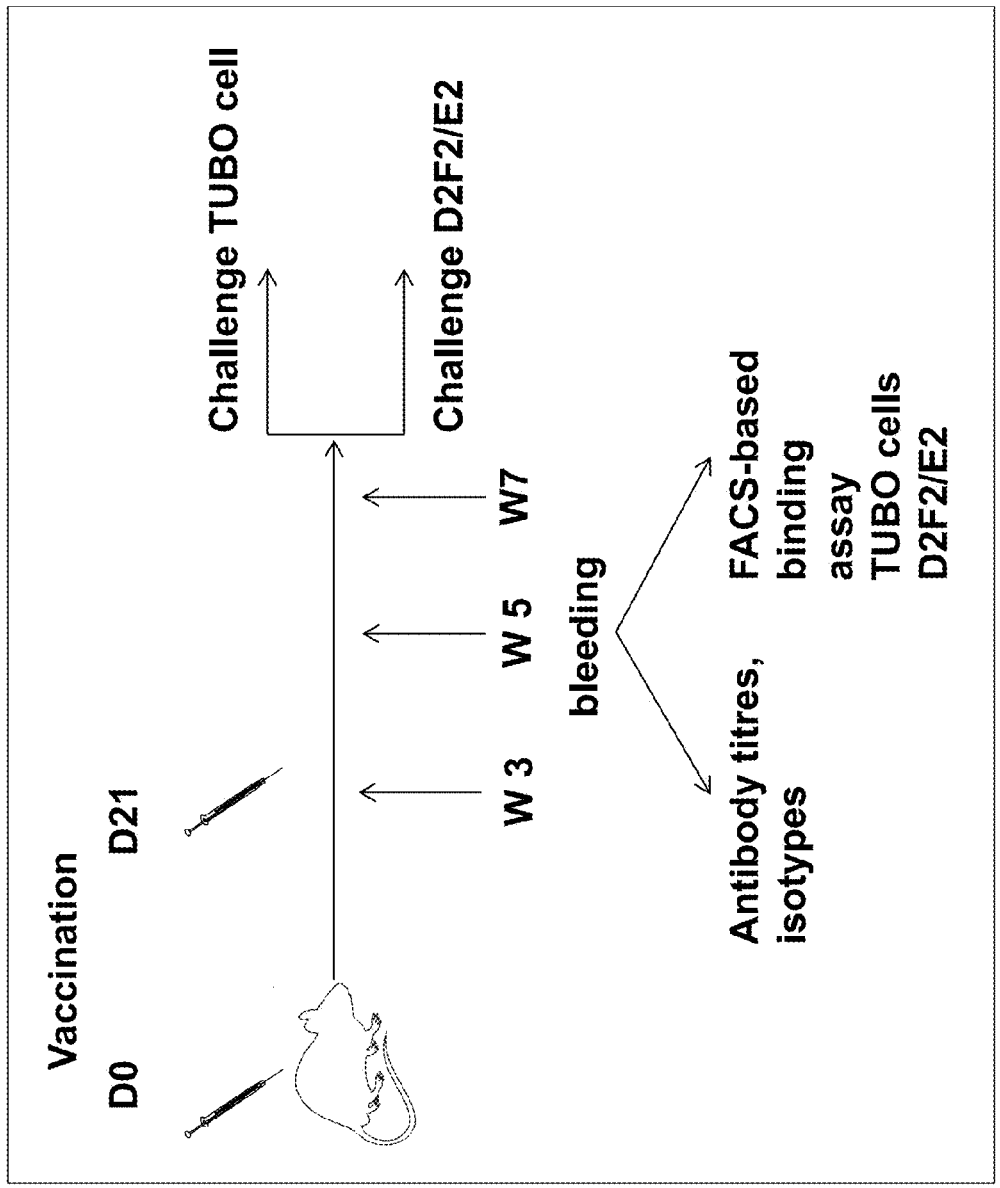

FIG. 14: Schematic representation of experimental design for evaluation of Her2-ED44-based vaccines made in *Nicotiana benthamiana*.

Separate groups of Balb/c mice are immunised with 50 μg of rat Her2-ED44-His vaccine or conjugate vaccines Her2ED44-FrC or Her2ED44-TMV (both contain an equivalent amount of Her2-ED44). All Her2ED44-containing vaccines were combined with an equal volume of alum adjuvant (Sigma) and a total of 200 μL of alum absorbed vaccines are administered s.c. into two sites in the flank. For the control vaccine, 130 μg of plant expressed irrelevant protein (5T33lg-hkappa-Fragment C fusion protein made by ICON) are given as above. A DNA vaccine (50 μg) encoding the Her2/neu full length extracellular plus transmembrane domains (EC-TM) (Prof. Forni, University of Turin, Italy; Quagliino, E., Mastini, C., Forni, G. et al., 2008, *Curr. Protoc. Immunol.*, Ch. 20: Unit 20.9.1-20.9-10) was administered i.m. into a separate group of mice to serve as a comparator vaccine. At least five mice per group were vaccinated per each experiment. Each group of mice received a second injection of the same amount of the homologous vaccines three weeks (D21) after the first injection. The mice were bled 3 weeks after the first injection and before the second injection and two times after second injection with two weeks interval between the bleedings (week 5 and week 7). The sample were analysed by ELISA for reactivity against Her2-ED44 and for reactivity against membrane bound Her2/Neu using the TUBO tumour cell line expressing rat Her2 (Neu) or the D2F2/E2 tumour cell line expressing human Her2. In tumour challenge experiments mice previously injected with two doses of the vaccines were challenged with either the TUBO cell or D2F2/E2 cells. $10^5$ cells per mouse were injected s.c. in the flank in each instance 7 week after the last injection of the vaccines.

Figure 15:
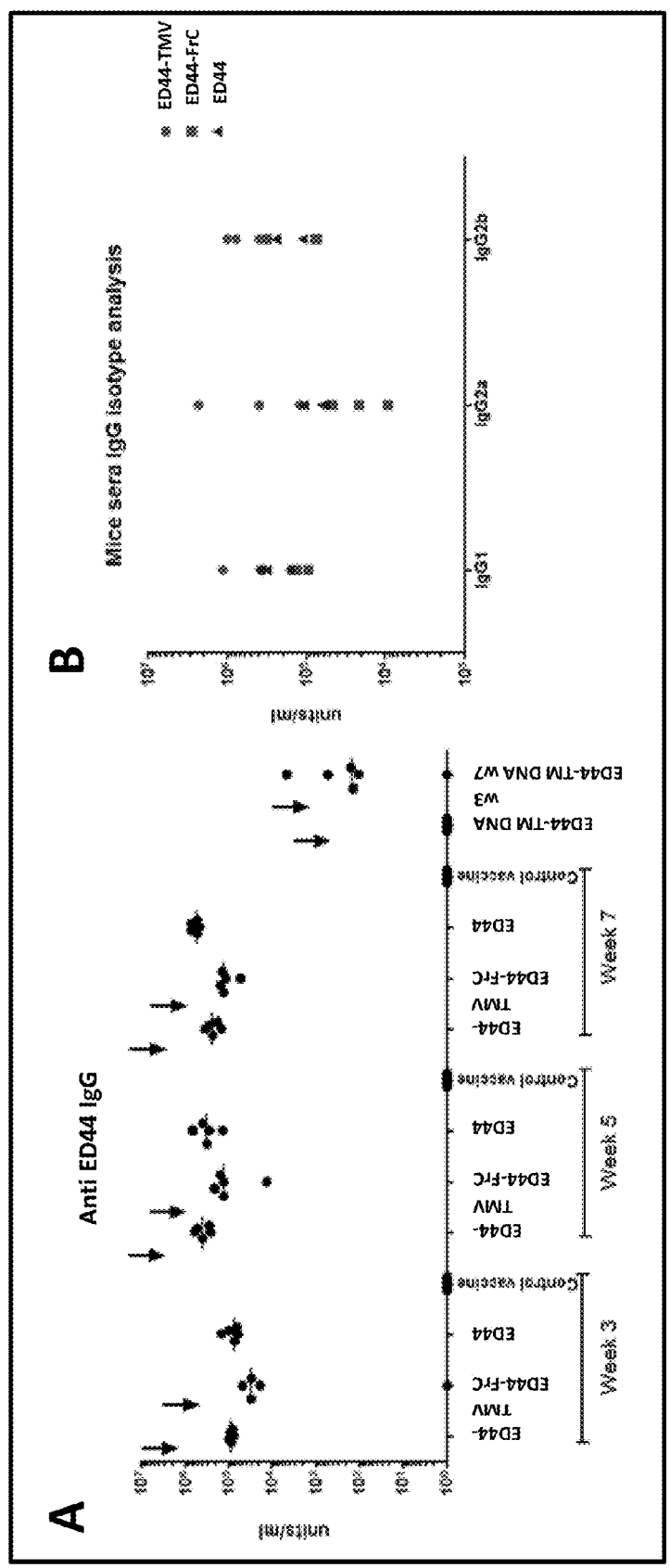

FIG. 15: Total IgG antibody responses and antibody isotypes induced in Balb/C mice following vaccination with rat Her2-ED44 based vaccines rHer2-ED44-TMV (ED44-TMV), rHer2-ED44-Fragment C (ED44-FrC) or rHer2-ED44-His (ED44). Antibody isotypes were measured at week 5.

Figure 16:
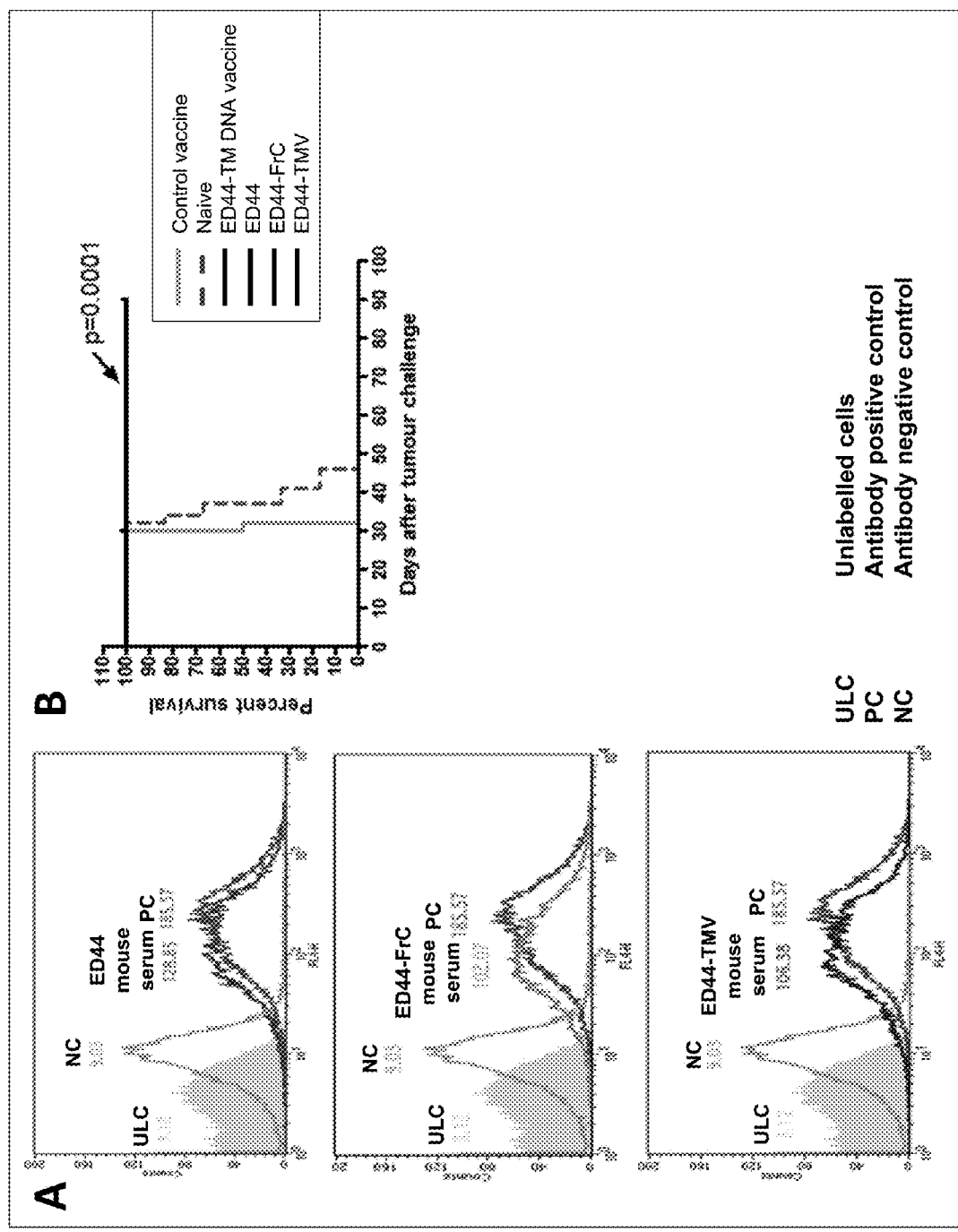

FIG. 16: Binding to rat Her2/Neu expressed on the surface of the TUBO carcinoma cell line. The numbers on the FACS plot above the histograms represent the mean of fluorescent intensity (MFI). Protection of rat Her2-ED44 vaccinated mice against a challenge with the Tubo carcinoma cell line.

Figure 17:
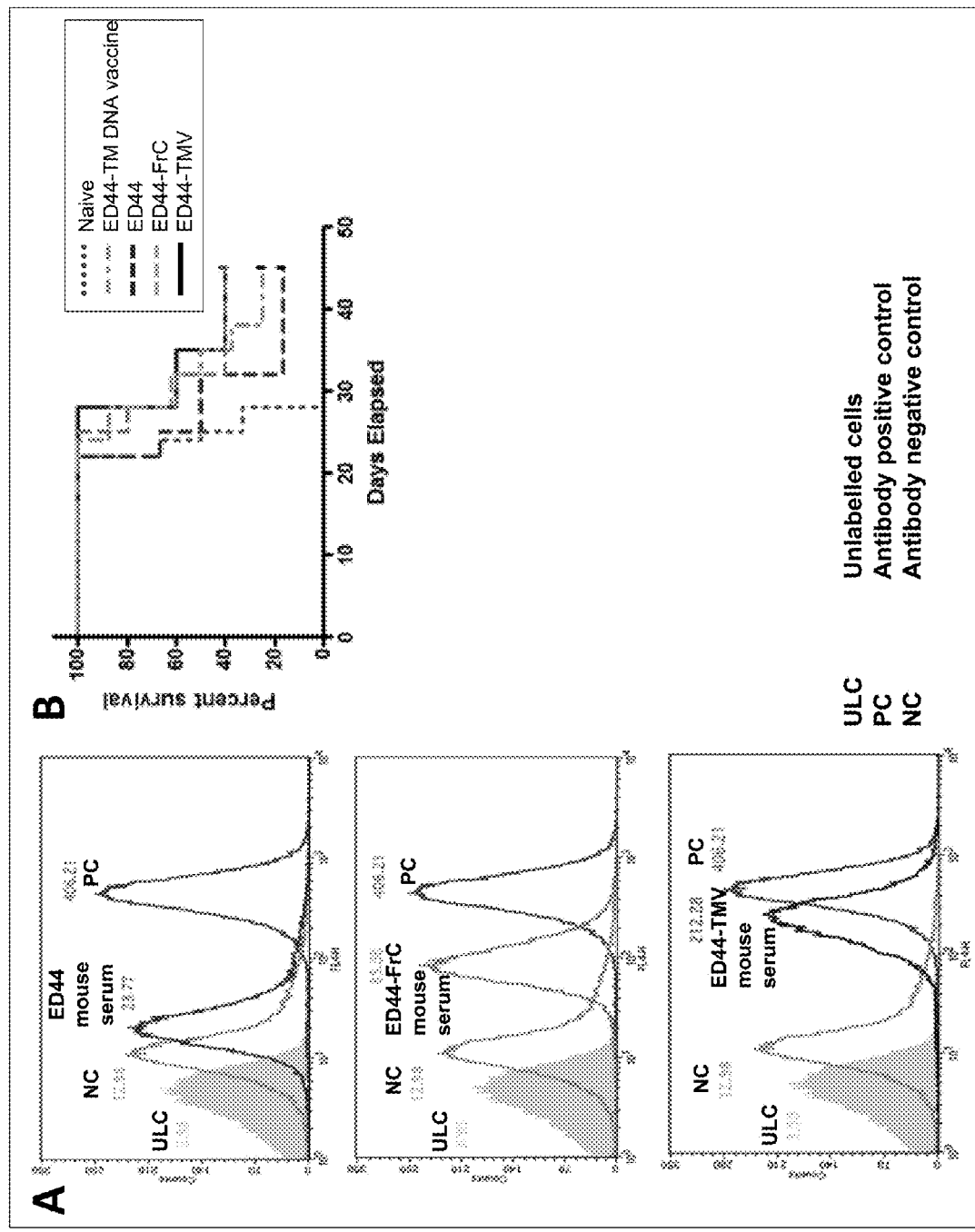

FIG. 17: Binding to human Her2/neu expressed on the surface of the D2F2/E2 carcinoma cell line. The numbers on the FACS plot above the histograms represent the mean of fluorescent intensity (MFI). Protection of rat Her2-ED44 vaccinated mice against a challenge with the D2F2/E2 cell line.

Figure 18:
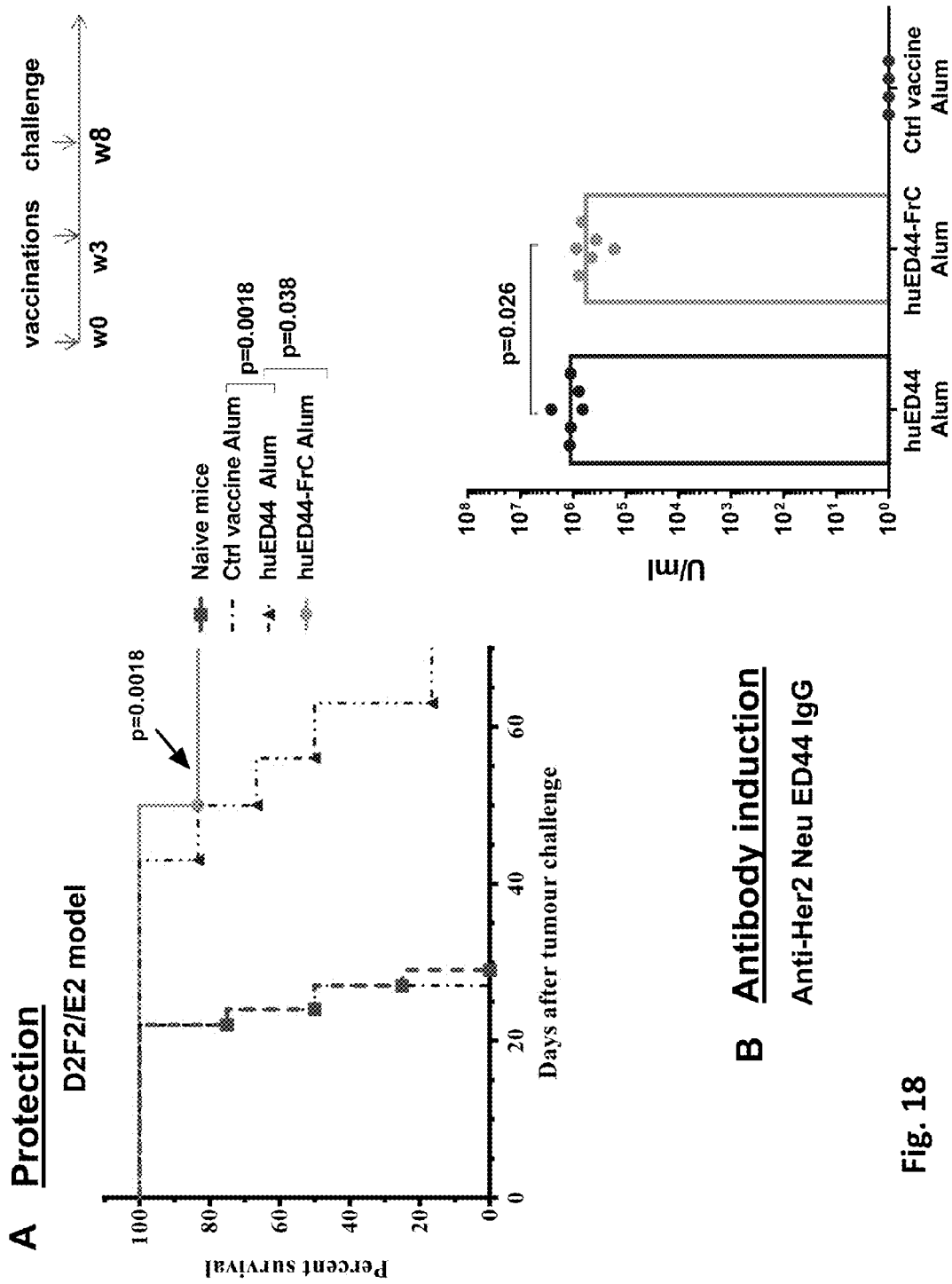
Figure 18:
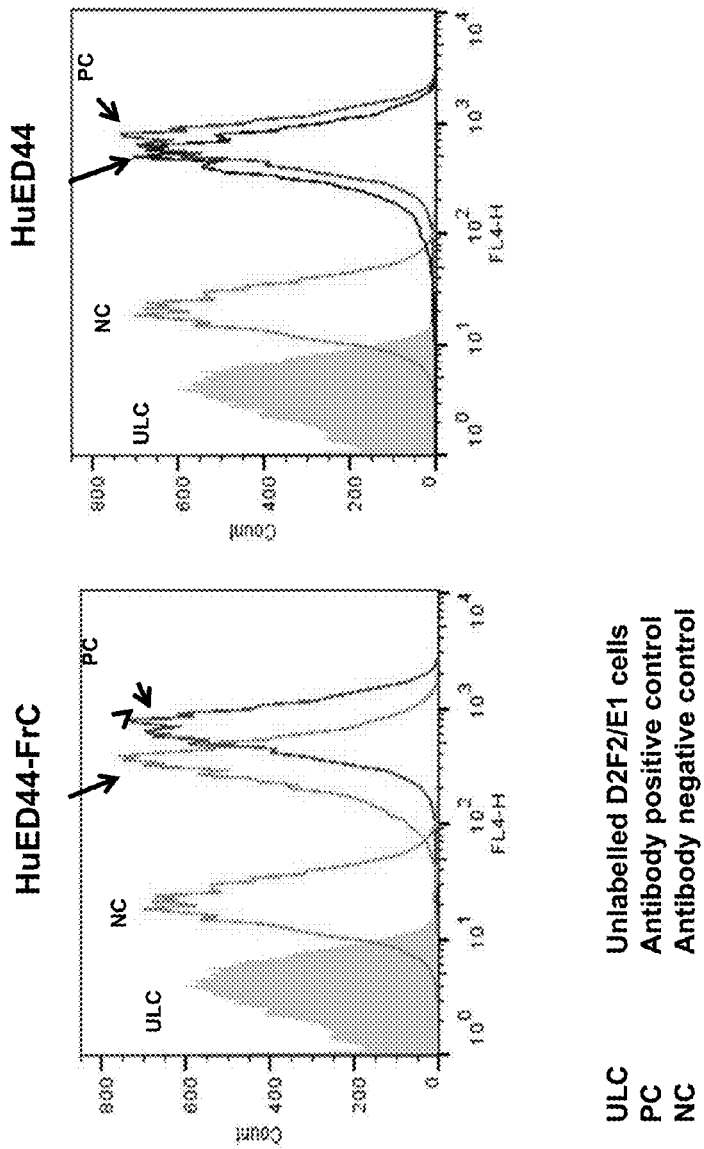

FIG. 18: Human ED44 Her2-FrC study D2F2/E2 breast cancer model: prophylactic setting. Induction of protective immunity by human (hu) ED44-FrC conjugate vaccine or unconjugated huED44. A. Protection against the D2F2/E2 breast carcinoma in a prophylactic setting. B. Levels of anti-Her2/neu antibodies after two injections (d0 and d21) at week 5. C. Binding of induced antibody to native Her2/neu on the D2F2/E2 tumour cells as measured by flow cytometry.

Figure 19:
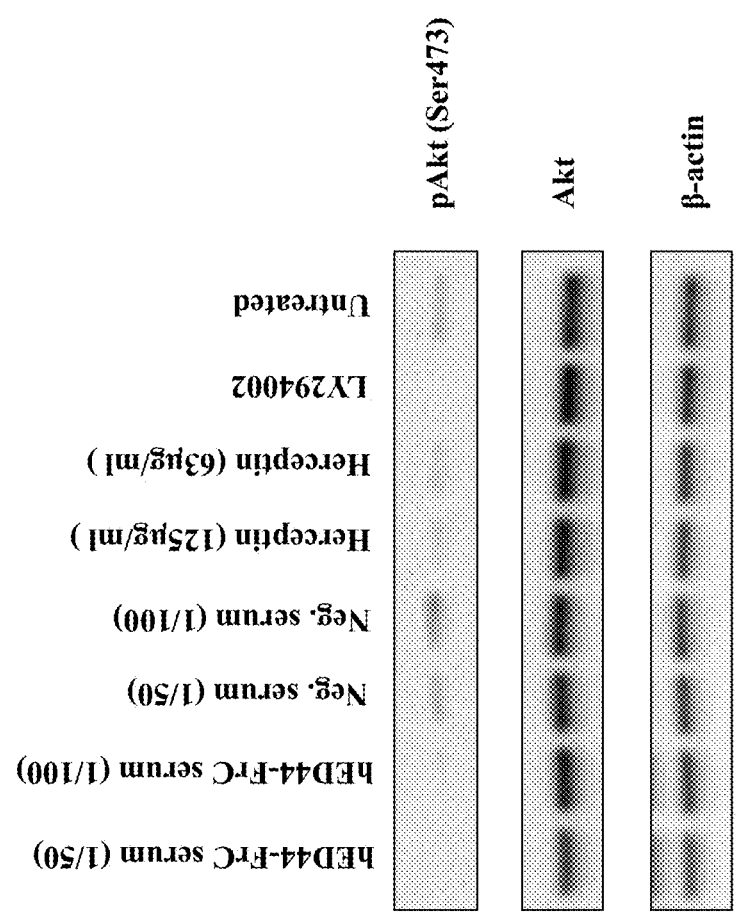

FIG. 19: Inhibition of Her2/neu-mediated signalling (Akt phosphorylation) by antibodies induced with huED44-FrC conjugate vaccine. Evaluation of the ability of antibodies induced by huED44-FrC conjugate vaccine to inhibit Her2-mediated signaling in vitro in comparison with Herceptin and P13K (downstream of Her2 signalling) inhibitor LY294002. The Her2 positive human Breast cancer cell line BT474 was treated separately with serum from mice vaccinated with huED44-FrC, control vaccine, Herceptin at dilutions indicated or LY294002 (30 µM), inhibits Akt phosphorylation (Cell signalling)). Western blot analysis was performed after treatments as indicated using antibody to either phosphorylated Akt (Ser473, top panel), total Akt (middle panel) or B-actin (bottom panel).

The human HER2 positive breast cancer cell line BT474 was separately incubated with pooled serum samples from vaccinated mice at dilutions indicated, trastuzumab (Herceptin®, Roche, UK) or 30 µM LY294002 inhibotor (Cell Signalling Tecnology, Massachusetts, USA) for 1 hour. All treatments were carried out in complete DMEM media supplemented with 10% FCS at 37° C., 10% $CO_2$. After the incubation, the cells were harvested, lysed and 10 µg of protein per sample were subjected to SDS-PAGE (Nu-PAGE® Novex® 4-12% Bis-Tris Gels, Invitrogen Life Technologies, California, USA) after denaturing at 95° C. for 5 minutes. Following the electrophoresis, the proteins were transferred to a polyvinylidene difluoride (PVDF) membrane (Amersham Hybond™-P, GE Healthcare, Buckinghamshire, UK) and after blocking in 5% non-fat milk in Tris buffered saline (TBS) with 0.1% Tween® 20, (TBS-T) were incubated sequentially with anti-pAkt (rabbit anti-phosphor-Akt (Ser 473) antibody, Cell Signalling Technologies), Akt (rabbit anti-Akt antibody, Cell Signalling Technologies) or β-actin (mouse anti-human β-actin antibody, clone 2F1-1, BioLegend) antibody at 1/1,000 dilution. Before applying each subsequent antibody the previous antibody was stripped. After washing 3 times with TBS-T prior the membranes were incubated with 1/1,000 in TBS-T of the HRP-conjugated secondary antibody (anti-rabbit IgG-HRP, Cell Signalling Technologies or anti-mouse IgG (Gamma) (AFF)-PEROX, The Binding Site, Birmingham, UK) for 1 hour at room temperature. The membrane was washed 3 times with TBS-T again before c detection with the SuperSignal™ West Pico Chemiluminescent Substrate (Thermo Scientific, Illinois, USA). The chemiluminescent signal was captured using Bio-Rad imaging system (Fluor-S® Multilmager, Bio-Rad).

Figure 20:
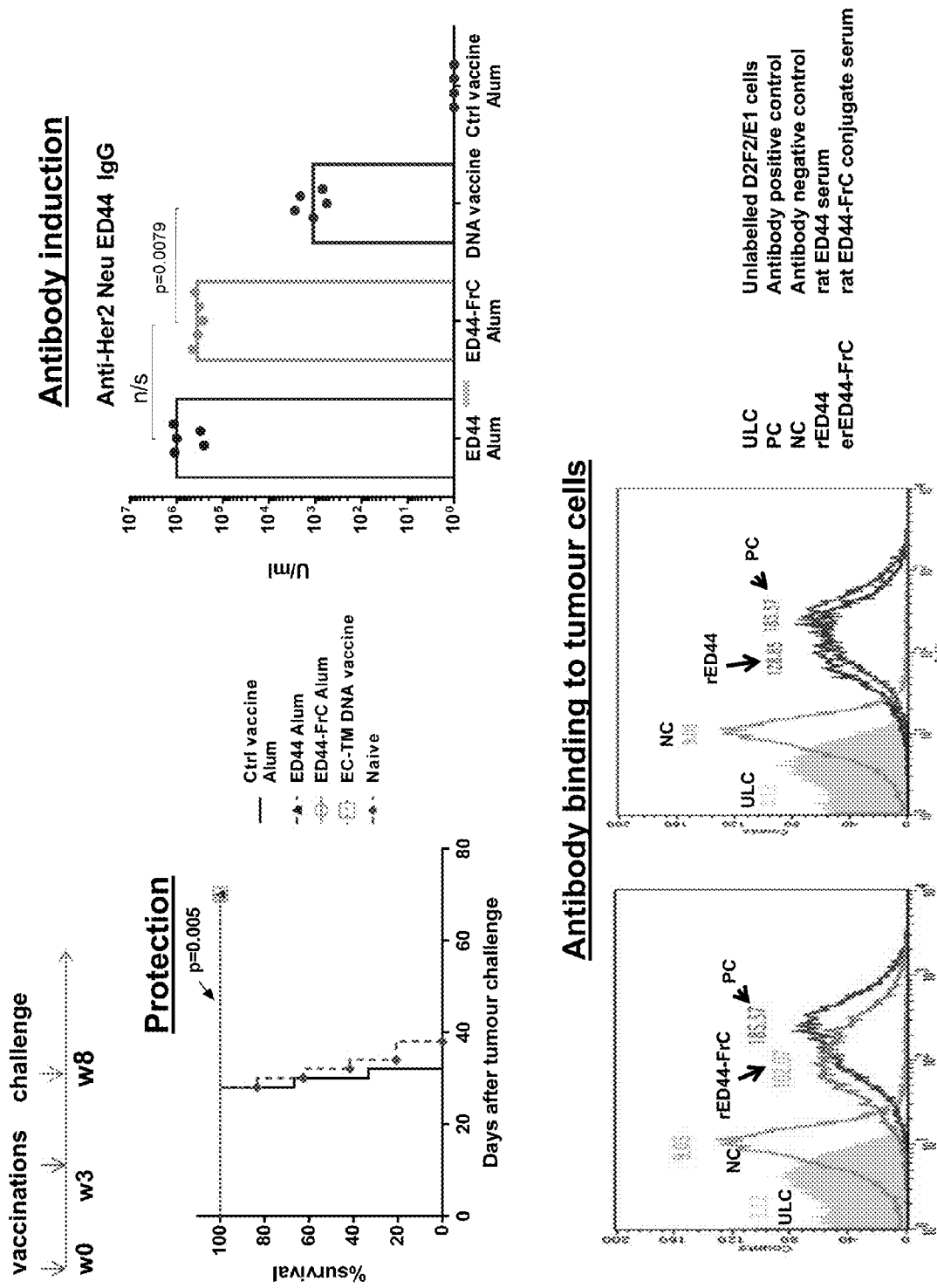

FIG. 20: Rat ED44 Her2-FrC study TUBO model: prophylactic setting.

Experimental design and testing of the rat ED44-FrC conjugate vaccine and unconjugated rat ED44 in the TUBO model of a prophylactic setting. Both vaccines induced highly significant protection against the tumour challenge (top left panel) which was similar to the EC-TM DNA vaccine (gift from Prof. Forni, University of Turin, Italy; Quagliino, E., Mastini, C., Forni, G. et al., 2008, Curr. Protoc. Immunol., Ch. 20: Unit 20.9.1-20.9-10). This protection was accompanied by induction of antibodies to Her2 ED44 by both vaccines, with the levels in each case being significantly higher than those induced by the DNA vaccine (top right panel). The induced antibody also bound to the native Her2 expressed on the surface of TUBO cells (bottom panel).

Figure 21:
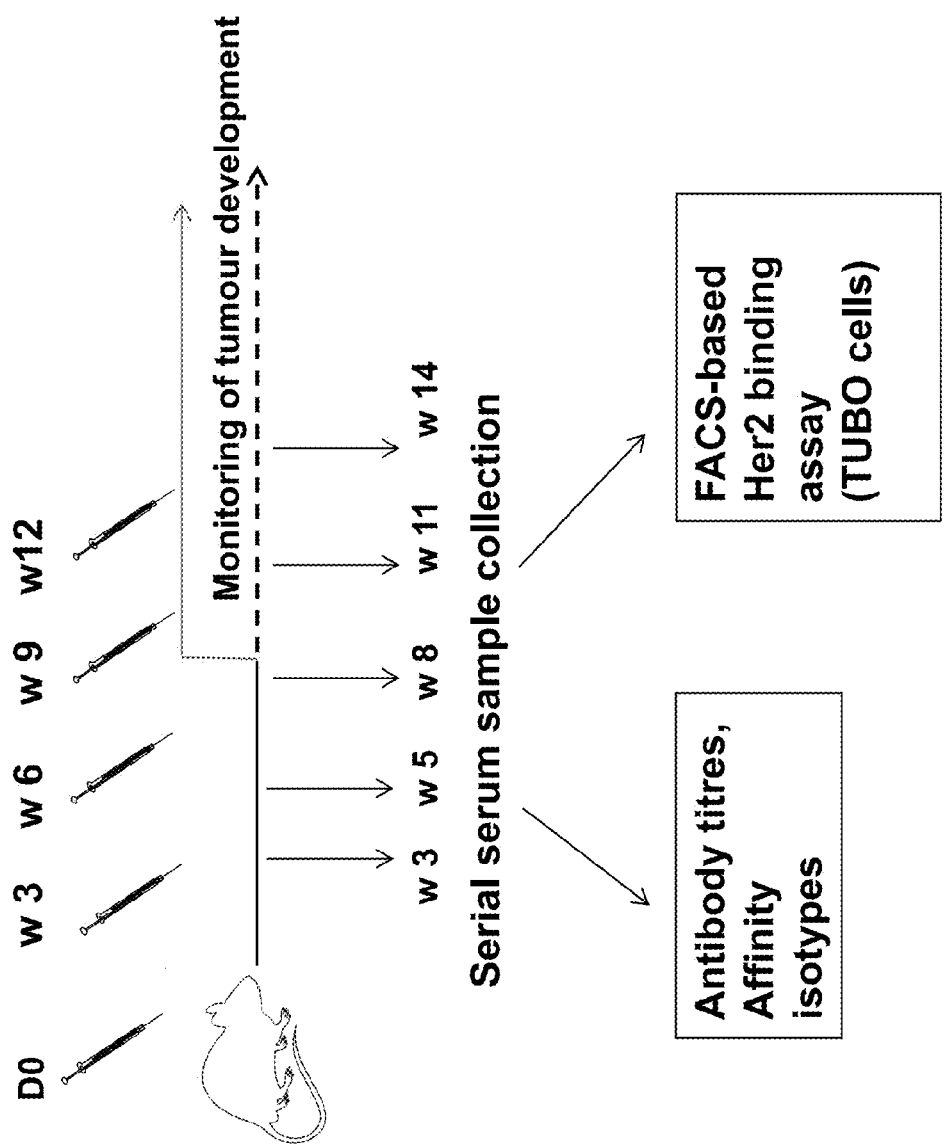
Figure 21:
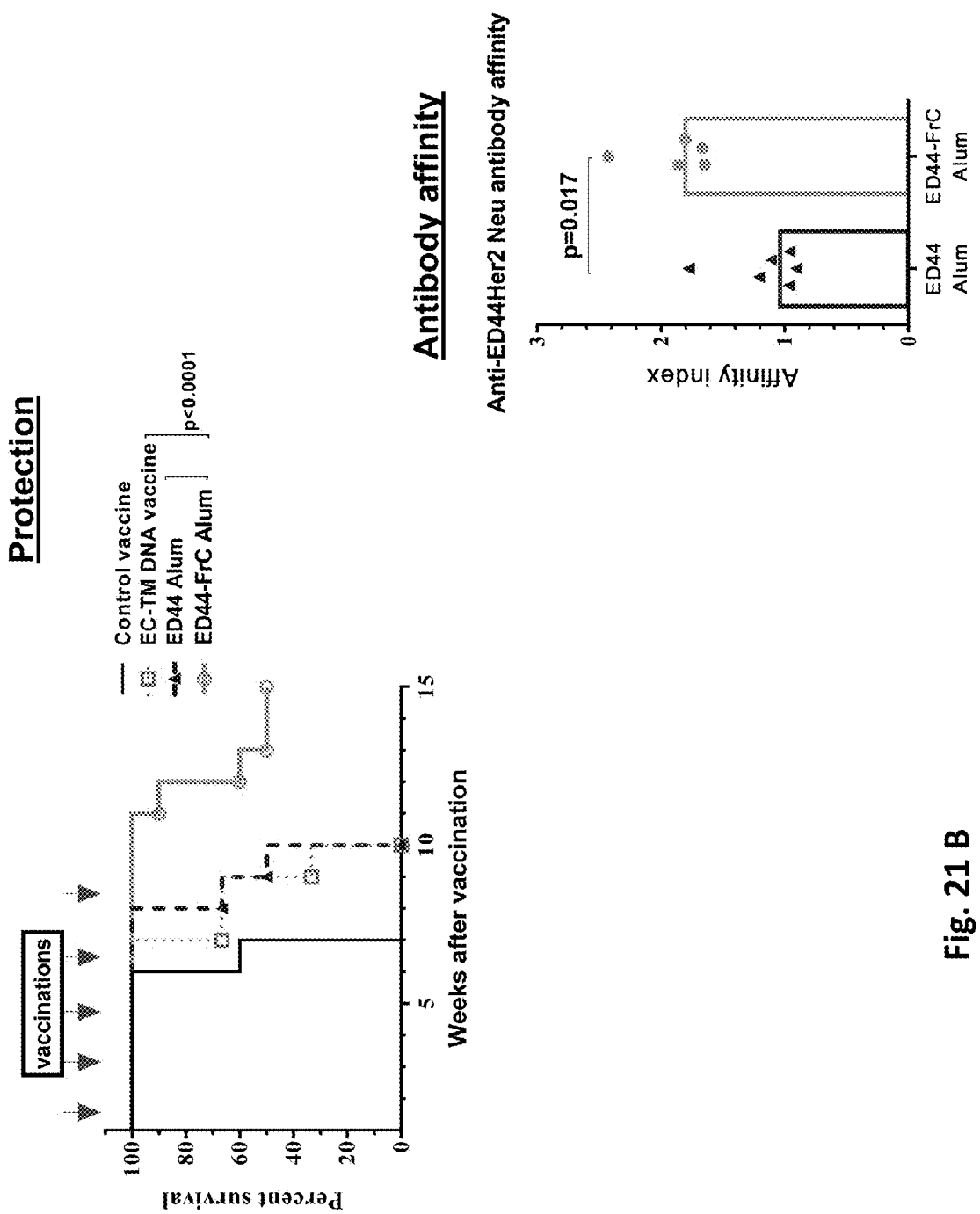
Figure 21:
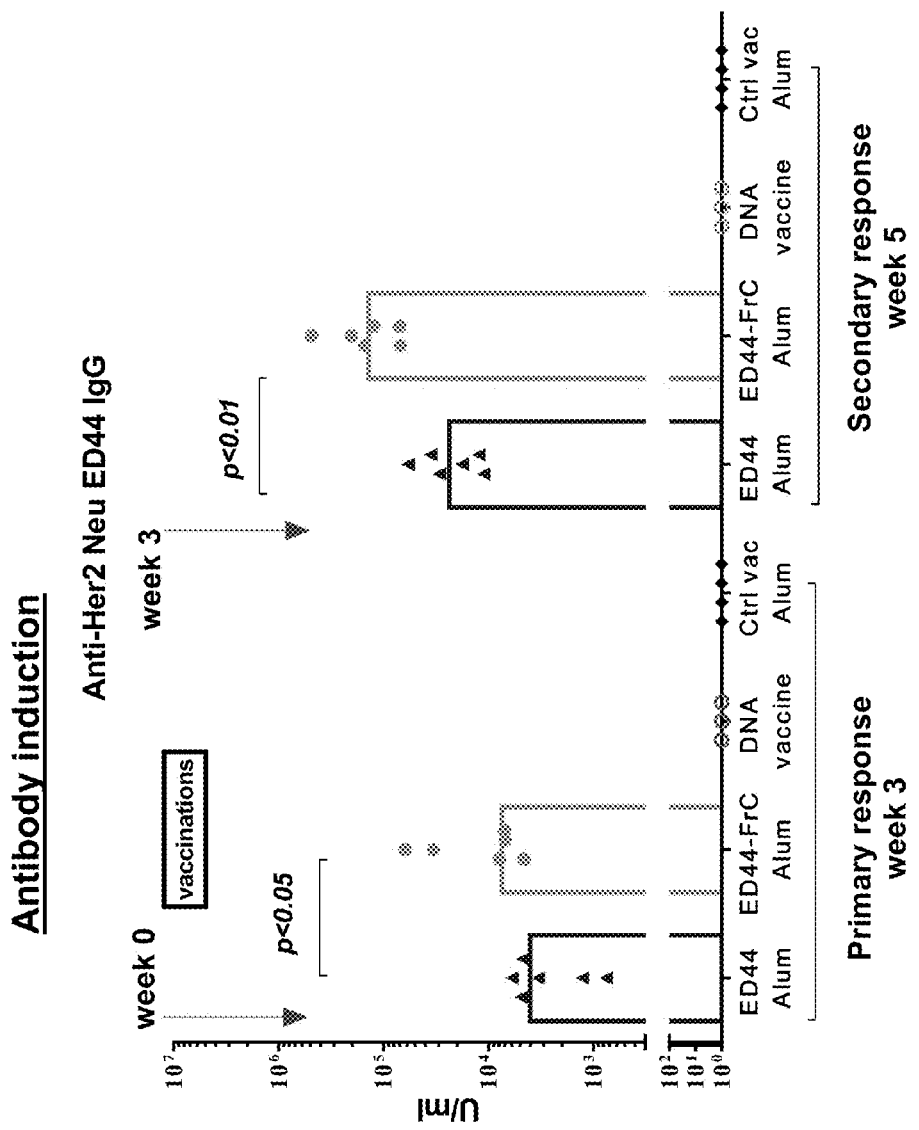

FIG. 21: Experimental design and results of testing of the ED44-FrC vaccine in the Balb-NeuT model of a spontaneous metastatic breast cancer.

A—Protocol for vaccinations and sample collections for experiments in therapeutic setting of a metastatic breast cancer (Balb-NeuT model). Schematic presentation of the experiment in the therapeutic setting. 10-11 weeks old Balb-NeuT female mice (the age when they develop multiple cancinomas with micrometastasis to the bone marrow and lungs) were vaccinated with the same amounts and formulation of the rat ED44, ED44-FrC vaccines or the EC-TM DNA (control vaccine, Quagliino, E., Mastini, C., Forni, G. et al., 2008, Curr. Protoc. Immunol., Ch. 20: Unit 20.9.1-20.9-10) as for the TUBO model following the protocol for vaccination and bleeding as indicated. The Balb-NeuT mice were terminated if combined tumour size reached 15 mm. Results of the experiment are shown in B.

B. Balb-NeuT model transgenic: therapeutic setting of breast carcinoma with metastasis ED44-FrC generated significant protection from the tumor whereas unconjugated vaccine ED44 or the EC-TM DNA vaccines failed to generate significant protection (top panel). ED44-FrC vaccine also induced significantly higher IgG antibody levels than ED44 or the EC-TM DNA vaccines (bottom left panel). The affinity of Her2ED44 specific antibody in the ED44-FrC-vaccinated mice was significantly higher than in the ED44-vaccinated mice (bottom right panel). Antibody affinity was measured using a chaotropic ELISA. Hence conjugate ED44-FrC vaccine in therapeutic setting induces higher anti-Her2 antibody levels and affinity than unconjugated or EC-TM DNA vaccine. EC-TM DNA vaccine is from G. Forni's laboratory (University of Turin, Italy).

Figure 22:
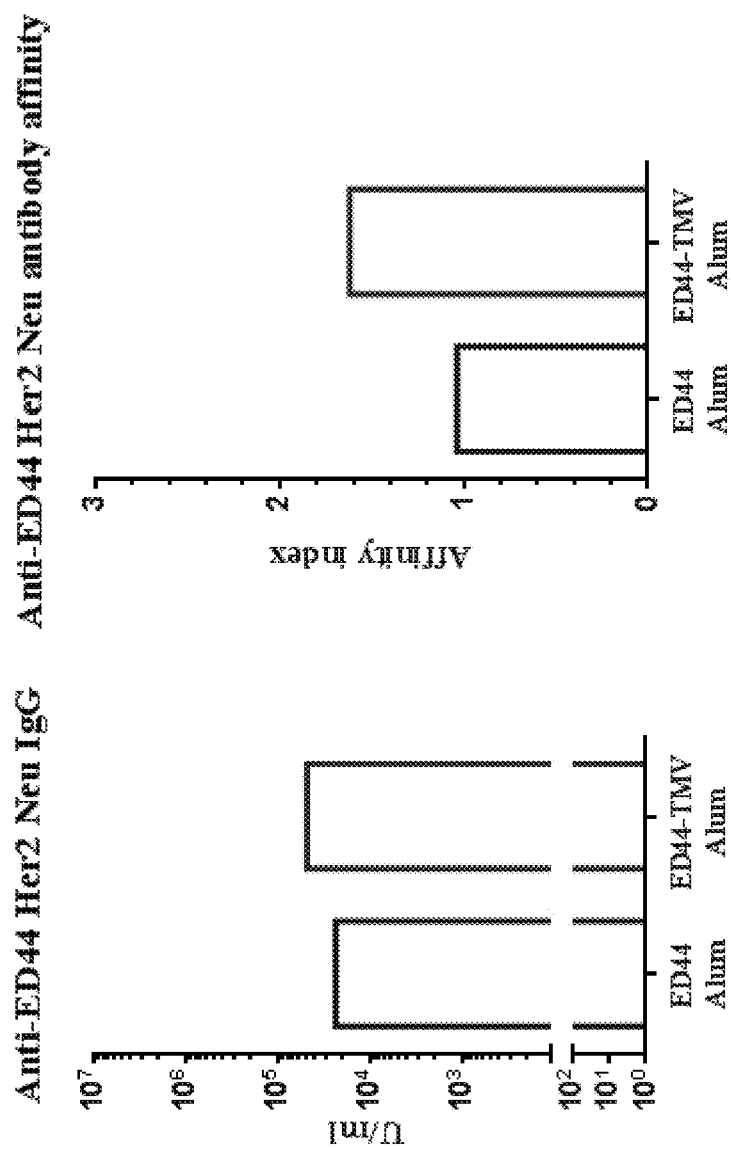

FIG. 22: Results of testing the ED44-TMV vaccine in the Balb-NeuT model of a spontaneous metastatic breast cancer using experimental design as in FIG. 21A (therapeutic setting of breast carcinoma with metastasis). Ten-eleven weeks old Balb-NeuT female mice (the age when they develop multiple carcinomas with micrometastasis to the bone marrow and lungs) were vaccinated with the 50 μg ratED44 or 70 μg ED44-TMV vaccines with alum following the protocol for vaccination and bleeding as for the TUBO model. ED44-TMV vaccine induced higher IgG antibody levels than ED44. The affinity of Her2ED44 specific antibody in the ED44-TMV-vaccinated mice was also higher than in the ED44-vaccinated mice. Both IgG levels and antibody affinity were measured at week 5 after the first injection. Antibody affinity was measured using a chaotropic ELISA.

Quaglino E, Mastini C, Forni G, Cavallo F. (2008) ErbB2 transgenic mice: a tool for investigation of the immune prevention and treatment of mammary carcinomas. Curr Protoc Immunol. 2008 August; chapter 20: Unit 20.9.1-20.9-10. doi: 10.1002/0471142735.im2009s82.

DETAILED DESCRIPTION OF THE INVENTION

The protein conjugate of the invention is a conjugate between the protein antigen and the immunogenic carrier (also referred to simply as "carrier"). In the conjugate of the invention, the protein antigen and the carrier are cross-linked, which means that they are linked by at least one covalent chemical bond. However, there may be multiple covalent bonds between one molecule of a protein antigen and a carrier particle or carrier molecule. The protein antigen is a protein that may consist of one amino acid sequence. The purpose of the protein antigen is to generate a polyclonal immune response against the extracellular domain of HER2/Neu. The purpose of the carrier is to generate a durable humoral or T cell-dependent immunity against HER2/Neu and to overcome tolerance against HER2/Neu. Thus, the protein conjugate can bring about a broad and durable humoral or T cell-dependent immunity against HER2/Neu positive cancers.

The human HER2 protein of 1255 amino acids (SEQ ID NO: 18) has an N-terminal extracellular domain that is defined herein as to extend up to and including amino acid 653, a transmembrane domain of amino acids 654 to 675, and a C-terminal intracellular domain (ICD) from amino acids 676 to 1255 of SEQ ID NO: 18.

In the present invention, the protein antigen is a protein comprising or consisting of a segment that can elicit an immune response against the HER2/Neu protein when the protein conjugate or the protein antigen is administered to a patient as a vaccine. This segment is also referred to herein as "first segment". Herein, a segment is a portion in the linear amino acid sequence of a protein. The protein antigen may consist of a segment that can elicit an immune response against the HER2/Neu protein. Generally, however, the protein antigen contains further portions or segments in addition to the segment that can elicit the immune response against the HER2/Neu protein. Such further portions or segments may be portions that function as a signal peptide or portions that allow easy purification of expressed protein antigen, such as a purification tag. Purification tags, and other portions, may be linked via linker peptides to the remainder of the protein antigen, whereby the linker may allow cleavage of the tags. Examples of purification tags are the 6×His-tag or the constant portion of an antibody light chain. The light chain may be a kappa light chain or a lambda light chain. The light chain is preferably taken from the species to be vaccinated. Since the main purpose of the invention is vaccination of humans, light chains from human antibodies are preferably used as purification tags. Preferred purification tags are the constant regions from antibody light chains, since they are abundant in the bloodstream of patients and therefore generally do not cause any adverse reactions. Thus, such purification tags do not need to be cleaved off from the protein antigen after expression and purification of the protein antigen.

Herein, the segment (of the protein antigen) that can elicit an immune response against the HER2/Neu protein has a substantial length in order to generate a polyclonal immune response, preferably against multiple epitopes of the ECD of HER2/Neu. For this purpose, the protein antigen has a segment of substantial length taken from the ECD of the HER2/Neu protein or a segment of substantial length having a high sequence similarity or identity to a segment from the ECD of the HER2/Neu protein. The length of the segment is at least 300 amino acid residues, preferably at least 320 amino acid residues. The length is preferably at most 600 amino acids, preferably at most 500, and more preferably at most 400 amino acid residues. In other preferred embodiments, the length is from 300 to 400 amino acids, or from 320 to 370 amino acids. In even more preferred embodiments, the length of this segment is from 330 to 360 or from 337 to 350 amino acid residues. In the examples, the segment having 344 amino acids is used, which is referred to herein as "ED44", wherein "44" indicates the molecular of 44 kDa and "ED" stands for "extracellular domain".

The segment that can elicit an immune response against HER2/Neu may have an amino acid sequence taken from the ED of HER2/Neu that is given in SEQ ID NO: 1. The sequence segment of the protein antigen of 300 or more contiguous amino acids of the amino acid sequence of SEQ ID NO: 1 preferably comprises the amino acid sequence segment from amino acid 332 to 631, more preferably from amino acid 325 to 640, and even more preferably from amino acid 317 to 647, of SEQ ID NO:1 or variant sequence segments as defined in items (ii) or (iii). As further explained below, the protein antigen does generally not contain further sequence segments having a sequence identity of more than 50% to any sequence segment of the HER2 protein.

In another embodiment, the protein antigen has a sequence segment of 300, preferably of 330, more preferably of 337, or more contiguous amino acid residues of the amino acid sequence of SEQ ID NO: 2. Also in this embodiment, the protein antigen does generally not contain further sequence segments having a sequence identity of more than 50% to any sequence segment of the HER2 protein.

In order for the protein antigen to elicit the desired immune response against HER2, the sequence identity to a sequence portion of SEQ ID NO: 1 or SEQ ID NO: 2 does not need to be 100%. Instead, the sequence segment may be a variant having an amino acid sequence having at least 85% sequence identity to a sequence portion from SEQ ID: 1 or SEQ ID: 2. The amino acid sequence identity may be at least 90%, preferably at least 95% and more preferably at least 97%. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. Possible and preferred lengths of the sequence segment (aligned region) are as defined above.

In another embodiment, the sequence segment may be a variant having an amino acid sequence having at least 91% sequence similarity to a sequence portion from SEQ ID: 1 or SEQ ID: 2. The amino acid sequence identity may be at least 91%, preferably at least 94%, more preferably at least 97% and even more preferably at least 99%. Possible and preferred lengths of the aligned region are as defined above. Amino acid sequence similarities and identities may be determined using BLASTX 2.2.14 using the standard settings. The standard settings allow, for example, for sequence gaps in alignments.

Alternatively, the variant sequence segment of the protein antigen may have from 1 to several amino acid additions, substitutions or deletions compared to a sequence portion from SEQ ID: 1 or SEQ ID: 2 over the length of the segment, provided the variant sequence can still elicit formation of antibodies against the ECD of human HER2 protein when injected into an animal (such as a rat or a mouse). The maximum number of amino acid additions, substitutions or deletions may be at most 20, preferably at most 10, more preferably at most 5, whereby the total number of additions, substitutions and additions together determine the number of "amino acid additions, substitutions or deletions". These numbers of additions, substitutions and additions occur over the length of the sequence segment of 300 or more amino acid residues. Preferred lengths are as those given above. Substitutions may take place at those positions in the amino acid sequence where an aligned rat and human HER2 protein deviate, such as in the alignment shown in FIG. 2. This is based on the fact that antibodies against the ECD of rat HER2 protein are cross-reactive with the ECD of the human HER2 protein and vice versa. Preferably, amino acids at one or more of the following positions of SEQ ID NO:1 may be substituted by residues of other amino acids: 317, 318, 352, 353, 356, 353, 359, 361, 365, 387, 398, 390, 394, 420, 429, 430, 451, 452, 470, 472, 497, 498, 502, 503, 505, 506, 510, 512, 513, 517, 533, 547, 548, 556-559, 572, 574, 579, 585, 593-595, 622, 639, 640, 651.

The definitions of the variant sequence segment by way of minimum sequence identity or similarity and by way of the maximum number of additions or deletions may be combined. Thus, the variant sequence segment may have the minimum sequence identities or similarities to SEQ ID NO: 1 or 2 and from 1 to 20, preferably from 1 to 10, more preferably from 1 to 5 additions and/or deletions, allowing for optimized alignment when determining the sequence identity or similarity. Preferably, the variant sequence segment may have the minimum sequence identities to SEQ ID NO: 1 or 2 and from 1 to 10 additions and/or deletions.

Alternatively, the variant sequence segment of the protein antigen may be encoded by a nucleic acid that hybridizes under stringent conditions to a nucleic acid that is complementary to a nucleic acid sequence encoding SEQ ID: 1 or SEQ ID: 2. The hybridization conditions depend on the G/C composition of DNA probe and salt concentration in hybridization buffer. For hybridization usually different concentrations of SSC buffer are used. 1×SSC buffer contains 150 mM NaCl, 15 mM trisodium citrate, pH 7.0. The hybridization results are directly related to the hybridization stringency, e.g. number of degrees below the Tm (melting temperature) of DNA at which the experiment is performed. Higher number of degrees below the Tm corresponds weaker hybridization stringency. For a aqueous solution of DNA (no salt) the formula for Tm is: Tm=69.3° C.+0.41(% G+C)° C. Herein, stringent conditions are, for example, conditions wherein the hybridization takes place in 1×SSC containing 0.1% SDS at 60° C.

The protein antigen and, preferably, the protein conjugate of the invention preferably do not contain a further amino acid sequence segment as follows:
a further amino acid sequence segment of 20 or more, preferably 10 or more, contiguous amino acid residues from a sequence portion from amino acid 1 to 253, preferably 1 to 283, more preferably 1 to 300, nor from a sequence portion starting from amino acid 670, preferably from amino acid 654, to amino acid 1255 of SEQ ID NO: 18; or
a further amino acids sequence segment of more than 20 contiguous amino acid residues having more than 50%, preferably more than 40%, sequence identity to a sequence portion from amino acid 1 to 253, preferably 1 to 283, more preferably 1 to 300, nor to a sequence portion starting from amino acid 670, preferably from amino acid 654, to amino acid 1255 of SEQ ID NO: 18.

In one embodiment, the protein antigen, and the protein conjugate containing the protein antigen, do not contain an amino acid sequence segment of 10 or more, preferably of 5 or more, contiguous amino acid residues from the transmembrane domain or the intracellular domain of the Her2/neu protein of SEQ ID NO: 18.

In another embodiment, any further sequence segment (of the protein antigen) of a length of at least 7 amino acid residues of said protein antigen has an amino acid sequence identity less than 50% to any sequence portion of identical length of SEQ ID NO: 18.

In a further embodiment, the protein antigen consists of a first sequence segment that can elicit the immune response against the HER2 protein and optionally a further sequence segment, wherein said first sequence segment
(i) has an amino acid sequence of 300, preferably of 330, more preferably of 337 or more contiguous amino acid residues of the amino acid sequence of SEQ ID NO: 2; or
(ii) has a variant amino acid sequence of 300, preferably of 330, more preferably of 337 or more amino acid residues, and the amino acid sequence of said variant sequence segment has at least 85% or at least 90% or at least 95% sequence identity to a sequence portion from SEQ ID: 2; or
(iii) has a variant amino acid sequence of 300, preferably of 330, more preferably of 337 or more amino acid residues and has from 1 to 20 substitutions, deletions or additions in said variant sequence compared to a sequence segment of 300 or more amino acid residues, or of an amino acid sequence of the same length in terms of number of amino acid residues, of the amino acid sequence of SEQ ID NO: 2;
and wherein said protein antigen (or the protein conjugate containing the protein antigen) does not contain a further amino acid sequence segment of 20 or more, preferably 10 or more, contiguous amino acid residues from a sequence portion from amino acid 1 to 253, preferably 1 to 283, nor from a sequence portion starting from amino acid 670, preferably from amino acid 654 of SEQ ID NO: 18.

In the protein conjugate containing the protein antigen, the protein antigen and the immunogenic carrier are preferably covalently bonded by chemical cross-linking using a chemical cross-linking agent.

The protein antigen may be cloned and expressed according to generally known methods. However, expression is preferably done in eukaryotic cells. A nucleic acid encoding the desired portion or the first segment from the extracellular domain of HER2/Neu may be cloned using primers designed for such portion using the known gene sequence of the HER2 gene. The GenBank accession no. for the Her2/neu gene is: AAA75493 (SEQ ID NO: 18). Many different expression systems that are based on different production hosts (bacteria, fungi, animal, insect and plant cells) and expression vectors designed either for stable transgenic or transient expression can be used. All such systems are well known to the skilled person and described (for review see: Huang, C. J., Lin, H. & Yang, X. 2012, *J. Ind. Microbiol. Biotechnol.*, 39:383-399; Hou, J., Tyo, K. E., Liu, Z. et al., 2012, *FEMS Yeast Res.*, 12:491-510; Martinez, J. L., Liu, L., Petranovic, D. et al., 2012, *Curr. Opin. Biotechnol.*, April 12. [Epub ahead of print]; Su, X., Schmitz, G., Zhang, M. et al., 2012, *Adv Appl Microbiol.*, 81:1-61; Ghaderi, D., Zhang, M., Hurtado-Ziola, N.& Varki, A. 2012, *Biotechnol. Genet. Eng. Rev.*, 28:147-175; Egelkrout, E., Rajan, V. & Howard, J. A., 2012, *Plant Sci.*, 184:83-101) and the choice of the system depends on factors such as cost of materials or the speed required for the protein production. Our preferred choice are plant expression systems, notably plant virus-based transient expression system due to speed, yield and universality in production of different types of recombinant proteins including the hetero-oligomeric proteins like mono-clonal antibodies. Another important advantage of plant expression systems is the ability to provide for the production of plant viral particles by allowing expression of plant viral coat protein or fusion proteins from the expression vector (Werner, S. et al., 2006, *Proc. Natl. Acad. Sci. USA*, 103:17678-17683; WO2007031339). Such systems are described in detail in numerous research articles, reviews and patents (Marillonnet, S., Thoeringer, C., Kandzia, R. et al., 2005, *Nat. Biotechnol.*, 23:718-723; Giritch, A., Marillonnet, S., Engler, C., et al., 2006, *Proc. Natl. Acad. Sci. USA*, 103:14701-14706; Gleba, Y., Klimyuk, V. & Marillonnet, S. 2007, *Curr. Opin. Biotechnol.*, 18:134-141; Klimyuk, V., Pogue, G., Herz, S. et al., 2012, *Curr Top Microbiol Immunol.*, April 15; WO2005049839; WO2006079546). WO2005049839 contains detailed information of possible plant viral expression vectors, modifications thereof and sequence information thereof. The design of viral vectors, cloning strategy and expression of recombinant proteins and viral particles is described in detail herein in the EXAMPLE 1. Modular cloning strategies for seamless stitching together different DNA fragments was established in our laboratory (Engler, C., Kandzia, R. & Marillonnet, S., 2008, *PLoS One*, 3:e3647; Weber E., Engler, C., Guetzner, R. et al., 2011, *PLoS One*, 6:e16765; Engler, C. & Marillonnet, S. 2011, *Methods Mol Biol.*, 729:167-81; Thieme, F., Engler, C., Kandzia, R. et al., 2011, *PLoS One*, 6:e20556) and used for construct engineering. The system is simple, reliable, convenient to use and allows fast construct engineering of any complexity. The ED44 of human Her2/neu (amino acid residues 310-653; FIG. 1A) and its two truncated variants (amino acid residues 310-649 and 340-649; FIG. 1C, D) have been cloned into viral vectors, tested for the expression level and were used for conjugate generation and vaccine formulation.

After expression of the protein antigen preferably in a eukaryotic host, it is purified using generally known methods. In one embodiment, the protein antigen has a purification tag. Purification can then involve column chromatography using a matrix having affinity to the purification tag.

The immunogenic carrier may have a molecular weight of at least 5 kDa, preferably of at least 10 kDa, more preferably at least 15 kDa, and even more preferably of at least 20 kDa. The molecular weight may, however, still be much larger than 20 kDa and may be higher than 100 kDa. The carrier may or may not be a protein. Preferably, however, the carrier is also a protein. The carrier protein may be a monomeric protein such as tetanus toxin fragment C or the DOM1 fragment (SEQ ID NO: 17) thereof or a multimeric protein. Multimeric proteins may be di-, tri or higher oligomers or even polymers of protein subunits. An example of a widely used carrier that is a polymeric protein is Keyhole Limpet Hemocyanine (KLH) (Harris, J. R. & Markl, J. 1999, *Micron.*, 30: 597-623; Harris, J. R. & Markl, J. 2000, *Eur. Urol.*, 3: 24-33). Examples of other polymeric proteins are viral particles that may consist of or comprise a large number of monomeric protein molecules or subunits, generally multimers of coat protein monomers. Such viral particles may contain viral RNA or DNA. Viral particles are preferred carriers, since they are highly immunogenic, notably in mammals such as humans, and can cause a strong immune response. In one embodiment, the viral particles are plant viral particles, such as of plant tobamoviruses. Viral particles, notably plant viral particles, that may be used as immunogenic carriers in the protein conjugate of the invention are described in more detail in the following.

A viral particle is a multimeric particle comprising a plurality of viral coat protein molecules. The sizes of the viral particles as determined in electron microscopy as described in *Analytical Biochem.*, 333 (2004) 230-235 may be at least 10 nm in the shortest dimension, more preferably at least 13 nm in the shortest dimension.

As mentioned before, viral particles are generally formed of many coat protein molecules. The viral particles, notably the plant viral particles, can be formed by expressing the coat protein molecules in a suitable host such as in a plant or cells thereof as desribed in WO 2007/031339 or by purifying plant viral particles from a plant host that is infected with the plant virus.

Plant viruses, the plant viral particles of which may be used in the protein conjugate of the present invention, are known, see e.g. the book of Drews, Adam, Heinze, "Molekulare Pflanzenvirologie", Springer-Verlag Berlin, Heidelberg 2004. The viral particles may be produced by expressing a polynucleotide encoding the (monomeric) protein, generally the coat protein, that assembles for forming the viral particle in a bacterial or plant host. The plant host may be plant cells, plant tissue or entire plants. Apart from encoding the coat protein, said polynucleotide will have regulatory elements required for the expression of the coat protein in the chosen host. Upon expressing the polynucleotide, the viral particles of the invention generally assemble within host cells or may be assembled in vitro after isolating the coat protein from the host cells under suitable conditions.

The plant viral coat protein may be derived from any plant virus such as the plant viruses listed below. In one embodiment, said plant viral coat protein is derived from a plant virus forming rod-shaped viral particles. Other examples are filamentous and icosahedral plant viral particles. "Being derived" means that the coat protein that forms the plant viral particle does not have to be identical to the natural coat protein of a plant virus. Instead, the coat protein used may have additions, deletions, insertions or mutations relative to a natural coat protein of a plant virus. In one embodiment, at most 20 amino acid residues of the natural plant viral coat protein are deleted and/or mutated. In another embodiment, at most 20 amino acid residues are inserted into the natural sequence of the plant viral coat protein of the plant virus from which the coat protein is derived.

The plant viral particle (and the plant viral coat protein that forms the plant viral particle) and the plant viral particle may be derived from an RNA virus, such as a plant plus-sense single-stranded RNA virus, or from a DNA virus. Examples of plant viruses the coat protein of which may be used for the present invention include tobamoviruses such as tobacco mosaic virus (TMV), turnip vein clearing virus (TVCV), potato virus X, potato virus Y and fragments or homologues thereof, provided said fragments or homologues are capable of forming viral particles. In one embodiment, the coat protein used has a sequence identity of at least 50% to the coat protein of turnip vein clearing virus, to tobacco mosaic virus, potato virus X or potato virus Y. In another embodiment, said sequence identity is at least 60%; in a further embodiment, said sequence identity is at least 70%. In an important embodiment, the coat protein has a sequence identity to the coat protein of tobacco mosaic virus of at least 90%.

Plant viruses belonging to different taxonomic groups that form viral particles can be used as immunogenic carriers according to the principles of the present invention. This is right for both RNA- and DNA-containing viruses, examples for which are given in the following. Names of orders, families and genera are in italic script, if they are approved by the ICTV. Taxa names in quotes (and not in italic script) indicate that this taxon does not have an ICTV international approved name. Species (vernacular) names are given in regular script. Viruses with no formal assignment to genus or family are indicated):

DNA Viruses:
Circular dsDNA Viruses: Family: Caulimoviridae, Genus: Badnavirus, Type species: BM_4_*commelina* yellow mottle virus, Genus: Caulimovirus, Type species: cauliflower mosaic virus, Genus "SbCMV-like viruses", Type species: Soybean chloroticmottle virus, Genus "CsVMV-like viruses", Type species: Cassava vein mosaicvirus, Genus "RTBV-like viruses", Type species: Rice tungro bacilliformvirus, Genus: "*Petunia* vein clearing-like viruses", Type species: *Petunia* vein clearing virus;
Circular ssDNA Viruses: Family: Geminiviridae, Genus: Mastrevirus (Subgroup I Geminivirus), Type species: maize streak virus, Genus: Curtovirus (Subgroup II Geminivirus), Type species: beet curly top virus, Genus: Beqomovirus (Subgroup III Geminivirus), Type species: bean golden mosaic virus;

RNA Viruses:
ssRNA Viruses: Family: Bromoviridae, Genus: Alfamovirus, Type species: alfalfa mosaic virus, Genus: Ilarvirus, Type species: tobacco streak virus, Genus: Bromovirus, Type species: brome mosaic virus, Genus: Cucumovirus, Type species: cucumber mosaic virus;
Family: Closteroviridae, Genus: Closterovirus, Type species: beet yellows virus, Genus: Crinivirus, Type species: Lettuce infectious yellows virus, Family: Comoviridae, Genus: Comovirus, Type species: cowpea mosaic virus, Genus: Fabavirus, Type species: broad bean wilt virus 1, Genus: Nepovirus, Type species: tobacco ringspot virus;
Family: Potyviridae, Genus: Potyvirus, Type species: potato virus Y, Genus: Rymovirus, Type species: ryegrass mosaic virus, Genus: Bymovirus, Type species: barley yellow mosaic virus;
Family: Sequiviridae, Genus: Sequivirus, Type species: parsnip yellow fleck virus, Genus: Waikavirus, Type species: rice tungro spherical virus; Family: Tombusviridae, Genus: Carmovirus, Type species: carnation mottle virus, Genus: Dianthovirus, Type species: carnation ringspot virus, Genus: Machlomovirus, Type species: maize chlorotic mottle virus, Genus: Necrovirus, Type species: tobacco necrosis virus, Genus: Tombusvirus, Type species: tomato bushy stunt virus, Unassigned Genera of ssRNA viruses, Genus: Capillovirus, Type species: apple stem grooving virus; Genus: Carlavirus, Type species: carnation latent virus; Genus: Enamovirus, Type species: pea enation mosaic virus, Genus: Furovirus Type species: soil-borne wheat mosaic virus, Genus: Hordeivirus, Type species: barley stripe mosaic virus, Genus: Idaeovirus, Type species: raspberry bushy dwarf virus;
Genus: Luteovirus, Type species: barley yellow dwarf virus; Genus: Marafivirus, Type species: maize rayado fino virus; Genus: Potexvirus, Type species: potato virus X; Genus: Sobemovirus, Type species: Southern bean mosaic virus, Genus: Tenuivirus, Type species: rice stripe virus,
Genus: Tobamovirus, Type species: tobacco mosaic virus, Genus: Tobravirus, Type species: tobacco rattle virus,
Genus: Trichovirus, Type species: apple chlorotic leaf spot virus; Genus: Tymovirus, Type species: turnip yellow mosaic virus; Genus: Umbravirus, Type species: carrot mottle virus; Negative ssRNA Viruses: Order: Mononegavirales, Family: Rhabdoviridae, Genus: Cytorhabdovirus, Type Species: lettuce necrotic yellows virus, Genus: Nucleorhabdovirus, Type species: potato yellow dwarf virus;
Negative ssRNA Viruses: Family: Bunyaviridae, Genus: Tospovirus, Type species: tomato spotted wilt virus;
dsRNA Viruses: Family: Partitiviridae, Genus: Aiphacryptovirus, Type species: white clover cryptic virus 1, Genus: Betacryptovirus, Type species: white clover cryptic virus 2, Family: Reoviridae, Genus: Fijivirus, Type species: Fiji disease virus, Genus: Phytoreovirus, Type species: wound tumor virus, Genus: Oryzavirus, Type species: rice ragged stunt virus;
Unassigned Viruses: Genome ssDNA: Species: banana bunchy top virus, Species: coconut foliar decay virus, Species: subterranean clover stunt virus,
Genome: dsDNA, Species: cucumber vein yellowing virus; Genome: dsRNA, Species: tobacco stunt virus,
Genome: ssRNA, Species Garlic viruses A, B, C, D, Species grapevine fleck virus, Species maize white line mosaic virus, Species olive latent virus 2, Species: ourmia melon virus, Species *Pelargonium* zonate spot virus.

Examples of sizes and shapes of selected plant viruses are as follows.
Rod-shaped viruses—TMV: the virions have ≈300 nm in length and ≈18 nm in diameter; PVX (filamentous; usually flexuous; with a clear modal length): 515 nm long and 13 nm in diameter; Brome Mosaic Virus: 26 nm in diameter.
Symmetry/shape—icosahedral: Alfalfa mosaic virus (Nucleocapsids bacilliform, or quasi-isometric elongated): 35 nm long (Tb) or 30 nm long; Ta that occurs either in bacilliform (Ta-b) or ellipsoidal (Ta-t) shape) with no clear modal length: 56 nm long (B); 43 nm long (M); 18 nm in diameter.

Preferred plant viral particles are from plant viruses having a single-stranded plus-sense RNA genome. The viruses (tobacco mosaic virus and potato virus X) may be expressed using well-established expression systems for said viruses (Donson et al., 1991, *Proc Natl Acad Sci USA*, 88:7204-7208; Shivprasad et al., 1999, *Virology*, 255:312-323; Marillonnet et al., 2004, *Proc Natl Acad Sci USA*, 101:6852-6857; Marillonnet et al., 2005, *Nat Biotechnol.*, 23:718-723; Chapman, Kavanagh & Baulcombe, 1992, *Plant J.*, 2:549-557; Baulcombe, Chapman & Santa Cruz, 1995, *Plant J.*, 7:1045-1053; Angell & Baulcombe, 1997,

*EMBO J.*, 16:3675-3684) including the very recently developed system for expression of hetero-oligomeric proteins (EP Application No. 05 001 819.1; WO 2006/079546). Plant viral particles from other viruses including DNA viruses also can be used for practicing this invention (for reviews please refer to: Mullineaux et al., 1992, *Genetic Engineering in Plant Viruses*, CRC Press Inc., pp187-215; Timmermans et al., 1994, *Ann. Rev. Plant Physiol. Plant Mol. Biol.*, 45:79-112; Porta & Lomonossoff, 2002, *Biotechnol. Genet. Engineering Rev.*, 19:245-291).

Thus, the immunogenic carrier may be a plant viral particle that may be derived from an RNA virus, such as a Tobamovirus. In another embodiment, the immunogenic carrir is a plant viral particle of a virus from the family Potyviridae. Other options were mentioned above.

Figure 3:
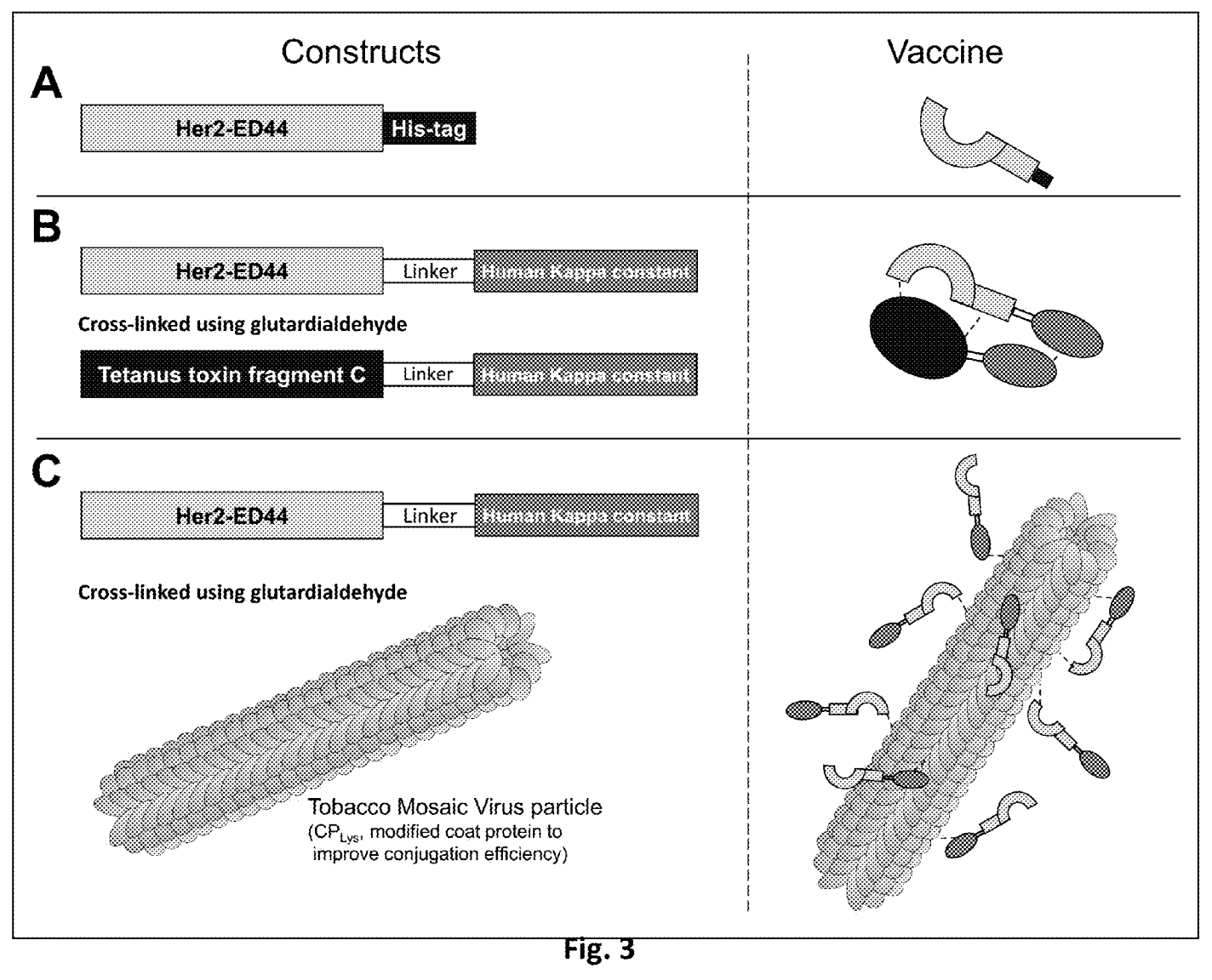

Multimeric carrier proteins may be covalently bonded to multiple protein antigen molecules, e.g. as illustrated in FIG. 3C. Notably, a viral particle as a carrier may be covalently bonded to multiple molecules of the protein antigen.

The best known examples of non-proteinaceous carriers are liposomes (for review see: Felnerova, D., Viret, J. F., Gluck, R., et al., 2004, Curr Opin Biotechnol., 15: 518-29; Tiwari, S., Agrawal, G. P. & Vyas, S. P. 2010, Nanomedicine, 5: 1617-1650).

Carrier proteins may be expressed as generally known in the art, e.g using expression systems such as those mentioned above. Expression of plant viral coat protein and production of plant viral particles is described in detail in WO2007031339. Other carriers are commercially available such as Tetanus toxin fragment C from Sigma-Aldrich (T3694 Sigma) or from Merck-Millipore (No. 582235). As a further alternative, a part of Tetanus toxin fragment C called DOM1 (see SEQ ID NO: 17) can be used. It was shown that, unlike Tetanus fragment C, DOM1 is a novel antigen for B cells in patients and hence would not be recognised by pre-existing antibodies induced because of a tetanus vaccination (Low, L., Manderr, A., McCann, K. et al., 2009, *Human Gene Ther.*, 20:1269-1278), that supposedly might slow down the immune response.

In one embodiment of the invention where the carrier is a protein carrier, the protein conjugate comprising the protein antigen and the carrier protein may be expressed as a fusion protein, i.e. as portions of one amino acid sequence. In such embodiment, the covalent bond between the protein antigen and the carrier protein is a peptide bond of the fusion protein. A linker peptide may be used in between the protein antigen and the carrier protein for allowing independent folding of the protein antigen domain and the carrier protein domain of the fusion protein. WO2007031339 describes how protein antigen as a recombinant protein co-expressed as a fusion protein with plant viral coat protein. Coat protein domains may then assemble, optionally in the presence of free viral coat protein, to form plant viral particles displaying on their surface protein antigen domains.

The immunogenic carrier protein preferably does not have similarity to the HER2 protein. Thus, the carrier protein does preferably not have an amino acid sequence segment of 50 or more, preferably of 30 or more, more preferably of 20 or more, and even more preferably of 10 or more contiguous amino acid residues, which sequence segment has an amino acid sequence identity of more than 50% to any sequence portion of identical length (in terms of number of amino acid residues) of SEQ ID NO: 18.

Conjugation of the protein antigen and the carrier by one or more covalent bonds is described next. Covalent linking of two or more different proteins or peptides can be achieved using several well-known approaches. These are not limited to: translational fusion; intein-mediated cis- or trans-splicing, hetero-oligomeric proteins assembly via disulfide bonds formation, chemical conjugation using cross-linking agents. One of the most commonly used approaches is translational (in-frame) fusion of proteins of interest or fragments thereof, where they are expressed from one transcriptional unit under control of single promoter. Generation of translational fusions between different proteins or parts thereof is well-known prior art and can be carried out using standard molecular biology techniques (Sambroock, J., Fritsch, E. F., Maniatis, T. 1989, *Molecular cloning: a Laboratory Manual. Cold Spring Harbor Laboratory*, New York). The approach is frequently used for improving expression and facilitating purification of recombinant proteins (Butt, T. R., Edavettal, S. C., Hall, J. P. et al., 2005, *Protein Expr. Purif.*, 43:1-9; Fazen, C. H., Kahkoska, A. R, Doyle, R. P., 2012, *Protein Expr. Purif.*, 85:51-59; for review see: Lichty, J. J., Malecki, J. L., Agnew, H. D., et al., 2011, *Protein Expr. Purif.*, September 3. [Epub ahead of print]), determining tissue-, cell- or subcellular compartmentalization of the proteins of interest or studying their interactions (e.g. GFP or GUS reporter gene fusions-Sepulveda-Garcia, E. & Rocha-Sosa, M. 2012, *Plant Sci.*, 195:36-47; Ahn, C. S., Han, J. A. & Pai, H. S. 2012, Planta, September 22, [Epub ahead of print]) or for any other applications like fusing heterologous domains for making chimaeric proteins (Meng, Z. F., Wang, H. J., Yao, X. et al., 2012, *Chin. Med. J.*, 125:3266-3272; Eon-Duval, A., Valax, P., Solacroup, T. et al., 2012, *J Pharm Sci.*, 101:3604-3618).

Covalent in-frame fusion of two or more different proteins or protein fragments can be achieved by using intein-mediated trans-splicing. Inteins were first identified as protein sequences embedded in-frame within protein precursor and excised during protein maturation process (Perler, F. B., Davis, E. O., Dean, G. E. et al., 1994, *Nucleic Acids Res.*, 22:1125-1127; Perler, F. B., 1998, Cell, 92:1-4). All information and catalytic groups necessary to perform a self-splicing reaction reside in the intein and two flanking amino acids. The chemical mechanism of protein splicing is described in detail by Perler and colleagues (1997, *Curr. Opin. Chem. Biol.*, 1:292-299) and by Shao & Kent (1997, *Chem. Biol.*, 4:187-194). Inteins usually consist of N-and C-terminal splicing regions and central homing endonuclease region or small linker region. Over 100 inteins are known so far that are distributed among the nuclear and organellar genomes of different organisms including eukaryotes, archaebacteria and eubacteria. Engineering of split inteins is described for example in Brenzel, S., Kurpiers, T. & Mootz, H. D. 2006, Biochemistry, 45:1571-1578). Finding of new natural split inteins is described in Carvajal-Vallejos, P., Pallisse, R., Mootz, H. D. et al., 2012, *J. Biol. Chem.*, 287:28686-96. It was shown that intein molecules are capable of trans-splicing. The removal of the central homing endonuclease region does not have any effect on intein self-splicing. This also made possible the design of trans-splicing systems, in which the N-terminal and C-terminal fragments of intein are co-expressed as separate fragments and, when fused to exteins (protein fragments, being ligated together with the help of intein), can perform trans-splicing in vivo (Shingledecker, K., Jiang, S. Q. & Paulus, H., 1998, *Gene*, 207:187-195). It was also demonstrated with N-and C-terminal segments of the Mycobacterium tuberculosis RecA intein, that protein trans-splicing could take place in vitro (Mills, K. V., Lew, B. M., Jiang, S., et al., 1998, *Proc. Natl. Acad. Sci. USA*, 95:3543-3548). This phenomenon was also identified for DnaE protein of Synechocystis sp. strain PCC6803 (Wu, H., Hu, Z. & Liu, X. Q., 1998, *Proc. Natl. Acad. Sci. USA*, 95:9226-9231). Two different genes located more than 700 Kb. p. apart on opposite DNA strands encode this protein. It was also shown that two intein sequences encoded by those genes reconstitute a split mini-intein and are able to mediate protein trans-splicing activity when tested in *Esherichia coli* cells. The intein molecule of the same origin (DnaE intein from *Synechocystis* sp. strain PCC6803) was used to produce functional herbicide-resistant acetolactate synthase 11 from two unlined fragments (Sun, L., Ghosh, I., Paulus, H. et al., 2001, Appl. Environ. Microbiol., 67:1025-29) and 5-enolpyruvylshikimate-3-phosphate synthase (EPSPS) (Chen, L., Pradhan, S. & Evans, T. C., 2001, *Gene,* 263;39-48)in *E coli.*

Yet another way of linking two or more polypeptides together is their assembly via disulfide bond formation. The easiest way to achieve this is to use fragments of proteins that are known to interact between each other and, preferably, to form disulfide bonds. Examples of such fragments are the constant regions of immunoglobulin light (e.g. "kappa" or "lambda") and heavy (e.g. Fc of IgG) chains. This approach can be used for formation of homodimers consisting of antigen fusion to constant regions heavy chain (U.S. Pat. No. 7,067,110) and for bi-specific IgG design (Zuo, Z., Jimenez, X., Witte, L. & Zhu, Z. 2000, *Protein Eng.,* 13:361-367; Davis, J. H., Aperlo, C., Li, Y. et al., 2010, *Protein Eng. Des. Sel.,* 23:195-202; for review see Carter, P. 2001, *J. Immunol. Methods,* 248:7-150; Thakur, A., Lum, L. G. 2010, *Curr. Opin. Mol. Ther.,* 12:340-3490).

The most universal approach for covalently linking two or more different proteins is to use chemical cross-linking agents, which is preferred for linking the protein antigen and the carrier protein in the present invention. Various known cross-linking agents can be applied for this purpose. Frequently employed cross-linking agents are glutaraldehyde (Maloney, D. G., Kaminski, M. S., Burowski, D. et. al., 1985, *Hybridoma,* 4:192-209; Timmerman, J. M. & Levy, R., 2000, *J. Immunol.,* 164:4797-47803; Bendandi, M., Gocke, C. D., Kobrin, C. B. et. al., 1999, *Nat. Med.,* 5:1171-1177; Bendandi, M., Marillonnet, S., Kandzia, R. et. al., 2010, *Ann. Oncol.,* 21:2420-2427), maleimide (Betting, D. J., Kafi, K., Abdollah-Fard, A. et al., 2008, *J. Immunol.,* 181:4131-4140; Kafi, K., Betting, D. J., Yamada, R. E. et. al., 2009, *Mol. Immunol.,* 46:448-4560) and many others. Glutaraldehyde cross-links proteins primarily via lysine residues, with secondary reactions at cysteine, tyrosine, and histidine residues (Migneault, I., Dartiguenave, C., Bertrand, M. J. & Waldron, K. C., 2004, *Biotechniques,* 37:790-796). Maleimide acts on (reduced) cysteine sulfhydryl groups (Betting, D. J., Kafi, K., Abdollah-Fard, A. et al., 2008, *J. Immunol.,* 181:4131-4140). Techniques of cross-linking as well as numerous cross-linking agents are well-known to those familiar with the art and are described in many reviews and protocols (Wong, S. S. & Wong, L. J. 1993, *Enzyme Microb. Technol.,* 14:866-874; Wong, S. S. & Jameson, D. M. 2009, *Chemistry of Protein and Nucleic Acid Cross-Linking and Conjugation,* CRC Press, Second Edition; *Thermo Scientific Pierce Crosslinking Technical Handbook,* 2009, Thermo Scientific; for downloading more info or protocols—www.thermo.com/pierce). Gross-linking agents are also commercially available and the protocols for cross-linking proteins of the manufacturer may be followed. Thus, in such embodiment, the protein conjugate may be produced by a process comprising providing the protein antigen and the immunogenic carrier as separate protein molecules and cross-linking the protein antigen and the immunogenic carrier via a linker using a chemical cross-linking agent such as glutaraldehyde.

The kit of the invention comprises the protein antigen as defined herein and an immunogenic protein or protein aggregate for cross-linking with said protein antigen for forming the protein conjugate. The kit may further contain a chemical cross-linking agent.

The protein conjugate obtained as described above is generally stored in an aqueous medium. For longer storage times, it may be frozen or lyophilized. The aqueous medium may contain a buffer to control the pH and may contain physiologic saline and/or other additives.

The anti-cancer vaccine of the invention contains the protein conjugate of the invention and suitable pharmacologically acceptable excipients. In another embodiment, the anti-cancer vaccine contains the protein antigen, whereby the protein antigen may not be covalently linked to an immunogenic carrier or an immunogenic carrier protein, and suitable pharmacologically acceptable excipients. The invention also provides a vaccine comprising a protein antigen as described herein, wherein the protein antigen of item (ii) or item (iii) is capable of providing protection against a HER-2/Neu-positive cancer, in particular therapeutic protection after tumor formation as determined in the Balb-NeuT metastatic breast cancer model.

As the anti-cancer vaccine is generally administered to patients by injection, the anti-cancer vaccine is generally a liquid aqueous formulation. However, the anti-cancer vaccine may also be in solid form such as in a lyophilized form to be reconstituted with an aqueous medium before administration. Examples for excipients include, without limitation, sterile aqueous solutions, suspensions, and emulsions. Aqueous excipients include, without limitation, water, alcohol, saline, and buffered solutions. Preservatives and other additives such as, for example, antimicrobials, anti-oxidants, chelating agents may also be present.

Similarly as described in U.S. Pat. No. 8,222,214, the anti-cancer vaccine can comprise agents that enhance the protective efficacy of the vaccine, such as adjuvants. Adjuvants include any compound or compounds that act to increase a protective immune response to the protein conjugate, thereby reducing the quantity of antigen necessary in the vaccine, and/or the frequency of administration necessary to generate a protective immune response. Adjuvants can include for example, emulsifiers, muramyl dipeptides, pyridine, aqueous adjuvants such as aluminum hydroxide, aluminum salts, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), *Mycobacterial phlei* (*M. phlei*) cell wall extract (MCWE) (U.S. Pat. No. 4,744,984), *M. phlei* DNA (M-DNA), and M-DNA-*M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, or soybean oil. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof. GM-CSF is preferred as a cytokine.

The anti-cancer vaccine of the invention can be used for treating or preventing HER-2/Neu-positive cancer in mammals, preferably in humans. Treating HER-2/Neu-positive cancer is preferred over prevention thereof. Treatment means that the vaccine is administered to a subject having the cancer. Preferred anti-cancer vaccines of the invention have a therapeutic effect, which means that further development of a HER-2/Neu-positive cancer can be prevented or slowed down even if the vaccine is administered when the cancer has already formed in the patient. In the examples, therapy is investigated and demonstrated in experiments referred to as "therapeutic setting". Many different types of cancers can be HER-2/Neu-positive, such as breast, liver, kidney, pancreatic, ovarian, prostate, gastric, colon, colorectal, bladder, testicular, stomach, esophageal or thyroid cancer. Detection of the HER2 gene or protein in these cancers may be e.g. by an immune reaction in biopsies using anti-HER-2/Neu monoclonal or polyclonal antibodies or by determining expressed RNA from the HER2 gene. Amplification of the HER2 gene was tested in *Science* 235 (1987) 177-182 and correlated with the prognosis of breast cancer.

When treating a HER-2/Neu-positive cancer in a patient suffering from such cancer, the anti-cancer vaccine is administered to the patient. Administration of the vaccine can be by infusion or injection (e.g., intravenously, intramuscularly, intracutaneously, subcutaneously, intrathecal, intraduodenally, intraperitoneally, and the like). Preferably, the compositions or vaccines are administered by intradermal injection.

The anti-cancer vaccine is administered to a patient in a therapeutically effective amount. The amount depends on the several variables such as the size or weight of the patient and condition of the patient. Toxicity and therapeutic efficacy of the vaccine can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Data obtained from cell culture assays and animal studies can be used in formulating a range of dosage for use in patients. The dosage of such vaccine compositions lies preferably within a range of circulating concentrations that include the ED50 with little or no toxicity. The dosage can vary within this range depending upon the dosage form employed and the route of administration utilized.

The vaccine can be administered to a patient on any schedule appropriate to induce and/or sustain protective immunity against the cancer, and more specifically to induce and/or sustain a humoral and preferably a cytotoxic T lymphocyte response to the protein antigen. For example, patients can be administered a vaccine composition as a primary immunization as described and exemplified herein, followed by administration of a booster to bolster and/or maintain the protective immunity. In some aspects, patients can be administered the vaccine compositions 1, 2 or more times per month. Once per month for six consecutive months is preferred to establish the protective immune response, particularly with respect to the primary immunization schedule. In some aspects, boosters can be administered at regular intervals such as every 6 or more months after completion of the primary immunization schedule. Administration of the booster may be every 6 months. The vaccine administration schedule, including primary immunization and booster administration, can continue as long as needed for the patient, for example, over the course of several years, to over the lifetime of the patient. In some aspects, the vaccine schedule includes more frequent administration at the beginning of the vaccine regimen, and includes less frequent administration (e.g., boosters) over time to maintain the protective immunity.

The vaccine of the invention may be administered to a human patient in a dosage of from 0.1 mg to 50 mg of the sequence segment of 300 or more contiguous amino acids from the ECD of the HER2 protein or of the variant sequence segment of the protein antigen per administration. Such dosage may also be used in subsequent administrations.

EXAMPLES

In the following, the invention is further illustrated using examples. The invention is, however, not limited to these examples.

Example 1

Construct Design

The Her2-ED44 sequence of rat (GenBank accession no.: NP_058699, amino acid residues 314–657=344 residues, FIG. 1-2) was generated using PCR from the respective cDNA by adding flanking BsaI sites and removing two internal BsaI sites. The human HER2-ED44 sequence (GenBank accession no.: AAA75493, amino acid residues 310-653=344 residues, FIG. 1-2) was generated using gene synthesis with the codon usage of *Nicotiana tabacum*. From the rat and human Her2-ED44, different versions (modules) were generated using PCR. These modules differ in the overhangs created by the flanking BsaI restriction sites which will be used for cloning (FIG. 4-9).

Fragment C serves as immunogenic carrier protein in the vaccine which aids to break the self-tolerance for HER2. Tetanus toxin is a potent neurotoxin produced by *Clostridium tetani* the causative agent of tetanus. Fragment C is a non-toxic C-terminal portion of the Tetanus toxin which confers binding to neurons (Swiss-Prot accession no.: PO4958, amino acid residues 865–1315=451 residues). The Tetanus toxin fragment C sequence was generated by gene synthesis. Also here, from the originally synthesized fragment C sequence different modules were generated using PCR (FIG. 10-11).

The Her2-ED44 and Tetanus toxin fragment C modules were cloned in TMV-based viral expression vectors (magnICON® system, see below) using the Type IIS restriction enzyme BsaI which generates different, customized overhangs for each module and thereby allowing assembly of the final construct by removing these restriction sites (Engler, C., Kandzia, R. & Marillonnet, S. 2008, *PLoS One,* 3:e3647; FIG. 4, FIG. 7, FIG. 10). The TMV-based viral vector constructs also contained a rice α-amylase 3A signal peptide (Swiss-Prot accession no.: P27932) which is cleaved off in planta and serves to deliver the protein of interest in the plant apoplast where it accumulates. The rice α-amylase signal peptide was amplified from *Oryza sativa* genomic DNA and the last two amino acids of the signal peptide modified from HA to SG (wild type: MGKQMAALCGFLLVALLWLTPDVAHA, SEQ ID NO: 19; modified: MGKQMAALCGFLLVALLWLTPDVASG, SEQ ID NO: 20) due to cloning reasons. Additionally, Her2-ED44 and Tetanus toxin fragment C were fused to a (GGGGS)$_3$ (SEQ ID NO: 21) linker and a 6x His tag or human kappa light chain constant region (Swiss-Prot accession no.: P01834) which was optimized by gene synthesis for N. tabacum codon usage (FIG. 4-11).

As an alternative immunogenic carrier, Tobacco Mosaic Virus (TMV) particles were used. TMV particles have a rod-like structure of approximately 300 nm in length and 18 nm in diameter. The particles are built of coat protein (CP) subunits which assemble around the genomic, single-stranded RNA of the virus. To improve the conjugation efficiency by glutardialdehyde, the coat protein was modified. The N-terminal modification of the TVCV coat protein (Swiss-Prot accession no.: Q88922), i.e. addition of 4 amino acid residues ADFK, was introduced in the wild-type sequence by PCR (primer sequence, SEQ ID NO: 32: TTT GGTCTC A AATG GCT GAC TTT AAG AGC TAT AAC ATC ACG AAT CCT AAC C; BsaI restriction site, generated overhang, introduced additional codons). The resulting DNA module encoding the CP$_{Lys}$ protein was also cloned into a magnICON® TMV-based viral expression vector using the type IIS enzyme BsaI (FIG. 12).

Viral binary expression vectors were developed based on the magnICON® technology (Gleba, Y., Klimyuk, V. & Marillonnet, S., 2005, *Vaccine,* 2005, 23:2042-2048; Gleba, Y., Klimyuk, V. & Marillonnet, S. 2007, *Curr. Opin. Biotechnol.,* 18:134-141) using elements from Tobamo viruses (Tobacco Mosaic Virus, TMV), i.e. from the cDNAs of two closely related plant viruses, TVCV (turnip vein clearing virus; Lartey, R. T., Lane, L. C. & Melcher, U. 1994, *Arch. Virol.,* 138:287-298; Lartey, R. T., Voss, T. C. & Melcher, U. 1995, *Gene,* 166:331-332) and crTMV (crucifer-infecting tobamovirus; Dorokhov, Y. L., Ivanov, P. A., Novikov, V. K., et al., 1994, *FEBS Lett.,* 350:5-8). The resulting vectors are called 'TMV-based', since both parental viruses are tobamoviruses and related to the well-known tobacco mosaic virus (TMV). All three viruses (TVCV, crTMV and TMV) are positive-strand RNA viruses and have the same overall structure and mode of replication. Basically, the viruses encode an RNA-dependent RNA polymerase (RdRP), the Movement Protein (MP) and the Coat Protein (CP). The RdRP replicates the full viral RNA transcript (genomic RNA) as well as the two subgenomic RNAs (sgRNAs) that are required for expression of the two other viral proteins, MP and CP. The MP is required for short distance cell-to-cell movement of the viral genomic RNA within the infiltrated leaf. The CP is required for formation of viral particles and long distance systemic movement from leaf to leaf via the vascular system. Formation of viral particles is not required for cell-to-cell movement. Therefore, the CP was eliminated from the viral vectors and replaced with the gene of interest. Thus, the viral vector is unable to produce viral particles and the gene of interest is expressed at higher levels. In addition to the viral proteins and the gene of interest, the viral vector must also contain the 5' and 3' non-translated (5' ntr and 3' ntr) viral sequences which are essential for replication (Marillonnet, S., Giritch, A., Gils, M. et al., 2004, *Proc. Natl. Acad. Sci. USA.,* 101:6852-7; FIG. 13).

For efficient expression of the TMV-based viral vector in plant cells, the cDNA of the viral vector has been cloned between a plant promoter and a plant terminator (Act2 and nos) (Marillonnet, S., Giritch, A., Gils, M. et al., 2004, *Proc. Natl. Acad. Sci. USA.,* 101:6852-6857) and plant introns were added within the RdRP and MP sequences (Marillonnet, S., Thoeringer, C., Kandzia, R. et al., 2005, *Nat. Biotechnol.,* 23:718-723). For efficient delivery of TMV-based viral vectors to plant cells, we use *Agrobacterium tumefaciens*. Therefore, the complete viral vector (plant promoter, TMV-based viral vector sequences with gene of interest, plant terminator) has been cloned between the T-DNA left and right borders of a binary vector. The elements of the binary vector are a pVS1 origin (Hajdukiewicz, P., Svab, Z. & Maliga, P., 1994, *Plant Mol Biol.,* 25:989-994) for plasmid replication in *Agrobacterium*, a co/E1origin for plasmid replication in *E. coli*, a nptIII kanamycin antibiotic resistance gene (Frisch, D. A., Harris-Haller, L. W., Yokubaitis, N. T. et al., 1995, *Plant Mol. Biol.,* 27:405-409) and T-DNA left and right borders (Frisch, D. A., Harris-Haller, L. W., Yokubaitis, N. T. et al., 1995, *Plant Mol. Biol.,* 27:405-409) to delimitate the ends the DNA transferred to plant cells. To facilitate blue/white selection a lacZα cassette amplified from pUC19 was inserted between two BsaI restriction sites which allow seamless in frame cloning of the gene of interest. Therefore, during initial construction of the viral vectors, all naturally occurring BsaI recognition sites were removed to allow easy and robust cloning of the gene of interest (FIG. 13).

Example 2

Expression, Purification and Coniuqation of Vaccine Components

Heteroloqous Expression of Her2-ED44-hKappa, Her2-ED44-His, Tetanus-Toxin-Fraqment—C-hKappa and TMV Particles in *N. benthamiana* Plants (maqnICON® System)

For production of the recombinant proteins, the selected *Agrobacterium* strain harboring the TMV-based expression vector is grown in liquid LBS medium with soya peptone (Duchefa Biochemie, Haarlem, The Netherlands) replacing tryptone, and supplemented with 50 µg/mL rifampicin and 50 µg/mL kanamycin. Agrobacterial cultures are grown at 28° C. until OD$_{600}$ reaches 2 to 4. Infiltration solution is prepared by diluting the agrobacterial culture in infiltration buffer (10 mM MES, pH 5.5, 10 mM MgSO$_4$) to a defined cell concentration (equivalent to a 200-fold dilution of a culture with OD$_{600}$ of 1.0).

About 40 to 80 *Nicotiana benthamiana* plants (5 to 10 for harvest of TMV particles), grown under controlled and standardized conditions for 6-8 weeks, are vacuum-infiltrated with the agrobacterial infiltration solution and then kept in the greenhouse for 7-12 days for expression and accumulation of the recombinant protein. Plant leaves are then harvested, ground in liquid nitrogen to a fine leaf powder and kept at −80° C. until protein extraction followed by purification.

Purification of Her2-ED44-His-Tag Using Ni-NTI Affinity Chromatography

The leaf powder (0.6 to 1 kg) is extracted in 20 mM sodium phosphate, pH 6.0, 0.5 M NaCl, 10 mM imidazole with approximately two volumes (w/v) of extraction buffer. The extraction is performed at +4° C. by shaking for 40 minutes. The homogenate is clarified by centrifugation at 15.000×g for 10 minutes followed by filtration through MiraCloth filter. The pelleted plant tissue is re-extracted using the same extraction conditions. The extracts are combined and subjected to pH adjustment. The pH of the clarified homogenate is lowered to 5.0 using 5N HCL for removal of host cell proteins including Rubisco. After incubation at pH 5 with stirring for about 30 minutes, the pH of the crude extract is re-adjusted to pH 7.4 with 5N NaOH. The crude extract is then centrifuged (20.000×g for 15 minutes) to remove cell debris and precipitates. Before applying the crude extract to the affinity chromatography column, the crude extract is filtered through several filtration membranes (20 μm-8 μm-3 μm-0.45 μm). The clear filtrate is applied onto a 5 mm HisTrap™ FF column (GE Healthcare, 17-5255-01), which was equilibrated with 20 CV washing buffer (20 mM sodium phosphate pH 7.5, 0.5 M NaCl, 20 mM imidazole). After loading, the column is washed with 20 CV of washing buffer. Her2-ED44-His is eluted with 20 CV elution buffer (20 mM sodium phosphate pH 7.5, 0.5 M NaCL, 0.5 M imidazole).

A polishing step is applied to remove DNA, host cell proteins and endotoxins. The eluted Her2-ED44-His solution is subjected to a SartobindQ® SingleSep mini capsule (Sartorius, #921EXQ42D4-SS), which is a strong basic anion exchanger. The SartobindQ® SingleSep mini capsule is sanitized with 1 N NaOH followed by equilibration with PBS pH 5.0. Before loading the Her2-ED44-His eluate onto SartobindQ® SingleSep mini capsule, the pH of Her2-ED44-His eluate is adjusted to pH5.0 using 5 N HCL. The flow-through of SartobindQ® SingleSep mini capsule is collected and the capsule is washed with PBS buffer, pH 5.0, until base line UV280 nm is reached. The purified Her2-ED44-His is concentrated using Spin-X UF concentrator 30 k MWCO (Corning, #431489). Finally, the concentrate is sterile-filtrated using 0.2 μm filter.

The protein concentration of purified Her2-ED44-His is determined using BCA protein assay kit (Thermo Scientific, #23225). Immunoblotting analysis of His-tagged Her2-ED44 was carried out using a primary anti-tetra-His antibody (QIAGEN, #34670) and secondary anti-mouse-IgG-horse radish peroxidase conjugate (Sigma Aldrich, A4416). Endotoxin determination was carried out using the Endosafe®-PTS system (Charles River Laboratories, #PTS100) with Endosafe® PTS cartridges, sensitivity 10-0.1 EU/ml (Charles River Laboratories, #PTS201).

Purification Her2-ED44-Kappa and Tetanus Toxin Fragment C-Kappa Using Affinity Chromatography on KappaSelect For protein extraction, the frozen leaf powder (appr. 600 g to 1 kg) is mixed with approximately two volumes (w/v) of extraction buffer (200 mM sodium citrate, pH6, 5 mM EDTA) and incubated with shaking for about 40 minutes. The homogenate is clarified by centrifugation at 15.000×g for 10 minutes followed by filtration through MiraCloth filter. The extraction was repeated to ensure the maximal yield of expressed recombinant protein.

The pH of the clarified homogenate is then lowered to pH 5.0 using sodium citrate solution for removal of host cell proteins including Rubisco. After incubation at pH5 for about 30 minutes, the pH of the crude extract is re-adjusted with 5 N NaOH to pH 7.4. The extract is centrifuged at 20.000×g for 15 minutes to remove precipitates and cell debris and subsequently filtered through several membrane filters (20 μm-8 μm-3 μm and 0.45 μm) to obtain an extract suitable for subsequent column chromatography.

All chromatography steps are carried out at room temperature using a GE Healthcare ÄKTA Purifier Chromatography System. Affinity chromatography with KappaSelect (GE Healthcare, 17-5458-01) is performed to purify recombinant fusion proteins containing a Kappa constant region as purification tag.

The column material is equilibrated with 20 column (CV) volumes PBS pH7.34 prior loading the filtered protein extract. After loading, the column is washed with 20 CV wash buffer PBS, pH7.34. Column-bound protein is eluted with a low pH buffer (0.1 M Glycine pH2.9) via a peak-based fractionation and adjusted to a neutral pH with 0.4 M Na$_2$HPO4.

After KappaSelect affinity chromatography, the eluate is further purified (polishing step) on a SartobindQ®SingleSep mini capsule, a strong basic anion exchanger (Sartorius, #921EXQ42D4-SS). The SartoBinQ column was sanitized with 1 N NaOH, followed by equilibration with PBS pH5.0 before use. The pH of eluate was adjusted to 4.8 before loading into SartoBindQ column. The flow-though was collected and column was washed with PBS buffer (pH5.0) until base line UV280 nm is reached.

The purified Her2-ED44-Kappa was concentrated using Spin-X UF concentrator 30 k MWCO (Corning, #431489) and purified Tetanus Toxin Fragment C-Kappa was concentrated using Spin-X UF concentrator 50 k MWCO (Corning, #431490). The concentrate was then sterile-filtrated using 0.2 μm filter. The concentration of purified protein is determined using BCA protein assay kit (Thermo Scientific, #23225). Endotoxin determination was carried out using the Endosafe®-PTS system (Charles River Laboratories, #PTS100) with Endosafe®PTS cartridges, sensitivity 10-0.1 EU/ml (Charles River Laboratories, #PTS201).

Purification of TMV Virus Particles

The frozen leaf powder is mixed with 3-5 volumes (w/v) of 0.1 M potassium phosphate buffer, pH7.0. The homogenate is incubated on ice on a shaker for approximately 30 minutes. Then, the homogenate is filtered through a MiraCloth filter into a prechilled tube. The filtrate is transferred into centrifuge tubes, 1/4 volume of chloroform is added and the solution is gently but thoroughly mixed for 20 minutes on ice. The mixture is centrifuged at 10,000×g for 15 minutes at 4° C. The upper aqueous phase is transferred into a fresh centrifugation tube and 1/10 volume of 12% sodium chloride and 1/5 volume of 25% PEG-6000 is added. The mixture is incubated on ice for approximately 1 hour and centrifuged at 10,000×g for 15 minutes at 4° C. The supernatant is carefully removed and 1/5 volume of 0.1 M potassium phosphate buffer, pH 7.0 is added. Finally, the mixture is incubated on ice until the pellet is dissolved. Quality of the viral particles is analyzed by SDS-PAGE. Approximately 12 mg purified TMV particles can be obtained from 6 g fresh leaf material.

Conjugation of Her2-EC-Kappa with Tetanus Toxin-Fragment-C-Kappa or TMV Virus Particles Using Glutaraldehyde Her2-ED44-Kappa and Tetanus toxin Fragment C-Kappa or TMV viral particles are mixed (3 mg of each) for the conjugation reaction. Glutardialdehyde (25%) is added to the protein mixture to a final concentration of 0.1%. The mixture is incubated at room temperature for 2 hours and gently stirring. The reaction is stopped by addition of 2M glycine to a final concentration of 20 mM and incubation is continued for 30 minutes. The entire reaction is subjected to gel filtration for removal of remaining glutardialdehyde and non-conjugated proteins. The maximal volume of 2 ml of the reaction mixture was loaded onto a Superdex™ 200 column (GE Healthcare, #17-1043-02) with a flow rate of 1 ml/min. The mobile phase is PBS buffer pH 7.34 and the flow through was collected in 10 fractions over the entire peaks areas. The conjugation efficiency is analyzed (15 µl of each fraction) by 8% SDS-PAGE under reducing conditions and immunoblot analysis using anti-human Kappa antibodies (SigmaAldrich, #A7164). All conjugate containing fractions (molecular weight >70 kDa) were pooled and concentrated using Spin-X UF concentrator 50 k MWCO (Corning, #431490). Protein concentration of conjugate is determined using BCA protein assay kit (Thermo scientific #23225). Endotoxin determination was carried out using the Endosafe®-PTS system (Charles River Laboratories, #PTS100) with Endosafe®PTS cartridges, sensitivity 10-0.1 EU/ml (Charles River Laboratories, #PTS201).

Example 3

Mice and Experimental Protocol

BALB/c female mice aged between 6 and 10 weeks at the beginning of the procedures were kept in accordance with the Home Office Guidelines. Experiments were performed under Project Licence JR 70/6401 or AM 30/3028 and Personal Licence PIL 70/20084 (UoS). Mice are injected with 50 µg of Her2-ED44-His or conjugate vaccines containing an equivalent amount of Her2-ED44. Each mouse received either 50 µg of Her2-ED44, or 130 microgram of Her2-ED44-kappa-Fragment C-kappa, or 91 µg of Her2-ED44-kappa-TMV in 100 µL saline combined with an equal volume of alum adjuvant (Sigma). Before injections vaccines combined with alum were mixed end-over-end for 1 h at ambient temperature. The injections are carried out subcutaneously into two sites in the flank. At least five mice per group were vaccinated per each experiment, except of Balb-NeuT where the group sizes were smaller. For the control vaccine 130 µg of plant expressed irrelevant protein (5T33lg-hkappa-Fragment C fusion protein made by ICON) was given. A comparator vaccine, Her2/Neu-EC-TM DNA vaccine (50 µg), was injected intramuscularly into two site. Wild-type mice are injected twice with the same amount of vaccine, second injection was given three weeks after the first one (FIG. 14). The mice were bled 3 weeks after the first injection and two times after second injection with two weeks interval between the bleeds (week 5 and week 7). Balb-NeuT transgenic mice were vaccinated 5 times with the first injection given at 10 weeks of age with the subsequent injection given every three weeks. Blood samples were taken 2 weeks after each injection. The samples were analysed by ELISA for reactivity against Her2-ED44 and for reactivity against membrane bound Her2/neu as well as for IgG isotypes and affinity.

Serial Blood Sampling

To detect vaccine-induced antibody responses, blood samples were taken from vaccinated mice by tail bleeding. Local anesthetic (Instillagal®, FARCO-PHARMA GmbH, Cologne, Germany) was applied to the tip of the tails and mice were warmed at 37° C. for 5 min. A 1-2 mm section of the tip of the tail was cut with a scalpel and up to 200 µL of blood was removed per mouse. After clotting, whole blood was spun at 10,000 rpm for 10 minutes and the serum was collected. Serum samples were preserved by the addition of 1 mL of 1 mM sodium azide and store at −20° C.

Evaluation of Anti-Her2-ED44 Levels of Total IqG Antibody and Antibody Isotypes by ELISA For ELISA, 96-well flat bottomed Nunc Immunos™ ELISA plates (NUNC) were coated with Her2-ED44-His (3 µg/mL in carbonate/bicarbonate buffer pH 9.6) overnight. The following day the plates were blocked with 1% BSA in PBS for 1 h at ambient temperature. Serial 4× dilutions of samples ranging from 1/100 to 1/6400 for week 3 samples and ranging from 1/1000 to 1/64000 for every subsequent time point were added to the plates and incubated for 1.5 h on a shaker at 37° C. After 4 times washing with PBS/0.1% Tween 20 (Sigma # p1379) the detection anti-mouse IgG antibody labeled with horseradish peroxidase (The Binding site, Birmingham, UK; # AP272; dilution 1/1000 ) was incubated with the plates for 1.5 h. Following another 4 washes with PBS/0.1% Tween the o-phenylenediamine dihydrochloride substrate (Sigma, # P4664) was added and the reaction was allowed to develop and then stopped by the addition of 2.5 M $H_2SO_4$. The optical density was measured at 490 nm using a Dynex MRX Plate reader. The results of the measurements are shown in FIGS. 15A; 18B; 20 and 21B.

For antibody isotype evaluation a similar protocol was applied but a different detection antibody was used as following anti-IgG1 (Biorbyt Ltd., Cat. No. orb27074), anti-IgG2a (Serotec # STAR13313, dilution 1/4000) and anti-IgG2b (Harlan Sera-Lab ltd# SBA 1090-05; dilution 1/1000). The serum antibody levels were calculated from a standard curve and expressed as arbitrary units per mL (FIG. 15, panel B).

Mammalian Carcinoma Cell Lines

TUBO cells are a cloned line derived from BALB/c mice which are transgenic for the transforming r-Her-2/neu oncogene (BALB-NeuT) (Rovero, 2000) and used in the binding assay to assess the reactivity with the rat Her2/neu. TUBO cells were cultured in DMEM high glucose (PAA Laboratories) supplemented with penicillin-streptomycin and 20% FCS. When the cells reach 60-70% confluency they are incubated with TRYPSIN-EDTA(PAA Laboratories, Pasching, Austria) for 5-10 minutes at 37° C. and then trypsin is stopped by split dilution. Splitting dilution can range from 1:3 to 1:6 or 1:8.

The D2F2/E2 cells belong to a mammary tumor line from BALB/c mice which has been stably transfected with a vector expressing the human ERBB2 (Her2/neu) gene (Piechocki, M. P., Pilon, S. A. & Wei, W. Z. 2001, J. Immunol., 167: 3367-3374). The D2F2/E2 cells were used in the binding assay to assess the reactivity with human Her2/neu. D2F2/E2 cell were cultured in high glucose DMEM supplemented with Penicillin-Streptomycin, 20% FCS and 800 µg/mL of G418 (Gibco). When confluent the cells were trypsinised and split by diluting between 1:4 and 1:8. For FACS analysis and tumour challenge experiments single cell suspensions are prepared by passing the cells through a syringe after trypsinisation.

Evaluation of Induced Mouse Antibody for Binding to Surface her2/Neu by FACS Analysis Binding of the induced antibody was analyzed by FACS staining using previously published protocols with modifications (Rovero, 2000). Briefly, 2×$10^5$ (either Tubo or D2F2/E2) cells were initially pre-incubated with serum from naïve mice to reduce non-specific binding and then with 1/100 dilution of the immune sera derived from vaccinated mice.

The staining was carried out in a total volume of 100 μL. Secondary anti-mouse F(ab')2 IgG labeled with eFluor660 (eBioscience#50-4010-82, dilution 1/200), was used to detect the levels of induced antibody binding with a subsequent FACS analysis using FACS Callibur and Cell Quest software. The results of the measurements are shown in FIGS. 16-18 and 20.

Tumour Challenge Experiments

Protection experiments were performed using the TUBO cell line or the D2F2/E2 cell line. After two doses of vaccines mice were challenged with $10^5$ tumor cells. The challenge was 4-6 weeks after the last vaccine injection. A group of mice which received no injections was used as an additional control. Mice were observed for the signs of tumours. Once tumours were visible they were measured every second day and mice with tumours ≥1.5 cm were humainly terminated. The survival graphs were produced using Graphpad PRISM 4.03 software. Statistical analysis to compare groups injected with different vaccines was performed using the Mann-Whitney test for non-parametric data.

Inhibition of Her2/Neu-Mediated Signaling by Antibodies Induced with Hu Her 2 ED44-FrC Conjugate Vaccine The human HER2 positive breast cancer cell line BT474 was incubated separately with pooled sera from mice vaccinated at dilutions indicated, trastuzumab (Herceptin®, Roche, UK) or 30 μM of P13K (downstream of Her2 signalling) inhibitor LY294002 (Cell Signalling Technology, Massachusetts, USA) for 1 hour. All treatments were carried out in complete DMEM media supplemented with 10% FCS at 37° C., 10% $CO_2$. After the incubation, the cells were harvested, lysed and 10 μg of protein per sample were subjected to SDS-PAGE (NuPAGE® Novex® 4-12% Bis-Tris Gels, Invitrogen Life Technologies, California, USA) after denaturing at 95° C. for 5 minutes. Following the electrophoresis, the proteins were transferred to a polyvinylidene difluoride (PVDF) membrane (Amersham Hybond™-P, GE Healthcare, Buckinghamshire, UK) and after blocking in 5% non-fat milk in Tris buffered saline (TBS) with 0.1% Tween 20, (TBS-T) were incubated sequentially with anti-pAkt (rabbit anti-phosphor-Akt (Ser473) antibody, Cell Signalling Technologies), Akt (rabbit anti-Akt antibody, Cell Signalling Technologies) or β-actin (mouse anti-human β-actin antibody, clone 2F1-1, BioLegend) antibody at 1/1,000 dilution. Before applying each subsequent antibody, the previous antibody was stripped. After washing 3 times with TBS-T prior the membranes were incubated with 1/1,000 in TBS-T of the HRP-conjugated secondary antibody (anti-rabbit IgG-HRP, Cell Signalling Technologies or anti-mouse IgG (Gamma) (AFF)-PEROX, The Binding Site, Birmingham, UK) for 1 hour at room temperature. The membrane was washed 3 times with TBS-T again before detection with the SuperSignal™ West Pico Chemiluminescent Substrate (Thermo Scientific, Illinois, USA). The chemiluminescent signal was captured using Bio-Rad imaging system (Fluor-S® Multilmager, Bio-Rad). The results of Western blotting are shown in FIG. 19.

Summary of Nucleotide and Amino Acid Sequences

SEQ ID NO: 1 Amino acid sequence of extracellular domain of human HER2 protein (amino acids 1 to 653 from GenBank AAA75493):

```
melaalcrwg lllallppga astqvctgtd mklrlpaspe thldmlrhly qgcqvvqgnl eltylptnas lsflqdiqev qgyvliahnq vrqvplqrlr ivrgtqlfed nyalavldng
```

-continued
```
dplnnttpvt gaspgglrel qlrslteilk ggvliqrnpq lcyqdtilwk difhknnqla ltlidtnrsr achpcspmck gsrcwgesse dcqsltrtvc aggcarckgp lptdccheqc aagctgpkhs dclaclhfnh sgicelhcpa lvtyntdtfe smpnpegryt fgascvtacp ynylstdvgs ctlvcplhnq evtaedgtqr cekcskpcar vcyglgmehl revravtsan iqefagckki fgslaflpes fdgdpasnta plqpeqlqvf etleeitgyl yisawpdslp dlsvfqnlqv irgrilhnga ysltlqglgi swlglrslre lgsglalihh nthlcfvhtv pwdqlfrnph qallhtanrp edecvgegla chqlcarghc wgpgptqcvn csqflrgqec veecrvlqgl preyvnarhc lpchpecqpq ngsvtcfgpe adqcvacahy kdppfcvarc psgvkpdlsy mpiwkfpdee gacqpcpinc thscvdlddk gcpaeqrasp lts
```

SEQ ID NO: 2 Amino acid sequence of human HER2-ED44 (amino acids 310-653 of human HER2/Neu.

SEQ ID NO: 3 Amino acid sequence of rat HER2-ED44 (amino acids 314-657 of rat HER2/Neu of GenBank accession no.: NP_058699

SEQ ID NO: 4 Shortened version of human Her2-ED44 which encompasses residues 312-649 of the human HER2/neu protein.

SEQ ID NO: 5 Shortened version of Her2-ED44 which encompasses amino acid residues 340-649 of the human HER2/neu protein.

SEQ ID NO: 6 rat Her2-ED44-His construct.

SEQ ID NO: 7 rat Her2-ED44-His.

SEQ ID NO: 8 rat Her2-ED44-kappa construct.

SEQ ID NO: 9 rat Her2-ED44-kappa.

SEQ ID NO: 10 human Her2-ED44-His construct.

SEQ ID NO: 11 human Her2-ED44-His.

SEQ ID NO: 12 human Her2-ED44-kappa construct.

SEQ ID NO: 13 human Her2-ED44-kappa.

SEQ ID NO: 14 Tetanus toxin fragment C-kappa construct.

SEQ ID NO: 15 Tetanus toxin fragment C-kappa.

SEQ ID NO: 16 TMV-$CP_{Lys}$ amino acid sequence.

SEQ ID NO: 17 Amino acid sequence of DOM1 domain of tetanus toxin fragment C

```
mgwsciiffl vatatgvhsk nldcwvdnee didvilkkst ilnldinndi isdisgfnss vitypdaqlv pgingkaihl vnnesseviv hkamdieynd mfnnftvsfw lrvpkvsash leqygtneys iissmkkhsl sigsgwsysl kgnnliwtlk dsagevrqit frdlpdkfna ylankwvfit itndrlssan lyingvlmgs aeitglgair ednnitlkld rcnnnnqyvs idkfrifcka lnpkeiekly tsyls
```

SEQ ID NO: 18 Amino acid sequence of human HER2 protein from GenBank AAA75493

```
   1 melaalcrwg lllallppga astqvctgtd mklrlpaspe thldmlrhly qgcqvvqgnl
  61 eltylptnas lsflqdiqev qgyvliahnq vrqvplqrlr ivrgtqlfed nyalavldng
 121 dplnnttpvt gaspgglrel qlrslteilk ggvliqrnpq lcyqdtilwk difhknnqla
 181 ltlidtnrsr achpcspmck gsrcwgesse dcqsltrtvc aggcarckgp lptdccheqc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph qallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gcpaeqrasp ltsivsavvg
 661 illvvvlgvv fgilikrrqq kirkytmrrl lqetelvepl tpsgampnqa qmrilketel
 721 rkvkvlgsga fgtvykgiwi pdgenvkipv aikvlrents pkankeilde ayvmagvgsp
 781 yvsrllgicl tstvqlvtql mpygclldhv renrgrlgsq dllnwcmqia kgmsyledvr
 841 lvhrdlaarn vlvkspnhvk itdfglarll dideteyhad ggkvpikwma lesilrrrft
 901 hqsdvwsygv tvwelmtfga kpydgipare ipdllekger lpqppictid vymimvkcwm
 961 idsecrprfr elvsefsrma rdpqrfvviq nedlgpaspl dstfyrslle dddmgdlvda
1021 eeylvpqqgf fcpdpapgag gmvhhrhrss strsgggdlt lglepseeea prsplapseg
1081 agsdvfdgdl gmgaakglqs lpthdpsplq rysedptvpl psetdgyvap ltcspqpeyv
1141 nqpdvrpqpp spregplpaa rpagatlera ktlspgkngv vkdvfafgga venpeyltpq
1201 ggaapqphpp pafspafdnl yywdqdpper gappstfkgt ptaenpeylg ldvpv
```

SEQ ID NO: 19 Wild-type rice α-amylase signal peptide.
SEQ ID NO: 20 modified rice α-amylase signal peptide.
SEQ ID NO: 21 (GGGGS)₃ linker.
SEQ ID NO: 22 primer for introducing ADFK into N-terminus of TVCV coat protein.

The content of European patent application No. 13 001 211.5 filed on Mar. 11, 2013 including description, claims and figures is incorporated by reference herein.

---

The invention claimed is:

1. A protein conjugate comprising a protein antigen and an immunogenic carrier covalently bonded to said protein antigen, wherein said protein antigen
has a sequence segment consisting of the amino acid sequence of SEQ ID NO: 2, and
wherein the amino acid sequence of the protein antigen comprises at most 344 contiguous amino acids of the amino acid sequence of SEQ ID NO: 1.

2. The protein conjugate according to claim 1, wherein said protein antigen or said protein conjugate does not contain a further amino acid sequence segment as follows:
a further amino acid sequence segment of 20 or more contiguous amino acid residues from amino acid 1 to 253, or from amino acid 670 to 1255, of SEQ ID NO: 18; or
a further amino acid sequence segment of more than 20 contiguous amino acid residues having more than 50% sequence identity to a sequence of contiguous amino acids from amino acid 1 to 253 or from amino acid 670 to 1255, of SEQ ID NO: 18.

3. The protein conjugate according to claim 1, wherein said protein antigen or said protein conjugate does not contain an amino acid sequence segment of 10 or more contiguous amino acid residues from the transmembrane domain or the intracellular domain of the Her2/neu protein of SEQ ID NO: 18.

4. The protein conjugate according to claim 1, wherein said protein antigen comprises, as a further segment, a purification tag at its N- or C-terminal end, and optionally a linker linking the purification tag and the sequence segment of the protein antigen.

5. The protein conjugate according to claim 1, wherein any further sequence segment of a length of at least 7 amino acid residues of said protein antigen has an amino acid sequence identity less than 50% to any sequence of contiguous amino acids of identical length of SEQ ID NO: 18.

6. The protein conjugate according to claim 1, wherein said immunogenic carrier is or comprises an immunogenic protein or an immunogenic protein aggregate.

7. The protein conjugate according to claim 1, wherein the immunogenic carrier protein does not have an amino acid sequence segment of 20 or more contiguous amino acid residues having an amino acid sequence identity of more than 50% to any sequence of contiguous amino acids of identical length of SEQ ID NO: 18.

8. The protein conjugate according to claim 1, wherein said protein antigen and said immunogenic carrier are covalently bonded by chemical cross-linking using a chemical cross-linking agent.

9. The protein conjugate according to claim 1, wherein said protein antigen elicits an immune response against the HER2 protein in a mammal, optionally comprising a further sequence segment,
wherein the protein antigen or said protein conjugate does not contain a further amino acid sequence segment of 20 or more continuous amino acids from amino acid 1 to 253, or from anion acids 670 to 1255, of SEQ ID NO:18;
and wherein said protein antigen and said immunogenic carrier are covalently bonded by chemical cross-linking using a chemical cross-linking agent.

10. An anti-cancer vaccine comprising the protein conjugate of claim 1 and water in which said protein conjugate is dispersed and, optionally, further comprising one or more pharmaceutically acceptable excipients.

11. An anti-cancer vaccine comprising the protein conjugate of claim 1 and an immunological adjuvant.

12. A process of producing the protein conjugate as defined in claim 1, comprising providing said protein antigen and cross-linking the protein antigen with said immunogenic carrier.

* * * * *

SEQUENCE LISTING

<160> NUMBER OF SEQ ID NOS: 18

<210> SEQ ID NO 1
<211> LENGTH: 653
<212> TYPE: PRT
<213> ORGANISM: Homo sapiens

<400> SEQUENCE: 1

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480
```

-continued

```
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser
                645                 650

<210> SEQ ID NO 2
<211> LENGTH: 344
<212> TYPE: PRT
<213> ORGANISM: Homo sapiens

<400> SEQUENCE: 2

Ser Cys Thr Leu Val Cys Pro Leu His Asn Gln Glu Val Thr Ala Glu
1               5                   10                  15
Asp Gly Thr Gln Arg Cys Glu Lys Cys Ser Lys Pro Cys Ala Arg Val
            20                  25                  30
Cys Tyr Gly Leu Gly Met Glu His Leu Arg Glu Val Arg Ala Val Thr
        35                  40                  45
Ser Ala Asn Ile Gln Glu Phe Ala Gly Cys Lys Lys Ile Phe Gly Ser
    50                  55                  60
Leu Ala Phe Leu Pro Glu Ser Phe Asp Gly Asp Pro Ala Ser Asn Thr
65                  70                  75                  80
Ala Pro Leu Gln Pro Glu Gln Leu Gln Val Phe Glu Thr Leu Glu Glu
                85                  90                  95
Ile Thr Gly Tyr Leu Tyr Ile Ser Ala Trp Pro Asp Ser Leu Pro Asp
            100                 105                 110
Leu Ser Val Phe Gln Asn Leu Gln Val Ile Arg Gly Arg Ile Leu His
        115                 120                 125
Asn Gly Ala Tyr Ser Leu Thr Leu Gln Gly Leu Gly Ile Ser Trp Leu
    130                 135                 140
Gly Leu Arg Ser Leu Arg Glu Leu Gly Ser Gly Leu Ala Leu Ile His
145                 150                 155                 160
His Asn Thr His Leu Cys Phe Val His Thr Val Pro Trp Asp Gln Leu
                165                 170                 175
Phe Arg Asn Pro His Gln Ala Leu Leu His Thr Ala Asn Arg Pro Glu
            180                 185                 190
Asp Glu Cys Val Gly Glu Gly Leu Ala Cys His Gln Leu Cys Ala Arg
        195                 200                 205
```

```
Gly His Cys Trp Gly Pro Gly Pro Thr Gln Cys Val Asn Cys Ser Gln
        210                 215                 220

Phe Leu Arg Gly Gln Glu Cys Val Glu Cys Arg Val Leu Gln Gly
225                 230                 235                 240

Leu Pro Arg Glu Tyr Val Asn Ala Arg His Cys Leu Pro Cys His Pro
                245                 250                 255

Glu Cys Gln Pro Gln Asn Gly Ser Val Thr Cys Phe Gly Pro Glu Ala
                260                 265                 270

Asp Gln Cys Val Ala Cys Ala His Tyr Lys Asp Pro Pro Phe Cys Val
                275                 280                 285

Ala Arg Cys Pro Ser Gly Val Lys Pro Asp Leu Ser Tyr Met Pro Ile
            290                 295                 300

Trp Lys Phe Pro Asp Glu Gly Ala Cys Gln Pro Cys Pro Ile Asn
305                 310                 315                 320

Cys Thr His Ser Cys Val Asp Leu Asp Asp Lys Gly Cys Pro Ala Glu
                325                 330                 335

Gln Arg Ala Ser Pro Leu Thr Ser
            340

<210> SEQ ID NO 3
<211> LENGTH: 344
<212> TYPE: PRT
<213> ORGANISM: Rattus rattus

<400> SEQUENCE: 3

Ser Cys Thr Leu Val Cys Pro Pro Asn Asn Gln Glu Val Thr Ala Glu
1               5                   10                  15

Asp Gly Thr Gln Arg Cys Glu Lys Cys Ser Lys Pro Cys Ala Arg Val
                20                  25                  30

Cys Tyr Gly Leu Gly Met Glu His Leu Arg Gly Ala Arg Ala Ile Thr
            35                  40                  45

Ser Asp Asn Val Gln Glu Phe Asp Gly Cys Lys Lys Ile Phe Gly Ser
        50                  55                  60

Leu Ala Phe Leu Pro Glu Ser Phe Asp Gly Asp Pro Ser Ser Gly Ile
65                  70                  75                  80

Ala Pro Leu Arg Pro Glu Gln Leu Gln Val Phe Glu Thr Leu Glu Glu
                85                  90                  95

Ile Thr Gly Tyr Leu Tyr Ile Ser Ala Trp Pro Asp Ser Leu Arg Asp
                100                 105                 110

Leu Ser Val Phe Gln Asn Leu Arg Ile Ile Arg Gly Arg Ile Leu His
            115                 120                 125

Asp Gly Ala Tyr Ser Leu Thr Leu Gln Gly Leu Gly Ile His Ser Leu
        130                 135                 140

Gly Leu Arg Ser Leu Arg Glu Leu Gly Ser Gly Leu Ala Leu Ile His
145                 150                 155                 160

Arg Asn Ala His Leu Cys Phe Val His Thr Val Pro Trp Asp Gln Leu
                165                 170                 175

Phe Arg Asn Pro His Gln Ala Leu Leu His Ser Gly Asn Arg Pro Glu
                180                 185                 190

Glu Asp Cys Gly Leu Glu Gly Leu Val Cys Asn Ser Leu Cys Ala His
            195                 200                 205

Gly His Cys Trp Gly Pro Gly Pro Thr Gln Cys Val Asn Cys Ser His
        210                 215                 220

Phe Leu Arg Gly Gln Glu Cys Val Glu Cys Arg Val Trp Lys Gly
225                 230                 235                 240
```

Leu Pro Arg Glu Tyr Val Ser Asp Lys Arg Cys Leu Pro Cys His Pro
            245                 250                 255

Glu Cys Gln Pro Gln Asn Ser Ser Glu Thr Cys Phe Gly Ser Glu Ala
        260                 265                 270

Asp Gln Cys Ala Ala Cys Ala His Tyr Lys Asp Ser Ser Ser Cys Val
    275                 280                 285

Ala Arg Cys Pro Ser Gly Val Lys Pro Asp Leu Ser Tyr Met Pro Ile
290                 295                 300

Trp Lys Tyr Pro Asp Glu Gly Ile Cys Gln Pro Cys Pro Ile Asn
305                 310                 315                 320

Cys Thr His Ser Cys Val Asp Leu Asp Glu Arg Gly Cys Pro Ala Glu
            325                 330                 335

Gln Arg Ala Ser Pro Val Thr Phe
            340

<210> SEQ ID NO 4
<211> LENGTH: 338
<212> TYPE: PRT
<213> ORGANISM: homo sapients

<400> SEQUENCE: 4

Thr Leu Val Cys Pro Leu His Asn Gln Glu Val Thr Ala Glu Asp Gly
1               5                   10                  15

Thr Gln Arg Cys Glu Lys Cys Ser Lys Pro Cys Ala Arg Val Cys Tyr
            20                  25                  30

Gly Leu Gly Met Glu His Leu Arg Glu Val Arg Ala Val Thr Ser Ala
        35                  40                  45

Asn Ile Gln Glu Phe Ala Gly Cys Lys Lys Ile Phe Gly Ser Leu Ala
    50                  55                  60

Phe Leu Pro Glu Ser Phe Asp Gly Asp Pro Ala Ser Asn Thr Ala Pro
65                  70                  75                  80

Leu Gln Pro Glu Gln Leu Gln Val Phe Glu Thr Leu Glu Glu Ile Thr
                85                  90                  95

Gly Tyr Leu Tyr Ile Ser Ala Trp Pro Asp Ser Leu Pro Asp Leu Ser
            100                 105                 110

Val Phe Gln Asn Leu Gln Val Ile Arg Gly Arg Ile Leu His Asn Gly
        115                 120                 125

Ala Tyr Ser Leu Thr Leu Gln Gly Leu Gly Ile Ser Trp Leu Gly Leu
    130                 135                 140

Arg Ser Leu Arg Glu Leu Gly Ser Gly Leu Ala Leu Ile His His Asn
145                 150                 155                 160

Thr His Leu Cys Phe Val His Thr Val Pro Trp Asp Gln Leu Phe Arg
                165                 170                 175

Asn Pro His Gln Ala Leu Leu His Thr Ala Asn Arg Pro Glu Asp Glu
            180                 185                 190

Cys Val Gly Glu Gly Leu Ala Cys His Gln Leu Cys Ala Arg Gly His
        195                 200                 205

Cys Trp Gly Pro Gly Pro Thr Gln Cys Val Asn Cys Ser Gln Phe Leu
    210                 215                 220

Arg Gly Gln Glu Cys Val Glu Cys Arg Val Leu Gln Gly Leu Pro
225                 230                 235                 240

Arg Glu Tyr Val Asn Ala Arg His Cys Leu Pro Cys His Pro Glu Cys
                245                 250                 255

Gln Pro Gln Asn Gly Ser Val Thr Cys Phe Gly Pro Glu Ala Asp Gln
            260                 265                 270

```
Cys Val Ala Cys Ala His Tyr Lys Asp Pro Pro Phe Cys Val Ala Arg
            275                 280                 285

Cys Pro Ser Gly Val Lys Pro Asp Leu Ser Tyr Met Pro Ile Trp Lys
        290                 295                 300

Phe Pro Asp Glu Glu Gly Ala Cys Gln Pro Cys Pro Ile Asn Cys Thr
305                 310                 315                 320

His Ser Cys Val Asp Leu Asp Asp Lys Gly Cys Pro Ala Glu Gln Arg
                325                 330                 335

Ala Ser

<210> SEQ ID NO 5
<211> LENGTH: 310
<212> TYPE: PRT
<213> ORGANISM: homo sapiens

<400> SEQUENCE: 5

Arg Val Cys Tyr Gly Leu Gly Met Glu His Leu Arg Glu Val Arg Ala
1               5                   10                  15

Val Thr Ser Ala Asn Ile Gln Glu Phe Ala Gly Cys Lys Lys Ile Phe
            20                  25                  30

Gly Ser Leu Ala Phe Leu Pro Glu Ser Phe Asp Gly Asp Pro Ala Ser
        35                  40                  45

Asn Thr Ala Pro Leu Gln Pro Glu Gln Leu Gln Val Phe Glu Thr Leu
    50                  55                  60

Glu Glu Ile Thr Gly Tyr Leu Tyr Ile Ser Ala Trp Pro Asp Ser Leu
65                  70                  75                  80

Pro Asp Leu Ser Val Phe Gln Asn Leu Gln Val Ile Arg Gly Arg Ile
                85                  90                  95

Leu His Asn Gly Ala Tyr Ser Leu Thr Leu Gln Gly Leu Gly Ile Ser
            100                 105                 110

Trp Leu Gly Leu Arg Ser Leu Arg Glu Leu Gly Ser Gly Leu Ala Leu
        115                 120                 125

Ile His His Asn Thr His Leu Cys Phe Val His Thr Val Pro Trp Asp
    130                 135                 140

Gln Leu Phe Arg Asn Pro His Gln Ala Leu Leu His Thr Ala Asn Arg
145                 150                 155                 160

Pro Glu Asp Glu Cys Val Gly Glu Gly Leu Ala Cys His Gln Leu Cys
                165                 170                 175

Ala Arg Gly His Cys Trp Gly Pro Gly Pro Thr Gln Cys Val Asn Cys
            180                 185                 190

Ser Gln Phe Leu Arg Gly Gln Glu Cys Val Glu Glu Cys Arg Val Leu
        195                 200                 205

Gln Gly Leu Pro Arg Glu Tyr Val Asn Ala Arg His Cys Leu Pro Cys
    210                 215                 220

His Pro Glu Cys Gln Pro Gln Asn Gly Ser Val Thr Cys Phe Gly Pro
225                 230                 235                 240

Glu Ala Asp Gln Cys Val Ala Cys Ala His Tyr Lys Asp Pro Pro Phe
                245                 250                 255

Cys Val Ala Arg Cys Pro Ser Gly Val Lys Pro Asp Leu Ser Tyr Met
            260                 265                 270

Pro Ile Trp Lys Phe Pro Asp Glu Glu Gly Ala Cys Gln Pro Cys Pro
        275                 280                 285
```

Ile Asn Cys Thr His Ser Cys Val Asp Leu Asp Asp Lys Gly Cys Pro
            290                 295                 300

Ala Glu Gln Arg Ala Ser
305                 310

<210> SEQ ID NO 6
<211> LENGTH: 1154
<212> TYPE: DNA
<213> ORGANISM: Artificial Sequence
<220> FEATURE:
<223> OTHER INFORMATION: rat Her2-ED44-His construct

<400> SEQUENCE: 6

```
aatggggaag caaatggccg ccctgtgtgg ctttctcctc gtggcgttgc tctggctcac      60
gcccgacgtc gcgtcaggtt cctgcactct ggtgtgtccc ccgaataacc aagaggtcac     120
agctgaggac ggaacacagc gttgtgagaa atgcagcaag ccctgtgctc gagtgtgcta     180
tggtctgggc atggagcacc ttcgaggggc gagggccatc accagtgaca atgtccagga     240
gtttgatggc tgcaagaaga tctttgggag cctggcattt tgccggagag ctttgatgg     300
ggacccctcc tccggcattg ctccgctgag gcctgagcag ctccaagtgt cgaaaccct     360
ggaggagatc acaggttacc tgtacatctc agcatggcca gacagtctcc gtgacctcag     420
tgtcttccag aaccttcgaa tcattcgggg acggattctc cacgatggcg cgtactcatt     480
gacactgcaa ggcctgggga tccactcgct ggggctgcgc tcactgcggg agctgggcag     540
tggattggct ctgattcacc gcaacgccca tctctgcttt gtacacactg taccttggga     600
ccagctcttc cggaacccac atcaggccct gctccacagt gggaaccggc cggaagagga     660
ttgtggactc gagggcttgg tctgtaactc actgtgtgcc cacggcact gctgggggcc     720
agggcccacc cagtgtgtca actgcagtca tttccttcgg ggccaggagt gtgtggagga     780
gtgccgagta tggaaggggc tcccccggga gtatgtgagt gacaagcgct gtctgccgtg     840
tcaccccgag tgtcagcctc aaaacagctc agaaacctgc tttggatcgg aggctgatca     900
gtgtgcagcc tgcgcccact acaaggactc gtcctcctgt gtggctcgct gcccagtgg     960
tgtgaaaccg gacctctcct acatgcccat ctggaagtac ccggatgagg agggcatatg    1020
ccagccgtgc cccatcaact gcacccactc ctgtgtggat ctggatgaac gaggctgccc    1080
agcagagcag agagccagcc cggtgacatt ctctggatca gcggccgccc atcatcatca    1140
tcatcattga gctt                                                      1154
```

<210> SEQ ID NO 7
<211> LENGTH: 382
<212> TYPE: PRT
<213> ORGANISM: Artificial Sequence
<220> FEATURE:
<223> OTHER INFORMATION: rat Her2-ED44-His

<400> SEQUENCE: 7

Met Gly Lys Gln Met Ala Ala Leu Cys Gly Phe Leu Leu Val Ala Leu
1               5                   10                  15

Leu Trp Leu Thr Pro Asp Val Ala Ser Gly Ser Cys Thr Leu Val Cys
            20                  25                  30

Pro Pro Asn Asn Gln Glu Val Thr Ala Glu Asp Gly Thr Gln Arg Cys
        35                  40                  45

Glu Lys Cys Ser Lys Pro Cys Ala Arg Val Cys Tyr Gly Leu Gly Met
    50                  55                  60

Glu His Leu Arg Gly Ala Arg Ala Ile Thr Ser Asp Asn Val Gln Glu
65                  70                  75                  80

Phe Asp Gly Cys Lys Lys Ile Phe Gly Ser Leu Ala Phe Leu Pro Glu
                85                  90                  95

Ser Phe Asp Gly Asp Pro Ser Ser Gly Ile Ala Pro Leu Arg Pro Glu
            100                 105                 110

Gln Leu Gln Val Phe Glu Thr Leu Glu Glu Ile Thr Gly Tyr Leu Tyr
        115                 120                 125

Ile Ser Ala Trp Pro Asp Ser Leu Arg Asp Leu Ser Val Phe Gln Asn
130                 135                 140

Leu Arg Ile Ile Arg Gly Arg Ile Leu His Asp Gly Ala Tyr Ser Leu
145                 150                 155                 160

Thr Leu Gln Gly Leu Gly Ile His Ser Leu Gly Leu Arg Ser Leu Arg
                165                 170                 175

Glu Leu Gly Ser Gly Leu Ala Leu Ile His Arg Asn Ala His Leu Cys
            180                 185                 190

Phe Val His Thr Val Pro Trp Asp Gln Leu Phe Arg Asn Pro His Gln
        195                 200                 205

Ala Leu Leu His Ser Gly Asn Arg Pro Glu Glu Asp Cys Gly Leu Glu
    210                 215                 220

Gly Leu Val Cys Asn Ser Leu Cys Ala His Gly His Cys Trp Gly Pro
225                 230                 235                 240

Gly Pro Thr Gln Cys Val Asn Cys Ser His Phe Leu Arg Gly Gln Glu
                245                 250                 255

Cys Val Glu Glu Cys Arg Val Trp Lys Gly Leu Pro Arg Glu Tyr Val
            260                 265                 270

Ser Asp Lys Arg Cys Leu Pro Cys His Pro Glu Cys Gln Pro Gln Asn
        275                 280                 285

Ser Ser Glu Thr Cys Phe Gly Ser Glu Ala Asp Gln Cys Ala Ala Cys
    290                 295                 300

Ala His Tyr Lys Asp Ser Ser Cys Val Ala Arg Cys Pro Ser Gly
305                 310                 315                 320

Val Lys Pro Asp Leu Ser Tyr Met Pro Ile Trp Lys Tyr Pro Asp Glu
                325                 330                 335

Glu Gly Ile Cys Gln Pro Cys Pro Ile Asn Cys Thr His Ser Cys Val
            340                 345                 350

Asp Leu Asp Glu Arg Gly Cys Pro Ala Glu Gln Arg Ala Ser Pro Val
        355                 360                 365

Thr Phe Ser Gly Ser Ala Ala His His His His His
    370                 375                 380

<210> SEQ ID NO 8
<211> LENGTH: 1484
<212> TYPE: DNA
<213> ORGANISM: Artificial Sequence
<220> FEATURE:
<223> OTHER INFORMATION: rat Her2-ED44-kappa construct

<400> SEQUENCE: 8
aatggggaag caaatggccg ccctgtgtgg ctttctcctc gtggcgttgc tctggctcac    60
gcccgacgtc gcgtcaggtt cctgcactct ggtgtgtccc ccgaataacc aagaggtcac   120
agctgaggac ggaacacagc gttgtgagaa atgcagcaag ccctgtgctc gagtgtgcta   180
tggtctgggc atggagcacc ttcgaggggc gaggcccatc accagtgaca atgtccagga   240
gtttgatggc tgcaagaaga tctttgggag cctggcattt ttgccggaga gctttgatgg   300

```
ggacccctcc tccggcattg ctccgctgag gcctgagcag ctccaagtgt tcgaaaccct    360
ggaggagatc acaggttacc tgtacatctc agcatggcca gacagtctcc gtgacctcag    420
tgtcttccag aaccttcgaa tcattcgggg acggattctc cacgatggcg cgtactcatt    480
gacactgcaa ggcctgggga tccactcgct ggggctgcgc tcactgcggg agctgggcag    540
tggattggct ctgattcacc gcaacgccca tctctgcttt gtacacactg taccttggga    600
ccagctcttc cggaacccac atcaggccct gctccacagt gggaaccggc cggaagagga    660
ttgtggactc gagggcttgg tctgtaactc actgtgtgcc cacgggcact gctggggcc     720 agggcccacc cagtgtgtca actgcagtca tttccttcgg gccaggagt gtgtggagga    780 gtgccgagta tggaaggggc tcccccggga gtatgtgagt gacaagcgct gtctgccgtg    840
tcaccccgag tgtcagcctc aaaacagctc agaaacctgc tttggatcgg aggctgatca    900
gtgtgcagcc tgcgcccact acaaggactc gtcctcctgt gtggctcgct gccccagtgg    960
tgtgaaaccg acctctcct acatgcccat ctggaagtac ccggatgagg agggcatatg    1020
ccagccgtgc cccatcaact gcacccactc tgtgtggat ctggatgaac gaggctgccc    1080
agcagagcag agagccagcc cggtgacatt cggaggcgga ggaagtggag gcggtggatc    1140
aggaggcggt ggctcacgaa cagttgctgc tcctagtgtt tttattttc ccccatccga    1200 tgaacaattg aaatctggaa ctgcatccgt agtatgcttg ttgaacaatt tctaccctag    1260
agaagctaag gttcaatgga agtcgataa tgcactacag tctggtaatt cacaagagtc    1320
tgttactgaa caagactcta aggactctac ttacagtctt tcttcaactc ttaccctatc    1380
aaaggcagat tacgaaaagc ataaggtcta tgcttgtgaa gttacacatc aaggattgag    1440
ttcaccagtt acaaagagtt ttaaccgtgg tgagtgttaa gctt                     1484
```

<210> SEQ ID NO 9
<211> LENGTH: 490
<212> TYPE: PRT
<213> ORGANISM: Artificial Sequence
<220> FEATURE:
<223> OTHER INFORMATION: rat Her2-ED44-kappa

<400> SEQUENCE: 9

```
Met Gly Lys Gln Met Ala Ala Leu Cys Gly Phe Leu Leu Val Ala Leu
1               5                   10                  15

Leu Trp Leu Thr Pro Asp Val Ala Ser Gly Ser Cys Thr Leu Val Cys
            20                  25                  30

Pro Pro Asn Asn Gln Glu Val Thr Ala Glu Asp Gly Thr Gln Arg Cys
        35                  40                  45

Glu Lys Cys Ser Lys Pro Cys Ala Arg Val Cys Tyr Gly Leu Gly Met
    50                  55                  60

Glu His Leu Arg Gly Ala Arg Ala Ile Thr Ser Asp Asn Val Gln Glu
65                  70                  75                  80

Phe Asp Gly Cys Lys Lys Ile Phe Gly Ser Leu Ala Phe Leu Pro Glu
                85                  90                  95

Ser Phe Asp Gly Asp Pro Ser Ser Gly Ile Ala Pro Leu Arg Pro Glu
            100                 105                 110

Gln Leu Gln Val Phe Glu Thr Leu Glu Glu Ile Thr Gly Tyr Leu Tyr
        115                 120                 125

Ile Ser Ala Trp Pro Asp Ser Leu Arg Asp Leu Ser Val Phe Gln Asn
    130                 135                 140

Leu Arg Ile Ile Arg Gly Arg Ile Leu His Asp Gly Ala Tyr Ser Leu
145                 150                 155                 160
```

```
Thr Leu Gln Gly Leu Gly Ile His Ser Leu Gly Arg Ser Leu Arg
                165                 170                 175

Glu Leu Gly Ser Gly Leu Ala Leu Ile His Arg Asn Ala His Leu Cys
            180                 185                 190

Phe Val His Thr Val Pro Trp Asp Gln Leu Phe Arg Asn Pro His Gln
        195                 200                 205

Ala Leu Leu His Ser Gly Asn Arg Pro Glu Glu Asp Cys Gly Leu Glu
    210                 215                 220

Gly Leu Val Cys Asn Ser Leu Cys Ala His Gly His Cys Trp Gly Pro
225                 230                 235                 240

Gly Pro Thr Gln Cys Val Asn Cys Ser His Phe Leu Arg Gly Gln Glu
                245                 250                 255

Cys Val Glu Glu Cys Arg Val Trp Lys Gly Leu Pro Arg Glu Tyr Val
            260                 265                 270

Ser Asp Lys Arg Cys Leu Pro Cys His Pro Glu Cys Gln Pro Gln Asn
        275                 280                 285

Ser Ser Glu Thr Cys Phe Gly Ser Glu Ala Asp Gln Cys Ala Ala Cys
    290                 295                 300

Ala His Tyr Lys Asp Ser Ser Ser Cys Val Ala Arg Cys Pro Ser Gly
305                 310                 315                 320

Val Lys Pro Asp Leu Ser Tyr Met Pro Trp Lys Tyr Pro Asp Glu Glu
                325                 330                 335

Gly Ile Cys Gln Pro Cys Pro Ile Asn Cys Thr His Ser Cys Val Asp
            340                 345                 350

Leu Asp Glu Arg Gly Cys Pro Ala Glu Arg Ala Ser Pro Val Thr Phe
        355                 360                 365

Gly Gly Gly Gly Ser Gly Gly Gly Ser Gly Gly Gly Ser Arg
    370                 375                 380

Thr Val Ala Ala Pro Ser Val Phe Ile Phe Pro Pro Ser Asp Glu Gln
385                 390                 395                 400

Leu Lys Ser Gly Thr Ala Ser Val Val Cys Leu Leu Asn Asn Phe Tyr
                405                 410                 415

Pro Arg Glu Ala Lys Val Gln Trp Lys Val Asp Asn Ala Leu Gln Ser
            420                 425                 430

Gly Asn Ser Gln Glu Ser Val Thr Glu Gln Asp Ser Lys Asp Ser Thr
        435                 440                 445

Tyr Ser Leu Ser Ser Thr Leu Thr Leu Ser Lys Ala Asp Tyr Glu Lys
    450                 455                 460

His Lys Val Tyr Ala Cys Glu Val Thr His Gln Gly Leu Ser Ser Pro
465                 470                 475                 480

Val Thr Lys Ser Phe Asn Arg Gly Glu Cys
                485                 490

<210> SEQ ID NO 10
<211> LENGTH: 1154
<212> TYPE: DNA
<213> ORGANISM: Artificial Sequence
<220> FEATURE:
<223> OTHER INFORMATION: human Her2-ED44-His construct

<400> SEQUENCE: 10
aatggggaag caaatggccg ccctgtgtgg ctttctcctc gtggcgttgc tctggctcac     60
gcccgacgtc gcgtcaggtt cttgtactct ggtatgtcca ctacacaatc aggaagtaac    120
cgctgaggat ggaactcaga ggtgtgagaa atgtagcaaa ccttgtgcta gagtttgcta    180
```

```
tggtttggga atggagcatc ttcgtgaagt tagagccgtt acgtctgcca atatccaaga      240
gtttgcaggc tgtaagaaga tattcggatc tttggcattt ctccctgaat cattcgatgg      300
tgatccagcg tcaaacacag caccattaca acctgagcaa ctccaagtgt ttgagacact      360
agaggagatt acgggtatc tctacatttc tgcgtggcct gactccttgc cagatctttc       420
agtgtttcag aacttgcaag tgattcgtgg taggatactt cacaacggtg cttatagcct      480
cacattacaa gggttgggca tttcatggct agggttacga agtcttagag aacttggttc      540
tggattggca cttatccacc ataacaccca tttgtgcttt gtgcacacag taccatggga      600
tcagttgttc agaaatcctc atcaagctct gctgcataca gctaatcgtc cagaagatga      660
gtgtgtcgga gaaggtctag catgtcacca gttatgcgct agaggccatt gttggggacc      720
tggaccaact cagtgcgtta attgcagtca gttcctcagg ggtcaggaat gtgtcgaaga      780
atgcagggtt ttacaagggc ttcctagaga atacgtgaat gcccgacatt gcctgccttg      840
tcatccagaa tgtcaacccc aaaatggttc cgttacttgt tttggcccag aggctgatca      900
gtgcgttgca tgcgcacact acaaggatcc acctttctgt gttgccagat gtccaagcgg      960
agtaaaacca gacctttcct atatgcccat ttggaaattt cccgatgaag agggagcttg     1020
ccaaccttgt cccataaact gcactcatag ttgcgtcgat ttggacgaca aaggttgtcc     1080
agctgaacaa agagcttctc cgcttacatc atctggatca gcggccgccc atcatcatca     1140
tcatcattga gctt                                                       1154
```

<210> SEQ ID NO 11  
<211> LENGTH: 382  
<212> TYPE: PRT  
<213> ORGANISM: Artificial Sequence  
<220> FEATURE:  
<223> OTHER INFORMATION: human Her2-ED44-His

<400> SEQUENCE: 11

```
Met Gly Lys Gln Met Ala Ala Leu Cys Gly Phe Leu Leu Val Ala Leu
1               5                   10                  15

Leu Trp Leu Thr Pro Asp Val Ala Ser Gly Ser Cys Thr Leu Val Cys
            20                  25                  30

Pro Leu His Asn Gln Glu Val Thr Ala Glu Asp Gly Thr Gln Arg Cys
        35                  40                  45

Glu Lys Cys Ser Lys Pro Cys Ala Arg Val Cys Tyr Gly Leu Gly Met
    50                  55                  60

Glu His Leu Arg Glu Val Arg Ala Val Thr Ser Ala Asn Ile Gln Glu
65                  70                  75                  80

Phe Ala Gly Cys Lys Lys Ile Phe Gly Ser Leu Ala Phe Leu Pro Glu
                85                  90                  95

Ser Phe Asp Gly Asp Pro Ala Ser Asn Thr Ala Pro Leu Gln Pro Glu
            100                 105                 110

Gln Leu Gln Val Phe Glu Thr Leu Glu Glu Ile Thr Gly Tyr Leu Tyr
        115                 120                 125

Ile Ser Ala Trp Pro Asp Ser Leu Pro Asp Leu Ser Val Phe Gln Asn
    130                 135                 140

Leu Gln Val Ile Arg Gly Arg Ile Leu His Asn Gly Ala Tyr Ser Leu
145                 150                 155                 160

Thr Leu Gln Gly Leu Gly Ile Ser Trp Leu Gly Leu Arg Ser Leu Arg
                165                 170                 175

Glu Leu Gly Ser Gly Leu Ala Leu Ile His His Asn Thr His Leu Cys
            180                 185                 190
```

```
Phe Val His Thr Val Pro Trp Asp Gln Leu Phe Arg Asn Pro His Gln
            195                 200                 205

Ala Leu Leu His Thr Ala Asn Arg Pro Glu Asp Glu Cys Val Gly Glu
    210                 215                 220

Gly Leu Ala Cys His Gln Leu Cys Ala Arg Gly His Cys Trp Gly Pro
225                 230                 235                 240

Gly Pro Thr Gln Cys Val Asn Cys Ser Gln Phe Leu Arg Gly Gln Glu
                245                 250                 255

Cys Val Glu Glu Cys Arg Val Leu Gln Gly Leu Pro Arg Glu Tyr Val
            260                 265                 270

Asn Ala Arg His Cys Leu Pro Cys His Pro Glu Cys Gln Pro Gln Asn
        275                 280                 285

Gly Ser Val Thr Cys Phe Gly Pro Glu Ala Asp Gln Cys Val Ala Cys
    290                 295                 300

Ala His Tyr Lys Asp Pro Pro Phe Cys Val Ala Arg Cys Pro Ser Gly
305                 310                 315                 320

Val Lys Pro Asp Leu Ser Tyr Met Pro Ile Trp Lys Phe Pro Asp Glu
                325                 330                 335

Glu Gly Ala Cys Gln Pro Cys Pro Ile Asn Cys Thr His Ser Cys Val
            340                 345                 350

Asp Leu Asp Asp Lys Gly Cys Pro Ala Glu Gln Arg Ala Ser Pro Leu
        355                 360                 365

Thr Ser Ser Gly Ser Ala Ala His His His His His
    370                 375                 380

<210> SEQ ID NO 12
<211> LENGTH: 1484
<212> TYPE: DNA
<213> ORGANISM: Artificial Sequence
<220> FEATURE:
<223> OTHER INFORMATION: human Her2-ED44-kappa construct

<400> SEQUENCE: 12
aatggggaag caaatggccg ccctgtgtgg ctttctcctc gtggcgttgc tctggctcac     60
gcccgacgtc gcgtcaggtt cttgtactct ggtatgtcca ctacacaatc aggaagtaac    120
cgctgaggat ggaactcaga ggtgtgagaa atgtagcaaa ccttgtgcta gagtttgcta    180
tggtttggga atgagcatc ttcgtgaagt tagagccgtt acgtctgcca atatccaaga    240
gtttgcaggc tgtaagaaga tattcggatc tttggcattt ctccctgaat cattcgatgg    300
tgatccagcg tcaaacacag caccattaca acctgagcaa ctccaagtgt ttgagacact    360
agaggagatt acggggtatc tctacatttc tgcgtggcct gactccttgc cagatctttc    420
agtgtttcag aacttgcaag tgattcgtgg taggatactt cacaacggtg cttatagcct    480
cacattacaa gggttgggca tttcatggct agggttacga agtcttagag aacttggttc    540
tggattggca cttatccacc ataacaccca tttgtgcttt gtgcacacag taccatggga    600
tcagttgttc agaaatcctc atcaagctct gctgcataca gctaatcgtc cagaagatga    660
gtgtgtcgga gaaggtctag catgtcacca gttatgcgct agaggccatt gttggggacc    720
tggaccaact cagtgcgtta attgcagtca gttcctcagg ggtcaggaat gtgtcgaaga    780
atgcagggtt ttacaagggc ttcctagaga atacgtgaat gcccgacatt gcctgccttg    840
tcatccagaa tgtcaacccc aaaatggttc cgttacttgt tttggcccag aggctgatca    900
gtgcgttgca tgcgcacact acaaggatcc acctttctgt gttgccagat gtccaagcgg    960
agtaaaacca gaccttttcct atatgcccat ttggaaattt cccgatgaag agggagcttg   1020
```

```
ccaaccttgt cccataaact gcactcatag ttgcgtcgat ttggacgaca aaggttgtcc    1080
agctgaacaa agagcttctc cgcttacatc aggaggcgga ggaagtggag gcggtggatc    1140
aggaggcggt ggctcacgaa cagttgctgc tcctagtgtt tttatttttc ccccatccga    1200
tgaacaattg aaatctggaa ctgcatccgt agtatgcttg ttgaacaatt tctaccctag    1260
agaagctaag gttcaatgga aagtcgataa tgcactacag tctggtaatt cacaagagtc    1320
tgttactgaa caagactcta aggactctac ttacagtctt tcttcaactc ttaccctatc    1380
aaaggcagat tacgaaaagc ataaggtcta tgcttgtgaa gttacacatc aaggattgag    1440
ttcaccagtt acaaagagtt ttaaccgtgg tgagtgttaa gctt                    1484
```

<210> SEQ ID NO 13
<211> LENGTH: 492
<212> TYPE: PRT
<213> ORGANISM: Artificial Sequence
<220> FEATURE:
<223> OTHER INFORMATION: human Her2-ED44-kappa

<400> SEQUENCE: 13

```
Met Gly Lys Gln Met Ala Ala Leu Cys Gly Phe Leu Leu Val Ala Leu
1               5                   10                  15

Leu Trp Leu Thr Pro Asp Val Ala Ser Gly Ser Cys Thr Leu Val Cys
            20                  25                  30

Pro Leu His Asn Gln Glu Val Thr Ala Glu Asp Gly Thr Gln Arg Cys
        35                  40                  45

Glu Lys Cys Ser Lys Pro Cys Ala Arg Val Cys Tyr Gly Leu Gly Met
    50                  55                  60

Glu His Leu Arg Glu Val Arg Ala Val Thr Ser Ala Asn Ile Gln Glu
65                  70                  75                  80

Phe Ala Gly Cys Lys Lys Ile Phe Gly Ser Leu Ala Phe Leu Pro Glu
                85                  90                  95

Ser Phe Asp Gly Asp Pro Ala Ser Asn Thr Ala Pro Leu Gln Pro Glu
            100                 105                 110

Gln Leu Gln Val Phe Glu Thr Leu Glu Glu Ile Thr Gly Tyr Leu Tyr
        115                 120                 125

Ile Ser Ala Trp Pro Asp Ser Leu Pro Asp Leu Ser Val Phe Gln Asn
    130                 135                 140

Leu Gln Val Ile Arg Gly Arg Ile Leu His Asn Gly Ala Tyr Ser Leu
145                 150                 155                 160

Thr Leu Gln Gly Leu Gly Ile Ser Trp Leu Gly Leu Arg Ser Leu Arg
                165                 170                 175

Glu Leu Gly Ser Gly Leu Ala Leu Ile His His Asn Thr His Leu Cys
            180                 185                 190

Phe Val His Thr Val Pro Trp Asp Gln Leu Phe Arg Asn Pro His Gln
        195                 200                 205

Ala Leu Leu His Thr Ala Asn Arg Pro Glu Asp Glu Cys Val Gly Glu
    210                 215                 220

Gly Leu Ala Cys His Gln Leu Cys Ala Arg Gly His Cys Trp Gly Pro
225                 230                 235                 240

Gly Pro Thr Gln Cys Val Asn Cys Ser Gln Phe Leu Arg Gly Gln Glu
                245                 250                 255

Cys Val Glu Glu Cys Arg Val Leu Gln Gly Leu Pro Arg Glu Tyr Val
            260                 265                 270

Asn Ala Arg His Cys Leu Pro Cys His Pro Glu Cys Gln Pro Gln Asn
        275                 280                 285
```

Gly Ser Val Thr Cys Phe Gly Pro Glu Ala Asp Gln Cys Val Ala Cys
    290                 295                 300
Ala His Tyr Lys Asp Pro Pro Phe Cys Val Ala Arg Cys Pro Ser Gly
305                 310                 315                 320
Val Lys Pro Asp Leu Ser Tyr Met Pro Ile Trp Lys Phe Pro Asp Glu
                325                 330                 335
Glu Gly Ala Cys Gln Pro Cys Pro Ile Asn Cys Thr His Ser Cys Val
            340                 345                 350
Asp Leu Asp Asp Lys Gly Cys Pro Ala Glu Gln Arg Ala Ser Pro Leu
        355                 360                 365
Thr Ser Gly Gly Gly Ser Gly Gly Gly Ser Gly Gly Gly Gly
    370                 375                 380
Ser Arg Thr Val Ala Ala Pro Ser Val Phe Ile Phe Pro Pro Ser Asp
385                 390                 395                 400
Glu Gln Leu Lys Ser Gly Thr Ala Ser Val Val Cys Leu Leu Asn Asn
                405                 410                 415
Phe Tyr Pro Arg Glu Ala Lys Val Gln Trp Lys Val Asp Asn Ala Leu
            420                 425                 430
Gln Ser Gly Asn Ser Gln Glu Ser Val Thr Glu Gln Asp Ser Lys Asp
        435                 440                 445
Ser Thr Tyr Ser Leu Ser Ser Thr Leu Thr Leu Ser Lys Ala Asp Tyr
    450                 455                 460
Glu Lys His Lys Val Tyr Ala Cys Glu Val Thr His Gln Gly Leu Ser
465                 470                 475                 480
Ser Pro Val Thr Lys Ser Phe Asn Arg Gly Glu Cys
                485                 490

<210> SEQ ID NO 14
<211> LENGTH: 1805
<212> TYPE: DNA
<213> ORGANISM: Artificial Sequence
<220> FEATURE:
<223> OTHER INFORMATION: Tetanus toxin fragment C-kappa construct

<400> SEQUENCE: 14
aatggggaag caaatggccg ccctgtgtgg ctttctcctc gtggcgttgc tctggctcac      60
gcccgacgtc gcgtctggta aaaaccttga ttgttgggtc gacaacgaag aggacatcga     120
tgttatcctg aaaaagtcta ccattctgaa cttggacatc aacaacgata ttatctccga     180
catctctggt ttcaactcct ctgttatcac atatccagat gctcaattgg tgccgggcat     240
caacggcaaa gctatccacc tggttaacaa cgaatcttct gaagttatcg tgcacaaggc     300
catggacatc gaatacaacg acatgttcaa caacttcacc gttagcttct ggctgcgcgt     360
tccgaaagtt tctgcttccc acctggaaca gtacggcact aacgagtact ccatcatcag     420
ctctatgaag aaacactccc tgtccatcgg ctctggttgg tctgtttccc tgaagggtaa     480
caacctgatc tggactctga aagactccgc gggcgaagtt cgtcagatca ctttccgcga     540
cctgccggac aagttcaacg cgtacctggc taacaaatgg gttttcatca ctatcactaa     600
cgatcgtctg tcatctgcta acctgtacat caacggcgtt ctgatgggct ccgctgaaat     660
cactggtctg ggcgctatcc gtgaggacaa caacatcact cttaagctgg accgttgcaa     720
caacaacaac cagtacgtat ccatcgacaa gttccgtatc ttctgcaaag cactgaaccc     780
gaaagagatc gaaaaactgt ataccagcta cctgtctatc accttcctgc gtgacttctg     840
gggtaacccg ctgcgttacg acaccgaata ttacctgatc ccggtagctt ctagctctaa     900

```
agacgttcag ctgaaaaaca tcactgacta catgtacctg accaacgcgc cgtcctacac    960
taacggtaaa ctgaacatct actaccgacg tctgtacaac ggcctgaaat tcatcatcaa   1020
acgctacact ccgaacaacg aaatcgattc tttcgttaaa tctggtgact tcatcaaact   1080
gtacgtttct tacaacaaca acgaacacat cgttggttac ccgaaagacg gtaacgcttt   1140
caacaacctg gacagaattc tgcgtgttgg ttacaacgct ccgggtatcc cgctgtacaa   1200
aaaaatggaa gctgttaaac tgcgtgacct gaaaacctac tctgttcagc tgaaactgta   1260
cgacgacaaa aacgcttctc tgggtctggt tggtacccac aacggtcaga tcggtaacga   1320
cccgaaccgt gacatcctga tcgcttctaa ctggtacttc aaccacctga agacaaaat   1380
cctgggttgc gactggtact tcgttccgac cgatgaaggt tggaccaacg acggaggcgg   1440
aggaagtgga ggcggtggat caggaggcgg tggctcacga acagttgctg ctcctagtgt   1500
ttttattttt cccccatccg atgaacaatt gaaatctgga actgcatccg tagtatgctt   1560
gttgaacaat ttctacccta gagaagctaa ggttcaatgg aaagtcgata atgcactaca   1620
gtctggtaat tcacaagagt ctgttactga acaagactct aaggactcta cttacagtct   1680
ttcttcaact cttaccctat caaaggcaga ttacgaaaag cataaggtct atgcttgtga   1740
agttacacat caaggattga gttcaccagt tacaaagagt tttaaccgtg gtgagtgtta   1800
agctt                                                             1805
```

<210> SEQ ID NO 15
<211> LENGTH: 599
<212> TYPE: PRT
<213> ORGANISM: Artificial Sequence
<220> FEATURE:
<223> OTHER INFORMATION: Tetanus toxin fragment C-kappa

<400> SEQUENCE: 15

```
Met Gly Lys Gln Met Ala Ala Leu Cys Gly Phe Leu Leu Val Ala Leu
1               5                   10                  15

Leu Trp Leu Thr Pro Asp Val Ala Ser Gly Lys Asn Leu Asp Cys Trp
            20                  25                  30

Val Asp Asn Glu Glu Asp Ile Asp Val Ile Leu Lys Lys Ser Thr Ile
        35                  40                  45

Leu Asn Leu Asp Ile Asn Asn Asp Ile Ile Ser Asp Ile Ser Gly Phe
    50                  55                  60

Asn Ser Ser Val Ile Thr Tyr Pro Asp Ala Gln Leu Val Pro Gly Ile
65                  70                  75                  80

Asn Gly Lys Ala Ile His Leu Val Asn Asn Glu Ser Ser Glu Val Ile
                85                  90                  95

Val His Lys Ala Met Asp Ile Glu Tyr Asn Asp Met Phe Asn Asn Phe
            100                 105                 110

Thr Val Ser Phe Trp Leu Arg Val Pro Lys Val Ser Ala Ser His Leu
        115                 120                 125

Glu Gln Tyr Gly Thr Asn Glu Tyr Ser Ile Ile Ser Ser Met Lys Lys
    130                 135                 140

His Ser Leu Ser Ile Gly Ser Gly Trp Ser Val Ser Leu Lys Gly Asn
145                 150                 155                 160

Asn Leu Ile Trp Thr Leu Lys Asp Ser Ala Gly Glu Val Arg Gln Ile
                165                 170                 175

Thr Phe Arg Asp Leu Pro Asp Lys Phe Asn Ala Tyr Leu Ala Asn Lys
            180                 185                 190
```

```
Trp Val Phe Ile Thr Ile Thr Asn Asp Arg Leu Ser Ala Asn Leu
            195                 200                 205

Tyr Ile Asn Gly Val Leu Met Gly Ser Ala Glu Ile Thr Gly Leu Gly
    210                 215                 220

Ala Ile Arg Glu Asp Asn Asn Ile Thr Leu Lys Leu Asp Arg Cys Asn
225                 230                 235                 240

Asn Asn Asn Gln Tyr Val Ser Ile Asp Lys Phe Arg Ile Phe Cys Lys
                245                 250                 255

Ala Leu Asn Pro Lys Glu Ile Glu Lys Leu Tyr Thr Ser Tyr Leu Ser
            260                 265                 270

Ile Thr Phe Leu Arg Asp Phe Trp Gly Asn Pro Leu Arg Tyr Asp Thr
    275                 280                 285

Glu Tyr Tyr Leu Ile Pro Val Ala Ser Ser Lys Asp Val Gln Leu
290                 295                 300

Lys Asn Ile Thr Asp Tyr Met Tyr Leu Thr Asn Ala Pro Ser Tyr Thr
305                 310                 315                 320

Asn Gly Lys Leu Asn Ile Tyr Tyr Arg Arg Leu Tyr Asn Gly Leu Lys
                325                 330                 335

Phe Ile Ile Lys Arg Tyr Thr Pro Asn Asn Glu Ile Asp Ser Phe Val
            340                 345                 350

Lys Ser Gly Asp Phe Ile Lys Leu Tyr Val Ser Tyr Asn Asn Asn Glu
    355                 360                 365

His Ile Val Gly Tyr Pro Lys Asp Gly Asn Ala Phe Asn Asn Leu Asp
    370                 375                 380

Arg Ile Leu Arg Val Gly Tyr Asn Ala Pro Gly Ile Pro Leu Tyr Lys
385                 390                 395                 400

Lys Met Glu Ala Val Lys Leu Arg Asp Leu Lys Thr Tyr Ser Val Gln
                405                 410                 415

Leu Lys Leu Tyr Asp Asp Lys Asn Ala Ser Leu Gly Leu Val Gly Thr
            420                 425                 430

His Asn Gly Gln Ile Gly Asn Asp Pro Asn Arg Asp Ile Leu Ile Ala
    435                 440                 445

Ser Asn Trp Tyr Phe Asn His Leu Lys Asp Lys Ile Leu Gly Cys Asp
    450                 455                 460

Trp Tyr Phe Val Pro Thr Asp Glu Gly Trp Thr Asn Asp Gly Gly Gly
465                 470                 475                 480

Gly Ser Gly Gly Gly Ser Gly Gly Gly Ser Arg Thr Val Ala
                485                 490                 495

Ala Pro Ser Val Phe Ile Phe Pro Pro Ser Asp Glu Gln Leu Lys Ser
            500                 505                 510

Gly Thr Ala Ser Val Val Cys Leu Leu Asn Asn Phe Tyr Pro Arg Glu
    515                 520                 525

Ala Lys Val Gln Trp Lys Val Asp Asn Ala Leu Gln Ser Gly Asn Ser
    530                 535                 540

Gln Glu Ser Val Thr Glu Gln Asp Ser Lys Asp Ser Thr Tyr Ser Leu
545                 550                 555                 560

Ser Ser Thr Leu Thr Leu Ser Lys Ala Asp Tyr Glu Lys His Lys Val
                565                 570                 575

Tyr Ala Cys Glu Val Thr His Gln Gly Leu Ser Ser Pro Val Thr Lys
            580                 585                 590

Ser Phe Asn Arg Gly Glu Cys
            595
```

<210> SEQ ID NO 16
<211> LENGTH: 161
<212> TYPE: PRT
<213> ORGANISM: Artificial Sequence
<220> FEATURE:
<223> OTHER INFORMATION: TMV-CPlys

<400> SEQUENCE: 16

```
Met Ala Asp Phe Lys Ser Tyr Asn Ile Thr Asn Pro Asn Gln Tyr Gln
1               5                   10                  15

Tyr Phe Ala Ala Val Trp Ala Glu Pro Ile Pro Met Leu Asn Gln Cys
            20                  25                  30

Met Ser Ala Leu Ser Gln Ser Tyr Gln Thr Gln Ala Ala Arg Asp Thr
        35                  40                  45

Val Arg Gln Gln Phe Ser Asn Leu Leu Ser Ala Val Val Thr Pro Ser
    50                  55                  60

Gln Arg Phe Pro Asp Thr Gly Ser Arg Val Tyr Val Asn Ser Ala Val
65                  70                  75                  80

Ile Lys Pro Leu Tyr Glu Ala Leu Met Lys Ser Phe Asp Thr Arg Asn
                85                  90                  95

Arg Ile Ile Glu Thr Glu Glu Ser Arg Pro Ser Ala Ser Glu Val
            100                 105                 110

Ala Asn Ala Thr Gln Arg Val Asp Asp Ala Thr Val Ala Ile Arg Ser
        115                 120                 125

Gln Ile Gln Leu Leu Leu Ser Glu Leu Ser Asn Gly His Gly Tyr Met
    130                 135                 140

Asn Arg Ala Glu Phe Glu Ala Leu Leu Pro Trp Thr Thr Ala Pro Ala
145                 150                 155                 160

Thr
```

<210> SEQ ID NO 17
<211> LENGTH: 265
<212> TYPE: PRT
<213> ORGANISM: Artificial Sequence
<220> FEATURE:
<223> OTHER INFORMATION: DOM1 domain of tetanus toxin fragment C

<400> SEQUENCE: 17

```
Met Gly Trp Ser Cys Ile Ile Phe Phe Leu Val Ala Thr Ala Thr Gly
1               5                   10                  15

Val His Ser Lys Asn Leu Asp Cys Trp Val Asp Asn Glu Glu Asp Ile
            20                  25                  30

Asp Val Ile Leu Lys Lys Ser Thr Ile Leu Asn Leu Asp Ile Asn Asn
        35                  40                  45

Asp Ile Ile Ser Asp Ile Ser Gly Phe Asn Ser Ser Val Ile Thr Tyr
    50                  55                  60

Pro Asp Ala Gln Leu Val Pro Gly Ile Asn Gly Lys Ala Ile His Leu
65                  70                  75                  80

Val Asn Asn Glu Ser Ser Glu Val Ile Val His Lys Ala Met Asp Ile
                85                  90                  95

Glu Tyr Asn Asp Met Phe Asn Asn Phe Thr Val Ser Phe Trp Leu Arg
            100                 105                 110

Val Pro Lys Val Ser Ala Ser His Leu Glu Gln Tyr Gly Thr Asn Glu
        115                 120                 125

Tyr Ser Ile Ile Ser Ser Met Lys Lys His Ser Leu Ser Ile Gly Ser
    130                 135                 140
```

```
Gly Trp Ser Val Ser Leu Lys Gly Asn Asn Leu Ile Trp Thr Leu Lys
145                 150                 155                 160

Asp Ser Ala Gly Glu Val Arg Gln Ile Thr Phe Arg Asp Leu Pro Asp
                165                 170                 175

Lys Phe Asn Ala Tyr Leu Ala Asn Lys Trp Val Phe Ile Thr Ile Thr
            180                 185                 190

Asn Asp Arg Leu Ser Ser Ala Asn Leu Tyr Ile Asn Gly Val Leu Met
            195                 200                 205

Gly Ser Ala Glu Ile Thr Gly Leu Gly Ala Ile Arg Glu Asp Asn Asn
        210                 215                 220

Ile Thr Leu Lys Leu Asp Arg Cys Asn Asn Asn Gln Tyr Val Ser
225                 230                 235                 240

Ile Asp Lys Phe Arg Ile Phe Cys Lys Ala Leu Asn Pro Lys Glu Ile
            245                 250                 255

Glu Lys Leu Tyr Thr Ser Tyr Leu Ser
        260                 265

<210> SEQ ID NO 18
<211> LENGTH: 1255
<212> TYPE: PRT
<213> ORGANISM: Homo sapiens

<400> SEQUENCE: 18

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

-continued

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Val Leu Gly Val Val Phe Gly
            660                 665                 670

```
Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065
```

```
Glu Ala Pro Arg Ser Pro Leu Ala Pro Ser Glu Gly Ala Gly Ser
    1070            1075            1080

Asp Val Phe Asp Gly Asp Leu Gly Met Gly Ala Ala Lys Gly Leu
    1085            1090            1095

Gln Ser Leu Pro Thr His Asp Pro Ser Pro Leu Gln Arg Tyr Ser
    1100            1105            1110

Glu Asp Pro Thr Val Pro Leu Pro Ser Glu Thr Asp Gly Tyr Val
    1115            1120            1125

Ala Pro Leu Thr Cys Ser Pro Gln Pro Glu Tyr Val Asn Gln Pro
    1130            1135            1140

Asp Val Arg Pro Gln Pro Pro Ser Pro Arg Glu Gly Pro Leu Pro
    1145            1150            1155

Ala Ala Arg Pro Ala Gly Ala Thr Leu Glu Arg Ala Lys Thr Leu
    1160            1165            1170

Ser Pro Gly Lys Asn Gly Val Val Lys Asp Val Phe Ala Phe Gly
    1175            1180            1185

Gly Ala Val Glu Asn Pro Glu Tyr Leu Thr Pro Gln Gly Gly Ala
    1190            1195            1200

Ala Pro Gln Pro His Pro Pro Pro Ala Phe Ser Pro Ala Phe Asp
    1205            1210            1215

Asn Leu Tyr Tyr Trp Asp Gln Asp Pro Pro Glu Arg Gly Ala Pro
    1220            1225            1230

Pro Ser Thr Phe Lys Gly Thr Pro Thr Ala Glu Asn Pro Glu Tyr
    1235            1240            1245

Leu Gly Leu Asp Val Pro Val
    1250            1255

<210> SEQ ID NO 19
<211> LENGTH: 26
<212> TYPE: PRT
<213> ORGANISM: Oryza sativa

<400> SEQUENCE: 19

Met Gly Lys Gln Met Ala Ala Leu Cys Gly Phe Leu Leu Val Ala Leu
1               5                   10                  15

Leu Trp Leu Thr Pro Asp Val Ala His Ala
            20                  25

<210> SEQ ID NO 20
<211> LENGTH: 26
<212> TYPE: PRT
<213> ORGANISM: Artificial Sequence
<220> FEATURE:
<223> OTHER INFORMATION: modified rice alpha amylase signal peptide

<400> SEQUENCE: 20

Met Gly Lys Gln Met Ala Ala Leu Cys Gly Phe Leu Leu Val Ala Leu
1               5                   10                  15

Leu Trp Leu Thr Pro Asp Val Ala Ser Gly
            20                  25

<210> SEQ ID NO 21
<211> LENGTH: 15
<212> TYPE: PRT
<213> ORGANISM: Artificial Sequence
<220> FEATURE:
<223> OTHER INFORMATION: linker
```

```
<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 51
<212> TYPE: DNA
<213> ORGANISM: Artificial Sequence
<220> FEATURE:
<223> OTHER INFORMATION: primer

<400> SEQUENCE: 22
tttggtctca aatggctgac tttaagagct ataacatcac gaatcctaac c          51
```